United States Patent
Beguin et al.

(10) Patent No.: US 9,018,000 B2
(45) Date of Patent: Apr. 28, 2015

(54) VOLTAGE GATED CALCIUM CHANNEL β-SUBUNIT ANCHORING REGULATOR PROTEIN AND USES THEREOF

(75) Inventors: Pascal Beguin, Proteos (SG); Walter Hunziker, Proteos (SG)

(73) Assignee: Agency for Science, Technology and Research, Singapore (SG)

( * ) Notice: Subject to any disclaimer, the term of this patent is extended or adjusted under 35 U.S.C. 154(b) by 1289 days.

(21) Appl. No.: 12/665,159

(22) PCT Filed: Jun. 18, 2008

(86) PCT No.: PCT/SG2008/000214
§ 371 (c)(1),
(2), (4) Date: Jun. 21, 2010

(87) PCT Pub. No.: WO2008/156428
PCT Pub. Date: Dec. 24, 2008

(65) Prior Publication Data
US 2010/0272737 A1 Oct. 28, 2010

Related U.S. Application Data

(60) Provisional application No. 60/936,041, filed on Jun. 18, 2007.

(51) Int. Cl.
| | | |
|---|---|---|
| *C12N 15/00* | (2006.01) | |
| *G01N 33/68* | (2006.01) | |
| *C07K 14/47* | (2006.01) | |
| *C07K 14/705* | (2006.01) | |
| *A61K 38/00* | (2006.01) | |

(52) U.S. Cl.
CPC ............ *G01N 33/6872* (2013.01); *A61K 38/00* (2013.01); *C07K 14/4702* (2013.01); *C07K 14/705* (2013.01); *G01N 2800/042* (2013.01)

(58) Field of Classification Search
None
See application file for complete search history.

(56) References Cited

FOREIGN PATENT DOCUMENTS

| SG | 157720 | 9/2012 |
| WO | WO2005/108415 | 11/2005 |
| WO | WO 2006/110593 | * 10/2006 |

OTHER PUBLICATIONS

Beguin, et al (2001) Regulation of Ca2+ channel expression at the cell surface by the small G-protein kir/Gem. Nature, 411: 701-706.*
International Preliminary Report on Patentability mailed Nov. 2, 2009 in connection with PCT/SG2008/000214.
International Search Report and Written Opinion mailed Feb. 20, 2009 in connection with PCT/SG2008/000214.
Beguin, et al. "RGK small GTP-binding proteins interact with the nucleotide kinasa domain of Ca2+-channel beta-subunits via an uncommon effector binding domain" Journal of Biology Chemistry, vol. 282, No. 15, Apr. 2007.
Beguin et al., "Nuclear Sequestration of beta-Subunits by Rem is controlled by 14-3-3 and Calmodulin and Reveals a Novel Mechanism for Ca<2+> Channel Regulation" Journel of Molecular Biology, vol. 355, No. 1 Jan. 6, 2006.
Hidalgo et al. "Multiplicity of protein interactions and functions of the voltage-gated calcium channel beta-subunit" Livingston Medical Journals, vol. 42, No, 4-5, Aug. 21, 2007.
Beguin et al., "14-3-3 and calmodulin control subcellular distribution of Kir/Gem and its regulation of cell shape and calcium channel activity" Journal of Cell Science, vol. 118, No. 9, May 9, 2005.
Kelly et al., "The RGK family: a regulatory tail of small GTP-binding proteins" Trends in Cell Biology, Elsevier Science Ltd, vol. 15, No. 12, Dec. 1, 2005.
Genbank Submission; NIH/NCBI, Accession No. AAH28156.1. Strausberg et al., Jul. 15, 2006. 2 pages.

* cited by examiner

*Primary Examiner* — Michael Pak
(74) *Attorney, Agent, or Firm* — Wolf, Greenfield & Sacks, P.C.

(57) ABSTRACT

The present invention relates to a novel gene encoding a protein termed voltage gated calcium channels β subunit anchoring regulator protein (VDCC BARP) or a peptide fragments thereof. The present invention also relates to the use of VDCC BARP in Modulation of voltage gated calcium channels via altering the concentration of VDCC BARP or a peptide fragments thereof.

7 Claims, 9 Drawing Sheets

Figure 2C (a) α Helix
GST-BARP(Dom.I) $^{422}$SYR■■■$_{442}$
GST-Ca$_v$1.2(AID) $^{458}$DEAQ■■■LKQFDGRAKAKEREK$_{422}$
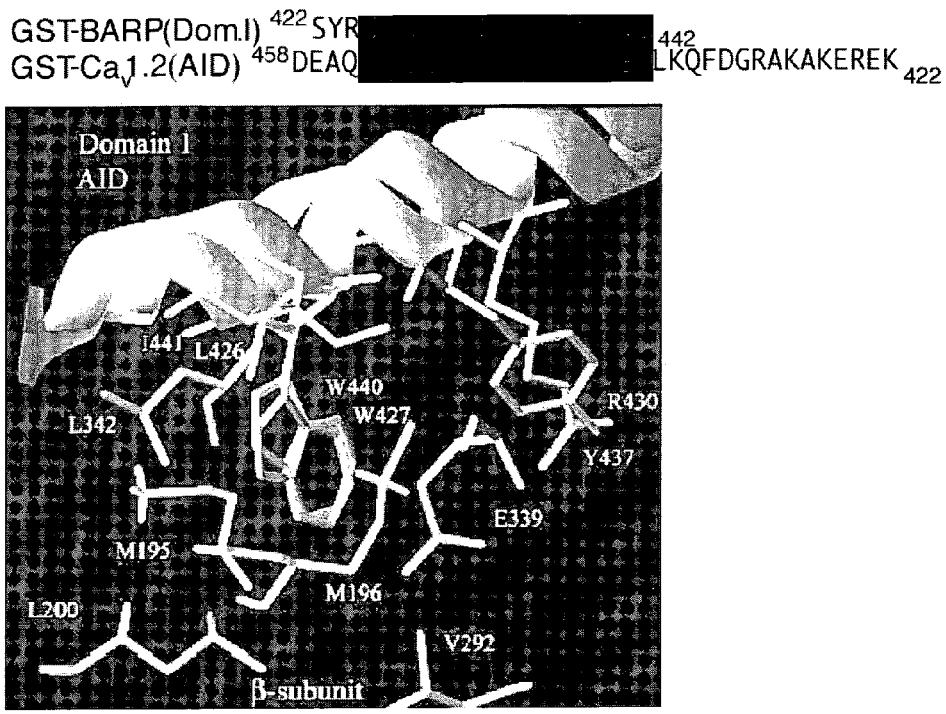
Figure 2C (b)
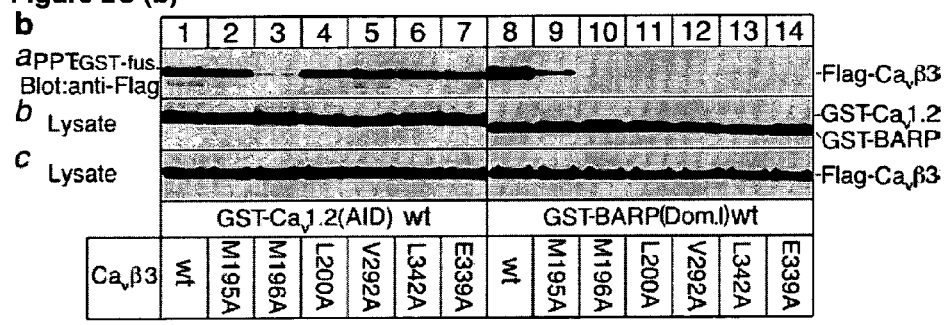
Figure 2C (c)
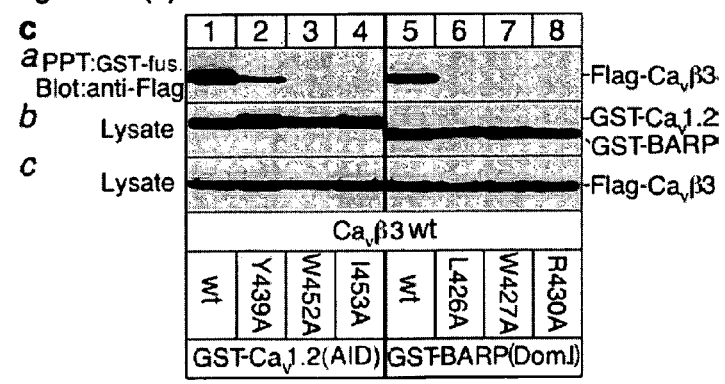

GST-BARP(Dom.II) $^{525}$PRAWPRRPRRDYSIDEKTDALFHEFLRHDPHFDDAPRHR$_{563}$

```
           1               N-glycosylation site              TM              66
mouse  MQPTATMATAAATT----ATVALTTSWDNATSRPTAEPDPILDN[                          ]
rat    MQPTATMATAAATT----ATVALTTSWDNATNRPTAEPDPILDN[                          ]
human  MQPTATMATATATTTTTTATVALTTSWDNATGRPTAEPDPILDN[                          ]

67                                                              136
mouse  KRCWEVHQRFNRAMEEAEKTTTTYLDNGTHPIQDPDCRGEDPEGQDTETERFLATSSTGRRVSFNEAALF
rat    KRCWEVHQRFNRAMEETEKTTTTYLDNGTHPIQDPDCRGEDPEGQDTETERFLATTSTGRRVSFNEAALF
human  KRCWDVHQRFNRAMEEAEKTTTTYLDNGTHPAQDPDFRGEDPECQDAETERFLSTSSTGRRVSFNEAALF 137                                                             204
mouse  EQSRKAQDKGRRYTLTEGDFHHLKNARLTHLHLPPLKIATIHECDSGEASAAATPHP--ATTSKDSLAIF
rat    EQSRKAQDKGRRYTLTEGDFHHLKNARLTHLHLPPLKIATIHECDSGEASAAATPHPHPASTPKDSLAIF
human  EQSRKTQDKGRRYTLTEGDFHHLKNARLTHLHLPPLKIVTIHECDSGEASSATTPHP--ATSPKATLAIF 205                                                             268
mouse  QPPGKTLTGHSVGPSSALPGGPYNSV----DFSEISPSTSSDSGEGISLDAGTRGAKAAGPETV--PGEM
rat    QPPGKSLTGHSVGPSSALPGDPYSSV----DFSEISPSASSDSGEGTSLDAGTRGTKAAGPETA--PGEM
human  QPPGKALTGRSVGPSSALPGDPYNSATGATDFAEISPSASSDSGEGTSLDAGTRSTKAGGPGAAAGPGEA 269                                                             338
mouse  GTGSSGSGTVLQFFTRLRRHASLDGASPYFKVKKWKLEPSQRASSLDTRGSPKRHHFQRQRAASESMEQE
rat    GTGSSGAGTVLQFFTRLRRHASLDGASPYFKVKKWKLESSQRASSLDTRGSPKRHHFQRQRAASESMEQE
human  GPGS-GAGTVLQFLTRLRRHASLDGASPYFKVKKWKLEPSQRAASLDTRGSPKRHHFQRQRAASESTEQE 339                                                             406
mouse  -GDVPHADFIQYIASAGDSVAFPPPRPFLASPTSPPPTLGRLEAAEAAGGASPETPPEHGI-SLGPEHAQ
rat    -GDIPHADFIQYIASAGDSVAFPPPRPFLASPTSPPPTLGRLEAAEAAGGGSPETPPEHGI-SLGPEHAQ
human  EGDAPQEDFIQYIARAGDAVAFPHPRPFLASP---PPALGRLEAAEAAGGASPDSPPERGAGSAGPE--Q 407                Domain I                                     470
mouse  QQDPQQEQDAE------HAQC[SYRDLWSLRASLELHAATASD]HSSSGNDRDSVRSGDSSGSGSGGGAAP
rat    QQDPQQEQDAE------HAQC[SYRDLWSLRASLELHAATASD]HSSSGNDRDSVRSGDSSGSGSGGGAAP
human  QQPP-LEPDAERDAGPEQAQT[SYRDLWSLRASLELHAA-ASD]HSSSGNDRDSVRSGDSSGSGSGG--AAP 471                                                             540
mouse  AFPPPPESPPALRPKDGEARRLLQMDSGYASIEGRGAGDEVSELPAPARSPPRS[PRAWPRRPRRDYSIDE]
rat    AFPPPPESPPALRPKDGEARRLLQMDSGYASIEGRGAGDEVSELPAPARSPPRS[PRAWPRRPRRDYSIDE]
human  AFPPP--SPPAPRPKDGEARRLLQMDSGYASIEGRGAGDDTEPPAAPAR--PRS[PRAWPRRPRRDYSIDE]

541    Domain II                                                600
mouse  [KTDALFHEFLRHDPHFDDAP----RHRI]RAHPHTHARKQWQQRGRQHSDPGG-------ARAAATPPGVARP
rat    [KTDALFHEFLRHDPHFDDAP---RHRA]RAHPHTHARKQWQQRGRQHSDPGG-------ARVATPPGATRP
human  [KTDALFHEFLRHDPHFDDIPAAARHRA]RAHPH--ARKQWQ-RGRQHSDPGARAAPALAGTPAPPAGAARP 601                                                             670
mouse  TRAPLRRGDSVDCPPEGRALPITGDDPSIPVIEEEPGGGGGGCPGSGLCVEPAGALLDKLAASLDERLFS
rat    TRAPLRRGDSVDCPPEGRAPPITGDDPSIPVIEEEPGGGGSGCPGSGLCVEPAGALLDKLAASLDERLFS
human  ARAPLRRGDSVDGPPDGRTLGGAGDDPAIPVIEEEPGGGG--CPGSGLCVLPSGSVLDKLAAGLDERLFP 671      698
mouse  PRLAEPVASSQVLIVAAAAPTSPDHSPA
rat    PRLAEPVASSPVLIVAAAAPTSPDHSPA
human  PRLAEPVVATPAL-V-AAAPTSPDHSPA
```

US 9,018,000 B2

VOLTAGE GATED CALCIUM CHANNEL β-SUBUNIT ANCHORING REGULATOR PROTEIN AND USES THEREOF

PRIORITY CLAIM

This is a U.S. national stage of PCT Application No. PCT/SG2008/000214, filed on Jun. 18, 2008. Priority is claimed from U.S. Provisional Application No. 60/936,041, filed Jun. 18, 2007, the contents of which are incorporated herein by reference.

SEQUENCE LISTING

The instant application contains a Sequence Listing which has been submitted via EFS-Web and is hereby incorporated by reference in its entirety. Said ASCII copy, created on Jun. 18, 2010, is named 57452PUS.txt and is 31,846 bytes in size.

FIELD OF THE INVENTION

The invention relates generally to the field of voltage gated calcium channels. Specifically, the present invention relates to modulators of voltage gated calcium channels including a gene and the amino acid it encodes. More specifically, the invention relates the use of the sequences, including mutations and alleles thereof, in the diagnosis of predisposition to disorders related to voltage gated calcium channels. The invention also relates to the therapy of disorders related to voltage gated calcium channels including gene therapy, protein replacement therapy and protein mimetics. The invention further relates to the screening of drugs for disorders related to voltage gated calcium channels.

BACKGROUND ART

Voltage-gated calcium channels are a major route of calcium translocation across the plasma membrane of excitable cells. These channels are also known as voltage-dependent calcium channels or VDCCs. Six types of calcium channels have been identified: T, L, N, P, Q, and R. Each channel has different voltage ranges and rates for activation and inactivation. T-type channels need only small depolarizations to be activated (low-voltage activated, LVA), while the other types require larger depolarizations (high-voltage activated, HVA).

Voltage-gated calcium channels are made up of subunits $\alpha_1$, $\beta$ $\alpha_2$, $\delta$. Of these the $\alpha_1$ subunit is the ion pore forming subunit to which the other subunits are auxiliary. β-subunits play an important role in the $Ca^{2+}$ channel trafficking to the cell surface and modulate its biophysical properties. β-subunits have been found to affect all aspects of pore function including rates of voltage activation and deactivation. Among the β-subunit encoding genes, P/Q-type $Ca_v2.1$ and N-type $Ca_v2.2$ are the main channel subtypes on the presynaptic site and thus support neurotransmitter release. Four isoforms of the cytoplasmic β-subunit with a number of splice variants have been identified (β1, β2, β3 and β4). These isoforms show different tissue expression and subcellular localisation and have been correlated to associate with the different types of Voltage-gated calcium channels.

Intracellular calcium plays an important role in many biological processes such as calcium dependant neurotransmitter release, hormone secretion, muscle contraction and gene expression. More specifically, it is documented that abnormal levels of intracellular calcium create an imbalance in calcium homeostasis in a variety of cells, tissues and organs leading to many disorders. Cardiac and neural tissues are thought to be especially sensitive to calcium.

Voltage-gated calcium channels are thought to help control the intracellular flow of calcium. The conversion of the intracellular calcium flow by voltage-gated calcium channels is thought to impact a wide spectrum of biological responses and are implicated in several diseases, including ataxia, migraine, epilepsy, neurodegeneration, hypertension, cardiac disorders and diabetes. Currently there are several Calcium channel blockers used to treat some of these conditions. VGCC is associated with genetic diseases called "calcium channelopathies", which include muscular, neurological and cardiac syndromes. Most of these diseases were attributed to gain and loss of function of $Ca^{2+}$ channel activity. For instance, the familial hemiplegic migraine type 1 is associated with an increase in Cav2.1 current density Compounds such as verapamil, isradipine, nefedipine, dilantizem and 1,4-dihydropine analogs of nefedipine interact with the L-type calcium channel to block calcium translocation and are widely used as antihypertensives, migraine treatment and in the treatment of certain vascular disorders. However, there are reports that therapeutic use of many calcium channel blockers is associated with potentially life-threatening side-effects. These include hypotension, constipation, decrease in insulin secretion leading to diabetes and heart block.

Other calcium channel blockers under development for use in disorders of the central nervous system and as analgesics include toxins that have been isolated from marine snails, scorpions, funnel web and tarantula spiders. The side effects and efficacy of such compounds are as yet unknown.

Only two compounds have been found to act as agonists of voltage gated calcium channels, a dihydropyridine derivative BayK 8644 and Glycerotoxin isolated from sea worms. Despite the anticipated therapeutic effects of these compounds such as stimulating insulin secretion in diabetic and pre-diabetic living beings there has been severe side effects such as dystonic neurobehavioural syndrome, hypertension and arrhythmia during in vivo studies using BayK 8644 resulting in halted development of such compounds.

There is a need for new agonists and antagonists capable of modulating voltage gated calcium channels to treat disorders associated with voltage gated calcium channels.

Dos or downstream of Stk11 kinase is a protein named by the position of its encoding gene in the chromosome 10. Only the C-terminal part of the protein was described and no function was established. Sequences analysis of mouse, rat and human EST clones together with classical library screening revealed a transcript of 3 kb encoding for a protein of 698 amino acids. No functional or structural region was identified.

The present invention seeks to provide novel modulators of voltage gated calcium channels for use in treating disorders related to voltage gated calcium channels.

General

Those skilled in the art will appreciate that the invention described herein is susceptible to variations and modifications other than those specifically described. The invention includes all such variation and modifications. The invention also includes all of the steps, features, formulations and compounds referred to or indicated in the specification, individually or collectively and any and all combinations or any two or more of the steps or features.

Each document, reference, patent application or patent cited in this text is expressly incorporated herein in their entirety by reference, which means that it should be read and considered by the reader as part of this text. That the document, reference, patent application or patent cited in this text is not repeated in this text is merely for reasons of conciseness.

Any manufacturer's instructions, descriptions, product specifications, and product sheets for any products mentioned herein or in any document incorporated by reference herein, are hereby incorporated herein by reference, and may be employed in the practice of the invention.

The present invention is not to be limited in scope by any of the specific embodiments described herein. These embodiments are intended for the purpose of exemplification only. Functionally equivalent products, formulations and methods are clearly within the scope of the invention as described herein.

The invention described herein may include one or more range of values (eg size, concentration etc). A range of values will be understood to include all values within the range, including the values defining the range, and values adjacent to the range which lead to the same or substantially the same outcome as the values immediately adjacent to that value which defines the boundary to the range.

Throughout this specification, unless the context requires otherwise, the word "comprise" or variations such as "comprises" or "comprising", will be understood to imply the inclusion of a stated integer or group of integers but not the exclusion of any other integer or group of integers. It is also noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

Other definitions for selected terms used herein may be found within the detailed description of the invention and apply throughout. Unless otherwise defined, all other scientific and technical terms used herein have the same meaning as commonly understood to one of ordinary skill in the art to which the invention belongs.

SUMMARY OF THE INVENTION

We have identified a novel glycoprotein, referred to herein as Voltage gated calcium channel Beta-subunit anchoring regulator protein (VDCC BARP). We have sequenced mouse rate and human nucleic acid sequences encoding VDCC BARP. We have also identified a wide spectrum of Beta-subunits of all types of voltage gated calcium channels that interact with VDCC BARP. We have shown that the introduction of VDCC BARP results in a reduction in calcium channel activity. We have found that blocking VDCC BARP expression particularly in certain domains results in effective calcium channel activity or partial calcium channel activity.

Accordingly the present invention provides a polynucleotide encoding a VDCC BARP modulator of voltage gated calcium channels or a homologue thereof.

The present invention also provides a polynucleotide selected from:
(a) polynucleotides comprising the nucleotide sequence set out in SEQ ID No. 1, SEQ ID No. 3 or SEQ ID No. 5, or a fragment thereof;
(b) polynucleotides comprising a nucleotide sequence capable of hybridising selectively to the nucleotide sequence set out in SEQ ID No. 1, SEQ ID No. 3 or SEQ ID No. 5, or a fragment thereof.
(c) polynucleotides comprising a polynucleotide sequence which is degenerate as a result of the genetic code to the polynucleotides defined in (a), or (b).
(d) polynucleotides complementary to the polynucleotides of (a) or (b);

The present invention also provides a polypeptide which comprises the sequence set out in SEQ ID Nos. 2, 4 or 6 or a polypeptide substantially homologous thereto, or a fragment of the polypeptide of SEQ ID Nos. 2 or 4. Also provided is a polynucleotide encoding a VDCC BARP polypeptide or a homologue or fragment thereof.

The present invention also provides a vector comprising a polynucleotide of the invention, for example an expression vector comprising a polynucleotide of the invention, operably linked to regulatory sequences capable of directing expression of said polynucleotide in a host cell.

The present invention further provides methods of preparing a polynucleotide of the invention comprising polymerising VDCC BARP nucleotides to yield a sequence comprised of at least 8 consecutive nucleotides of the VDCC BARP gene, preferably at least 15 or 20; and methods of preparing a polypeptide comprising polymerizing amino acids to yield a sequence comprising at least 5 amino acids, preferably at least 8 or 10, encoded within the VDCC BARP gene.

The present invention also provides a means to prepare isolated antibodies, which specifically bind to a polypeptide comprised of at least 5 amino acid residues encoded by the VDCC BARP gene. Thus, in another aspect, the present invention provides an antibody capable of binding specifically a polypeptide of the invention.

The present invention further provides a method for detecting the presence or absence of a polynucleotide of the invention in a biological sample containing nucleic acid which method comprises:
(a) bringing the biological sample into contact with a polynucleotide probe or primer comprising a polynucleotide of the invention under suitable hybridising conditions; and
(b) detecting any duplex formed between the probe or primer and nucleic acid in the sample.

The present invention also provides a method of detecting a polypeptide of the invention present in biological samples which comprises:
(a) providing an antibody of the invention;
(b) incubating a biological sample with said antibody under conditions which allow for the formation of an antibody-antigen complex; and
(c) determining whether an antibody-antigen complex comprising said antibody is formed.

The present invention further provides a polynucleotide, polypeptide and/or antibody of the invention for use in therapy. Also provided is a method of treating a condition characterised by an imbalance in calcium homeostasis which method comprises administering to a patient in need of treatment an effective amount of a polynucleotide, polypeptide or antibody of the invention.

VDCC BARP polypeptides of the invention may also be used in methods of identifying substances capable of affecting VDCC BARP function, such as substances capable of modulating calcium channel activity. A substance identified by these methods may be used in a method of modulating calcium channel activity.

In a particular embodiment, there is provided a method for screening the VDCC BARP gene to identify mutations such as those that cause haploinsufficiency. To detect haploinsufficient VDCC BARP gene mutations, a biological sample is preferably prepared and analysed for a difference between the sequence of the VDCC BARP gene being analysed and the sequence of the wild-type VDCC BARP gene. Mutant VDCC BARP genes can be identified by any of the techniques described herein. The mutant alleles can then be sequenced to identify the specific mutation of the particular mutant allele.

Alternatively, mutant VDCC BARP genes can be identified by detecting mutant (altered) VDCC BARP proteins, using conventional techniques. The mutant genes are then sequenced to identify the specific mutation for each gene. The mutations, especially those that lead to an altered function of the VDCC BARP protein, may then be used for the diagnostic and prognostic methods of the present invention.

The present invention also provides kits for screening patients that might be susceptible to disorders related to voltage gated calcium channels, which ailments are linked to mutations in one or both VDCC BARP alleles, for example a mutation resulting in haploinsufficiency of the VDCC BARP gene, which kits comprise at least a polynucleotide complementary to the portion of the VDCC BARP gene packaged in a suitable container, and instructions for its use to identify the VDCC BARP, which instructions also include a sequence listing of the complete or a substantially complete VDCC BARP gene sequence that is capably of encoding a functional VDCC BARP polypeptide sequence in a patient that is not suffering from the specified ailments.

The present invention also provides kits for screening patients to confirm and or identify that they are afflicted with disorders related to voltage gated calcium channels which ailments are linked to haploinsufficiency of the VDCC BARP gene, which kits comprise at least a polynucleotide complementary to the portion of the VDCC BARP gene packaged in a suitable container, and instructions for its use to identify the VDCC BARP, which instructions also include a sequence listing of the complete or a substantially complete VDCC BARP gene sequence that is capably of encoding a functional VDCC BARP polypeptide sequence in a patient that is not suffering from the specified ailments.

In addition, the present invention provides methods of screening drugs for VDCC BARP gene therapy to identify suitable drugs for restoring or blocking VDCC BARP gene product function.

The present invention also provides the means necessary for production of gene-based therapies directed at VDCC BARP genes in cells. These therapeutic agents may take the form of polynucleotides comprising all or a portion of the VDCC BARP gene placed in appropriate vectors or delivered to target cells in more direct ways such that the function of the VDCC BARP gene protein is reconstituted or blocked. Therapeutic agents may also take the form of polypeptides based on either a portion of, or the entire protein sequence of VDCC BARP gene. These may functionally replace the activity of VDCC BARP gene in vivo.

In a further aspect, the present invention provides a method of modulating a voltage gated calcium channel comprising the step of varying the concentration of VDCC BARP polypeptide or varying the concentration of peptide fragments of VDCC BARP polypeptide.

In a further aspect, the present invention provides a composition for modulating a voltage gated calcium channel comprising a VDCC BARP polypeptides, VDCC BARP mutants or VDCC BARP peptide fragments.

Another aspect of the invention provides a system or kit for modulating the activity of calcium channel, the system comprising: a composition comprising a VDCC BARP polypeptide or a peptide fragment of VDCC BARP, and a delivery agent.

The invention has a wide spectrum of useful applications The VDCC BARP gene sequences and proteins described herein may be used in diagnostic/prognostic, therapeutic and drug screening methods described herein for a wide range of species. Further, probes and primers based on the VDCC BARP gene sequences disclosed herein may be used to identify homologous VDCC BARP gene sequences and proteins in other species.

C, C (a) BARP β-interacting domain I (SEQ ID NO:7) includes an AID-like region (SEQ ID NO:11). Comparison of the amino acid residues between BARP domain I and the AID region of α$_1$-subunit is shown. Note the reverse orientation of domain I of BARP. The α-helix area and residues crucial for β-subunits binding are highlighted. C (b) 3-Dimensional Modelling of BARP domain I or AID region with the grove of the β-subunits is depicted. Results of amino acids substitutions in the β-subunits grove or in the AID-like domain I of BARP prevent their respective association as indicated on the model. C (c) Cells were co-transfected with cDNAs for GST-AID or GST-BARP domain I and Flag-Ca$_v$/β$_3$-subunits. GST-proteins that were co-precipitated and associated Ca$_v$/β$_3$ was detected by Western blot using a Flag antibody (a). Corresponding protein expression level of GST-AID and GST-BARP was also detected (b and c). C (d) Domain I of BARP interacts with all β-isoforms. Indeed, β3-subunits were dissociated and recovered in the supernatant after addition of the competitive peptides.

D, D (a) The amino acid sequence of Domain II (SEQ ID NO:8) in BARP, another β-interacting domain is represented. The Amino acids residues involved with β-subunits association are indicated in lighter shading. D (b) Co-precipitation studies identify residues in Domain II involved in β-subunits binding or D (c) shows the isoform specific association.

E, Protein complexes are immunoprecipitated from Flag-ca$_v$β$_3$ (a) or BARP (b) and associated BARP and Ca$_v$β$_3$ revealed by Western blot. The overexpression of these proteins is shown (c and d).

F, immunofluorescence microscopy in PC12 cells using Flag and BARP antibody to label β-subunits and BARP, respectively is depicted. Areas of co-localisation are shown in the merged image. BARP defective in Domain I and II did not relocalized Ca$_v$β$_3$-subunits to the plasma membrane (b-b").

Figure 3A:
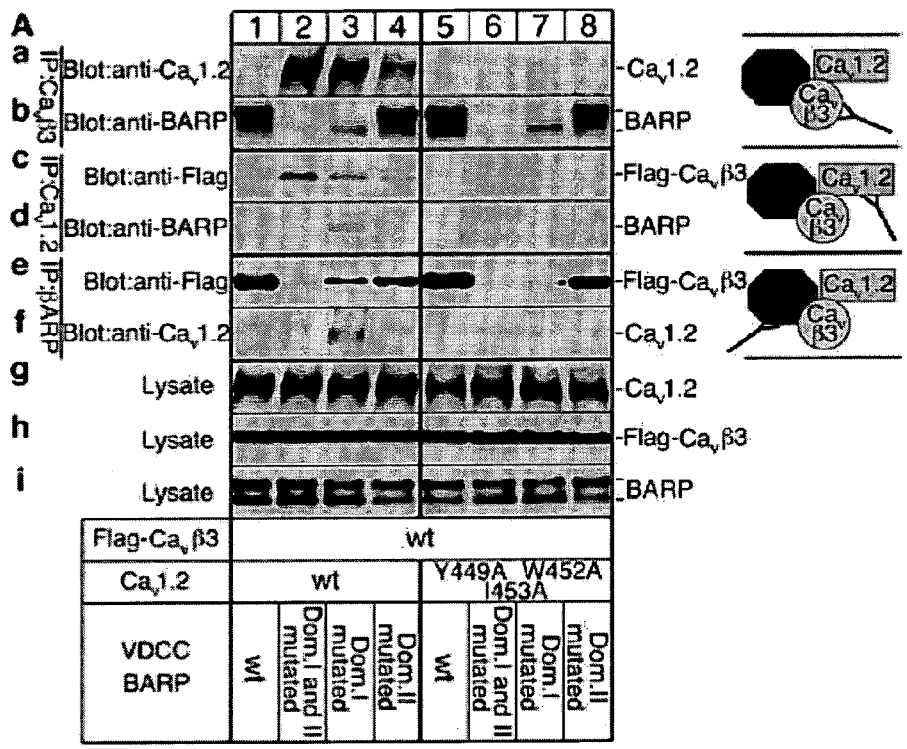
Figure 3B:
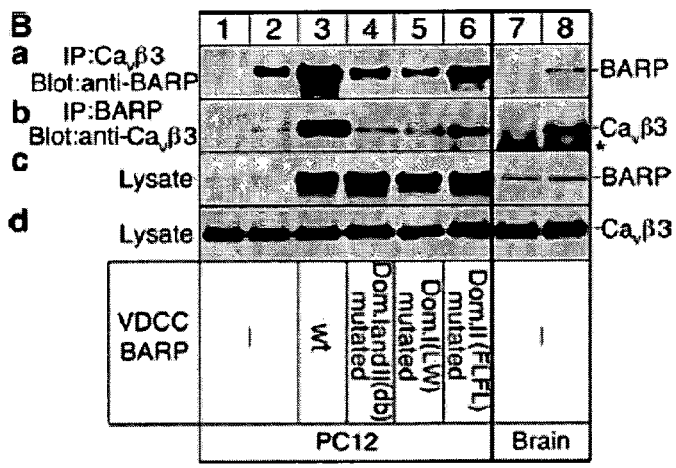
Figure 3C:
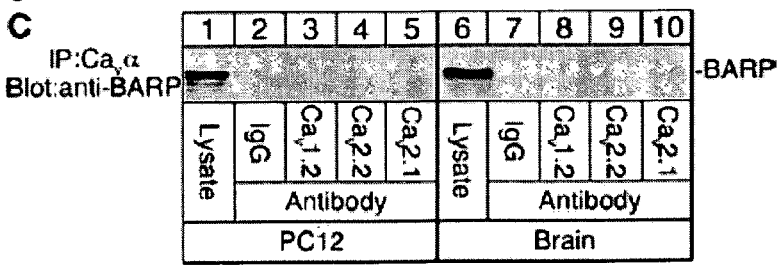

FIG. 3 Association of endogenous or overexpressed BARP with Ca$_v$β- and Ca$_v$1.2-subunits.

A, COS-1 cells were co-transfected with cDNAs for BARP, Flag-Ca$_v$β$_3$- and Ca$_v$1.2-subunits. Ca$_v$β$_3$-(a and b), Ca$_v$1.2-subunits (c and d) and BARP (e and f) were immunoprecipitated and associated Ca$^{2+}$ channel subunits and BARP revealed by western blot using specific antibodies. Protein expression levels are shown in (g) to (i) for Ca$_v$1.2- (g), Flag-Ca$_v$β3- (h) subunits and BARP (i).

B, Endogenous Ca$_v$β3-subunits associate with endogenous or overexpressed BARP. Endogenous Ca$_v$β$_3$-subunits (a) and endogenous (lane 1) or overexpressed (lanes 3-6) BARP (b) were immunoprecipitated from PC12 cells or brain lysate and associated Ca$_v$β$_3$-subunits and BARP revealed by western blot. Protein expression level of BARP (c) and Ca$_v$β3-subunits (d) are shown in (c) and (d). As a control, immunoprecipitation by IgG did not revealed BARP or Ca$_v$β3-subunits association (lane 1 and 7). Asterisk indicates the band for IgG heavy chain.

C, Shows that endogenous BARP weakly associates with Ca$_v$1.2 in PC12 cells and Ca$_v$2.1 in brain tissue. Various subtypes of β$_1$-subunits were immunoprecipitated and associated endogenous BARP detected by western blot.

Figure 4A:
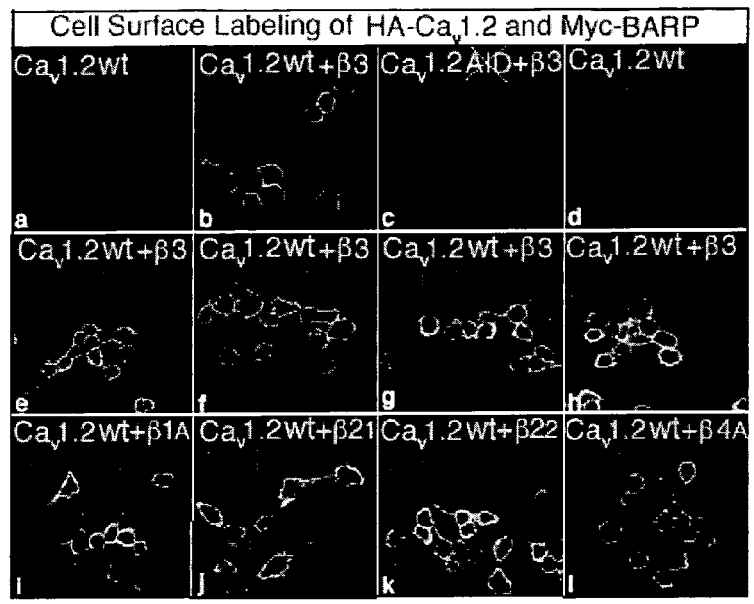
Figure 4B:
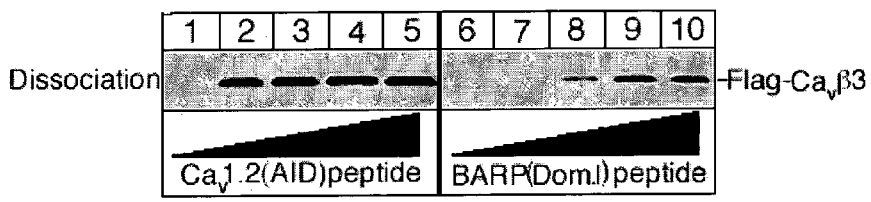

FIG. 4 Overexpression of BARP down regulates Calcium channel activity without affecting channels cell surface expression.

A, Cell surface expression of HA-epitope tagged Ca$_v$1.2 and N-Myc BARP in the presence or absence of Ca$_v$β-subunits. Intact cells expressing Ca$_v$1.2, BARP and Ca$_v$β-subunits were immunostained with HA and Myc antibodies. Ca$_v$ 1.2 AID (X) is a mutant deficient in the β-interacting domain. BARP (db) is a mutant deficient in domain I and II, BARP (LW), or BARP (LFFL), mutants are deficient in domain I and II, respectively. Non-permeabilized TsA201 cells co-expressing wt or mutated HA-Ca$_v$1.2, wt or mutated Myc-BARP and the Ca$_v$β-subunits were immunostained with antibodies to HA (green) and Myc (red). Ca$_v$ 1.2 AID (X) and BARP (db) are mutants defective in Ca$_v$β-subunit binding.

B, BARP displaces the Ca$_v$β3-subunit from the AID. In vivo expressed Ca$_v$β3-subunits were pulled-down using a GST-AID fusion protein and the complex then incubated with increasing amounts of AID or BARP Domain I peptide. The Ca$_v$β3-subunit displaced from the GST-AID was monitored by Western blot.

C, BARP down regulates Ca$^{2+}$-channel activity in BHK cells expressing Ca$_v$2.1 (a) and (b) or Ca$_v$2.2 (c) and (d) together with Ca$_v$β1A and Ca$_v$α2δ. Effects of wt or mutated BARP on the I-V relationship of Ca$^{2+}$-channels are shown. Control versus BARP wt or Domain II mutated (p<0.01); control versus BARP Domain I mutated (p<0.05)

Figure 5:
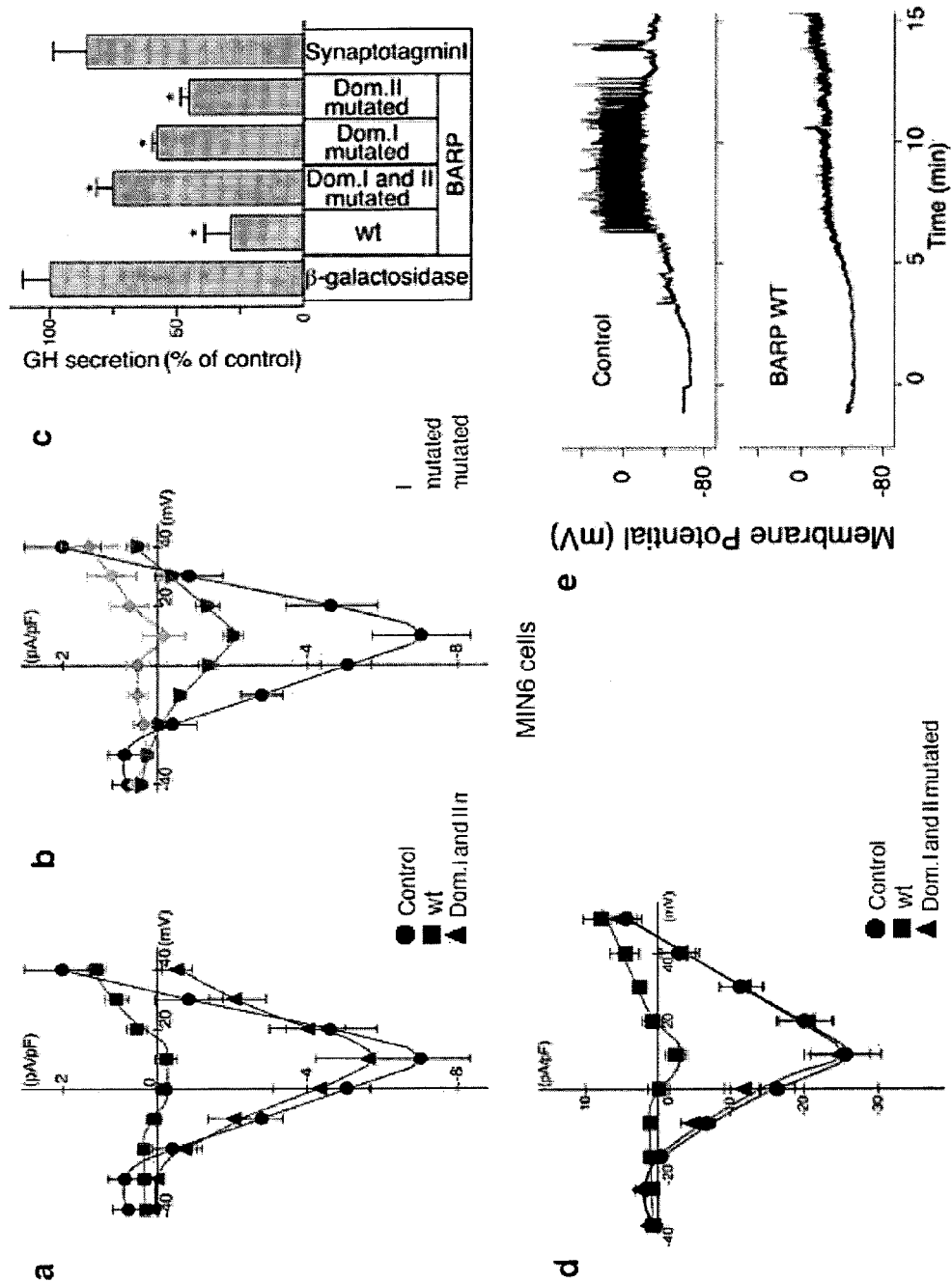

FIG. 5 BARP down-regulates endogenous Ca$^{2+}$-channel activity in PC12 and MIN6 cells.

I-V relationships of endogenous Ca$^{2+}$-channels in PC12 (a and b) and MIN6 (d) cells overexpressing wt or mutated BARP. Effect of BARP on Ca$^{2+}$-triggered GH secretion in PC12 cells (c). Cells were cotransfected with cDNAs for human growth hormone (hGH) and either β-galactosidase (β-gal), Synaptotagmin I (SynI) or BARP. hGH hormone secretion in response to high K$^+$ stimulation from cells co-expressing hGH and β-gal was used as a control (100%). Values (mean±SEM; n=5-14 independent experiments; p<0.05 (*)). Effect of BARP on the glucose-evoked membrane potential (e). MIN6 cells expressing wt BARP were transferred from low (2.8 mM) to high glucose (15 mM) conditions at t=0 min. Representative traces of a typical experiment are shown. MIN6 cells transfected with a cDNA for GFP served as a control.

FIG. 6 Comparison of mouse (SEQ ID No:4), rat (SEQ ID No:2) and human (SEQ ID No:6) sequences where the glycosylation site, the transmembrane domain, Domain I (SEQ ID No:7) and Domain II (SEQ ID No:8) are aligned.

DETAILED DISCLOSURE

Here we report the characterization of a novel glycoprotein (VDCC BARP) that is enriched in synapses with a specific expression in neurons and neuroendocrine cells. This single transmembrane protein interacts by two domains (I and II) directly with the β-subunit, leading to the Ca$^{2+}$ channel down regulation. The reduced channel activities are due to the domain I, which compete for the α/β-subunit binding, while the domain II participates to membrane localization of the BARP/α/β complexes. The Ca$^{2+}$ channel inactivation may not be due to the reduction of channel expression at the cell surface, but rather involved a membrane-delimited inhibition. The presence of BARP anchores the β-subunit to a specific subcellular localisation and modulates the function of voltage gated calcium channels.

The present invention relates to the identification of a nucleic acid sequence, termed herein VDCC BARP, as well as the protein and amino acid sequences, including variations thereof which exhibit modulation of calcium channel activity.

VDCC BARP Polynucleotides

According to the invention there is provided an isolated VDCC BARP nucleic acid molecule which molecule typically encodes a VDCC BARP polypeptide, allelic variant, or analog, including fragments, thereof. Specifically provided are DNA molecules for use in screening for mutations in a VDCC BARP gene and DNA molecules for securing expression of a VDCC BARP polypeptide capable of modulating calcium channel activity in a mammal, and selected from the group consisting of: (a) DNA molecules set out in SEQ ID NOS: 1, 3, 5 or fragments thereof; (b) DNA molecules that hybridize to the DNA molecules defined in (a) or hybridisable fragments thereof; and (c) DNA molecules that code on expression for the amino acid sequence encoded by any of the foregoing DNA molecules.

Preferred DNA molecules according to the invention include DNA molecules comprising the sequence set out in SEQ ID NOS: 1, 3, 5 or fragments thereof.

A polynucleotide is said to "encode" a polypeptide if, in its native state or when manipulated by methods well known to those skilled in the art, it can be transcribed and/or translated to produce the mRNA for and/or the polypeptide or a fragment thereof. The anti-sense strand is the complement of such a nucleic acid, and the encoding sequence can be deduced therefrom.

An "isolated" or "substantially pure" nucleic acid (e.g., an RNA, DNA or a mixed polymer) is one which is substantially separated from other cellular components which naturally accompany a native human sequence or protein, e.g., ribosomes, polymerases, many other human genome sequences and proteins. The term embraces a nucleic acid sequence or protein that has been removed from its naturally occurring environment, and includes recombinant or cloned DNA isolates and chemically synthesized analogs or analogs biologically synthesized by heterologous systems.

"VDCC BARP Allele" refers to normal alleles of the VDCC BARP gene sequence as well as alleles carrying variations that predispose individuals to develop disorders related to calcium channel disfunction. Such predisposing alleles are also called "VDCC BARP susceptibility alleles".

"VDCC BARP gene sequence," "VDCC BARP gene," "VDCC BARP nucleic acids" or "VDCC BARP polynucleotide" each refer to polynucleotides that are likely to be expressed in normal tissue, certain alleles of which predispose an individual to develop disorders related to calcium channel disfunction. Mutations at the VDCC BARP gene sequence may be involved in disruption of calcium homeostasis. The gene sequence is indicated in part by mutations that predispose individuals to develop disorders related to calcium channel disfunction.

The VDCC BARP gene sequence is intended to include coding sequences, intervening sequences and regulatory elements controlling transcription and/or translation. The VDCC BARP gene sequence is intended to include all allelic variations of the DNA sequence.

These terms, when applied to a nucleic acid, refer to a nucleic acid that encodes a VDCC BARP polypeptide, fragment, homologue or variant, including, e.g., protein fusions or deletions. The nucleic acids of the present invention will possess a sequence that is either derived from, or substantially similar to a natural VDCC BARP encoding gene or one having substantial homology with a natural VDCC BARP encoding gene or a portion thereof. The coding sequence for murine VDCC polypeptide is shown in SEQ ID NO: 1, with the amino acid sequence shown in SEQ ID NO: 2. The coding sequence for rodent VDCC BARP polypeptide is shown in SEQ ID NO: 3, with the amino acid sequence shown in SEQ ID NO: 4. The coding sequence for human VDCC BARP polypeptide is shown in SEQ ID NO: 5, with the amino acid sequence shown in SEQ ID NO: 6.

A nucleic acid or fragment thereof is "substantially homologous" ("or substantially similar") to another if, when optimally aligned (with appropriate nucleotide insertions or deletions) with the other nucleic acid (or its complementary strand), there is nucleotide sequence identity in at least about 60% of the nucleotide bases, usually at least about 70%, more usually at least about 80%, preferably at least about 90%, and more preferably at least about 95-98% of the nucleotide bases.

Alternatively, substantial homology or (identity) exists when a nucleic acid or fragment thereof will hybridise to another nucleic acid (or a complementary strand thereof) under selective hybridisation conditions, to a strand, or to its complement. Selectivity of hybridisation exists when hybridisation that is substantially more selective than total lack of specificity occurs. Typically, selective hybridisation will occur when there is at least about 55% identity over a stretch of at least about 14 nucleotides, preferably at least about 65%, more preferably at least about 75%, and most preferably at least about 90%. The length of homology comparison, as described, may be over longer stretches, and in certain embodiments will often be over a stretch of at least about nine nucleotides, usually at least about 20 nucleotides, more usually at least about 24 nucleotides, typically at least about 28 nucleotides, more typically at least about 32 nucleotides, and preferably at least about 36 or more nucleotides.

Thus, polynucleotides of the invention preferably have at least 75%, more preferably at least 85%, more preferably at least 90% homology to the sequences shown in the sequence listings herein. More preferably there is at least 95%, more preferably at least 98%, homology. Nucleotide homology comparisons may be conducted as described below for polypeptides. A preferred sequence comparison program is the GCG Wisconsin Bestfit program described below. The default scoring matrix has a match value of 10 for each identical nucleotide and −9 for each mismatch. The default gap creation penalty is −50 and the default gap extension penalty is −3 for each nucleotide.

In the context of the present invention, a homologous sequence is taken to include a nucleotide sequence which is at least 60, 70, 80 or 90% identical, preferably at least 95 or 98% identical at the amino acid level over at least 20, 50, 100, 200, 300, 500 or 1000 nucleotides with the nucleotides sequences set out in SEQ ID. Nos 1, 3 or 5. In particular, homology should typically be considered with respect to those regions of the sequence that encode contiguous amino acid sequences known to be essential for the function of the protein rather than non-essential neighbouring sequences. Thus, for example, homology comparisons are preferably made over regions corresponding to the transmembrane domain, Domain I, Domain II and/or other domains of the VDCC BARP amino acid sequence set out in SEQ ID NOS: 2, 4 or 6 (see the section on VDCC BARP polypeptides below). Preferred polypeptides of the invention comprise a contiguous sequence having greater than 50, 60 or 70% homology, more preferably greater than 80, 90, 95 or 97% homology, to one or more of the nucleotides sequences of SEQ ID NO: 1 which encode amino acids 41 to 66, 422 to 442 or 525 to 563 of SEQ ID NO:2 or the equivalent nucleotide sequences in SEQ ID NO: 3 or 5. Preferred polynucleotides may alternatively or in addition comprise a contiguous sequence having greater than 80, 90, 95 or 97% homology to the sequence of SEQ ID NO: 1 that encodes amino acids 25 of SEQ ID NO:2 or the corresponding nucleotide sequences of SEQ ID NO: 3 or 5.

Other preferred polynucleotides comprise a contiguous sequence having greater than 40, 50, 60, or 70% homology, more preferably greater than 80, 90, 95 or 97% homology to the sequence of SEQ ID NO: 1 that encodes amino acids 41 to 66, 422 to 442 and/or 525 to 563 of SEQ ID No: 2 or the corresponding nucleotide sequences of SEQ ID NO: 3 or 5.

Nucleotide sequences are preferably at least 15 nucleotides in length, more preferably at least 20, 30, 40, 50, 100 or 200 nucleotides in length.

Generally, the shorter the length of the polynucleotide, the greater the homology required to obtain selective hybridization. Consequently, where a polynucleotide of the invention consists of less than about 30 nucleotides, it is preferred that the % identity is greater than 75%, preferably greater than 90% or 95% compared with the VDCC BARP nucleotide sequences set out in the sequence listings herein. Conversely, where a polynucleotide of the invention consists of, for example, greater than 50 or 100 nucleotides, the % identity compared with the VDCC BARP nucleotide sequences set out in the sequence listings herein may be lower, for example greater than 50%, preferably greater than 60 or 75%.

Nucleic acid hybridisation will be affected by such conditions as salt concentration, temperature, or organic solvents, in addition to the base composition, length of the complementary strands, and the number of nucleotide base mismatches between the hybridizing nucleic acids, as will be readily appreciated by those skilled in the art. Stringent temperature conditions will generally include temperatures in excess of 30 degrees C., typically in excess of 37 degrees C., and preferably in excess of 45 degrees C. Stringent salt conditions will ordinarily be less than 1000 mM, typically less than 500 mM, and preferably less than 200 mM. However, the combination of parameters is much more important than the measure of any single parameter. An example of stringent hybridization conditions is 65° C. and 0.1×SSC (1×SSC=0.15 M NaCl, 0.015 M sodium citrate pH 7.0).

The "polynucleotide" compositions of this invention include RNA, cDNA, genomic DNA, synthetic forms, and mixed polymers, both sense and antisense strands, and may be chemically or biochemically modified or may contain non-natural or derivatized nucleotide bases, as will be readily appreciated by those skilled in the art. Such modifications include, for example, labels, methylation, substitution of one or more of the naturally occurring nucleotides with an analog, internucleotide modifications such as uncharged linkages (e.g., methyl phosphonates, phosphotriesters, phosphoamidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.). Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule.

The present invention provides recombinant nucleic acids comprising all or part of the VDCC BARP region. The recombinant construct may be capable of replicating autonomously in a host cell. Alternatively, the recombinant construct may become integrated into the chromosomal DNA of the host cell. Such a recombinant polynucleotide comprises a polynucleotide of genomic, cDNA, semi-synthetic, or synthetic origin which, by virtue of its origin or manipulation, 1) is not associated with all or a portion of a polynucleotide with which it is associated in nature; 2) is linked to a polynucleotide other than that to which it is linked in nature; or 3) does not occur in nature.

Therefore, recombinant nucleic acids comprising sequences otherwise not naturally occurring are provided by this invention. Although the wild-type sequence may be employed, it will often be altered, e.g., by deletion, substitution or insertion.

A "Recombinant nucleic acid" is a nucleic acid that is not naturally occurring, or which is made by the artificial combination of two otherwise separated segments of sequence. This artificial combination is often accomplished by either chemical syntheses means, or by the artificial manipulation of isolated segments of nucleic acids, by genetic engineering techniques. Such is usually done to replace a codon with a redundant codon encoding the same or a conservative amino acid, while typically introducing or removing a sequence recognition site. Alternatively, it is performed to join together nucleic acid segments of desired functions to generate a desired combination of functions.

cDNA or genomic libraries of various types may be screened as natural sources of the nucleic acids of the present invention, or such nucleic acids may be provided by amplification of sequences resident in genomic DNA or other natural sources, e.g., by PCR. The choice of cDNA libraries normally corresponds to a tissue source that is abundant in mRNA for the desired proteins. Phage libraries are normally preferred, but other types of libraries may be used. Clones of a library are spread onto plates, transferred to a substrate for screening, denatured and probed for the presence of desired sequences.

The nucleic acid sequences used in this invention will usually comprise at least about five codons (15 nucleotides), more usually at least about 7-15 codons, and most preferably, at least about 35 codons. One or more introns may also be present. This number of nucleotides is usually about the minimal length required for a successful probe that would hybridize specifically with a VDCC BARP-encoding sequence.

Techniques for nucleic acid manipulation are described generally, for example, in Sambrook et al., 1989: "Molecular Cloning: a laboratory manual. Sambrook, J., Fritsch, E. F. and Maniatis, T. (1989). Coldspring Harbour Laboratory Press, Coldspring Harbour, N.Y. or Ausubel et al., 1992 Current Protocols in Molecular Biology. Ausubel, F. M., Brent, R., Kingston, R. E., Moore, D. D., Seidman, J. G., Smith, J. G. and Struhl, K. (1987). John Wiley and Sons, NY. Reagents useful in applying such techniques, such as restriction enzymes and the like, are widely known in the art and commercially available from such vendors as New England BioLabs, Boehringer Mannheim, Amersham, Promega Biotec, U.S. Biochemicals, New England Nuclear, and a number of other sources. The recombinant nucleic acid sequences used to produce fusion proteins of the present invention may be derived from natural or synthetic sequences. Many natural gene sequences are obtainable from various cDNA or from genomic libraries using appropriate probes. See, GenBank, National Institutes of Health.

As used herein, the terms "VDCC BARP gene sequence," and "VDCC BARP allele" refer to the double-stranded DNA comprising the gene sequence, allele, or region, as well as either of the single-stranded DNAs comprising the gene sequence, allele or region (i.e. either of the coding and non-coding strands).

As used herein, a "portion" of the VDCC BARP gene sequence or region or allele is defined as having a minimal size of at least about eight nucleotides, or preferably about 15 nucleotides, or more preferably at least about 25 nucleotides, and may have a minimal size of at least about 40 nucleotides. Probe sequences may also hybridize specifically to duplex DNA under certain conditions to form triplex or other higher order DNA complexes. The preparation of such probes and suitable hybridisation conditions are well known in the art.

Detectably labeled nucleic acid molecules hybridisable to a DNA molecule of the invention are also provided and include nucleic acid molecules hybridisable to a non-coding region of a VDCC BARP nucleic acid, which non-coding region is selected from the group consisting of an intron, a 5' non-coding region, and a 3' non-coding region. The present invention also provides oligonucleotide primers for amplifying human genomic DNA encoding a VDCC BARP polypeptide such as oligonucleotides set out in the Examples.

"Probes". Polynucleotide polymorphisms associated with VDCC BARP alleles which predispose to an imbalance of calcium homeostasis are detected by hybridisation with a polynucleotide probe which forms a stable hybrid with that of the target sequence, under stringent to moderately stringent hybridisation and wash conditions. If it is expected that the probes will be perfectly complementary to the target sequence, stringent conditions will be used. Hybridisation stringency may be lessened if some mismatching is expected, for example, if variants are expected with the result that the probe will not be completely complementary. Conditions are chosen which rule out nonspecific/adventitious bindings, that is, which minimize noise. Since such indications identify neutral DNA polymorphisms as well as mutations, these indications need further analysis to demonstrate detection of a VDCC BARP susceptibility allele.

Probes for VDCC BARP alleles may be derived from the sequences of the VDCC BARP region or its cDNAs. The probes may be of any suitable length, which span all or a portion of the VDCC BARP region and which allow specific hybridisation to the VDCC BARP region. If the target sequence contains a sequence identical to that of the probe, the probes may be short, e.g., in the range of about 8-30 base pairs, since the hybrid will be relatively stable under even stringent conditions. If some degree of mismatch is expected with the probe, i.e., if it is suspected that the probe will hybridize to a variant region, a longer probe may be employed which hybridises to the target sequence with the requisite specificity.

The probes will include an isolated polynucleotide attached to a label or reporter molecule and may be used to isolate other polynucleotide sequences, having sequence similarity by standard methods. For techniques for preparing and labeling probes see, e.g Sambrook et al., 1989: "Molecular Cloning: a laboratory manual. Sambrook, J., Fritsch, E. F. and Maniatis, T. (1989). Coldspring Harbour Laboratory Press, Coldspring Harbour, N.Y. or Ausubel et al., 1992 Current Protocols in Molecular Biology. Ausubel, F. M., Brent, R., Kngston, R. E., Moore, D. D., Seidman, J. G., Smith, J. G. and Struhl, K. (1987). John Wiley and Sons, NY. Other similar polynucleotides may be selected by using homologous polynucleotides. Alternatively; polynucleotides encoding these or similar polypeptides may be synthesized or selected by use of the redundancy in the genetic code. Various codon substitutions may be introduced, e.g., by silent changes (thereby producing various restriction sites) or to optimize expression for a particular system. Mutations may be introduced to modify the properties of the polypeptide, perhaps to change ligand-binding affinities, interchain affinities, or the polypeptide degradation or turnover rate.

Probes comprising synthetic oligonucleotides or other polynucleotides of the present invention may be derived from naturally occurring or recombinant single- or double-stranded polynucleotides, or be chemically synthesized. Probes may also be labeled by nick translation, Klenow fill-in reaction, or other methods known in the art.

Portions of the polynucleotide sequence having at least about eight nucleotides, usually at least about 15 nucleotides, and fewer than about 6 kb, usually fewer than about 1.0 kb, from a polynucleotide sequence encoding VDCC BARP are preferred as probes. The probes may also be used to determine whether mRNA encoding VDCC BARP is present in a cell or tissue and whether the genomic organisation of the VDCC BARP locus is deleted or otherwise damaged.

A variety of DNA technologies may thus be used to identify mutant alleles in a range of individuals. A number of these alleles may comprise minor alterations to the genomic sequence, such as point mutations including insertions deletions and/or substitutions. Fragments of nucleic acid which comprise these mutations may be used in diagnostic screening as described below. Accordingly, the present invention provides one or more VDCC BARP polynucleotides or fragments thereof comprising mutations with respect to the wild type sequence, such as the sequence shown in SEQ ID No. 3. In a further embodiment, the present invention provides a plurality of VDCC BARP polynucleotides or fragments thereof for use in screening the DNA of an individual for the presence of one or more mutations/polymorphisms. The plurality of sequences is conveniently provided immobilized to a solid substrate as is described below.

Nucleic Acid Arrays—"DNA Chip" Technology

Polynucleotides of the invention, including probes that may be used to detect both normal (wild type) and abnormal VDCC BARP sequences in nucleic acid samples taken from patients, may be immobilised to a solid phase support. The probes for VDCC BARP will typically form part of a library of DNA molecules that may be used to detect simultaneously a number of different genes in a given genome.

Techniques for producing immobilised libraries of DNA molecules have been described in the art. Generally, most prior art methods describe the synthesis of single-stranded nucleic acid molecule libraries, using for example masking techniques to build up various permutations of sequences at the various discrete positions on the solid substrate. U.S. Pat. No. 5,837,832, the contents of which are incorporated herein by reference, describes an improved method for producing DNA arrays immobilised to silicon substrates based on very large scale integration technology. In particular, U.S. Pat. No. 5,837,832 describes a strategy called "tiling" to synthesize specific sets of probes at spatially-defined locations on a substrate which may be used to produced the immobilised DNA libraries of the present invention. U.S. Pat. No. 5,837,832 also provides references for earlier techniques that may also be used. Thus nucleic acid probes may be synthesised in situ on the surface of the substrate.

Alternatively, single-stranded molecules may be synthesised off the solid substrate and each pre-formed sequence applied to a discrete position on the solid substrate. For example, nucleic acids may be printed directly onto the substrate using robotic devices equipped with either pins or pizo electric devices.

The library sequences are typically immobilised onto or in discrete regions of a solid substrate. The substrate may be porous to allow immobilisation within the substrate or substantially non-porous, in which case the library sequences are typically immobilised on the surface of the substrate. The solid substrate may be made of any material to which polypeptides can bind, either directly or indirectly. Examples of suitable solid substrates include flat glass, silicon wafers, mica, ceramics and organic polymers such as plastics, including polystyrene and polymethacrylate. It may also be possible to use semi-permeable membranes such as nitrocellulose or nylon membranes, which are widely available. The semi-permeable membranes may be mounted on a more robust solid surface such as glass. The surfaces may optionally be coated with a layer of metal, such as gold, platinum or other transition metal. A particular example of a suitable solid substrate is the commercially available BiaCore™ chip (Pharmacia Biosensors).

Preferably, the solid substrate is generally a material having a rigid or semi-rigid surface. In preferred embodiments, at least one surface of the substrate will be substantially flat, although in some embodiments it may be desirable to physically separate synthesis regions for different polymers with, for example, raised regions or etched trenches. It is also preferred that the solid substrate is suitable for the high density application of DNA sequences in discrete areas of typically from 50 to 100 µm, giving a density of 10000 to 40000 $cm^{-2}$.

The solid substrate is conveniently divided up into sections. This may be achieved by techniques such as photoetching, or by the application of hydrophobic inks, for example teflon-based inks (Cel-line, USA).

Discrete positions, in which each different member of the library is located may have any convenient shape, e.g., circular, rectangular, elliptical, wedge-shaped, etc.

Attachment of the nucleic acid sequences to the substrate may be by covalent or non-covalent means. The nucleic acid sequences may be attached to the substrate via a layer of molecules to which the library sequences bind. For example, the nucleic acid sequences may be labelled with biotin and the substrate coated with avidin and/or streptavidin. A convenient feature of using biotinylated nucleic acid sequences is that the efficiency of coupling to the solid substrate can be determined easily. Since the nucleic acid sequences may bind only poorly to some solid substrates, it is often necessary to provide a chemical interface between the solid substrate (such as in the case of glass) and the nucleic acid sequences. Examples of suitable chemical interfaces include hexaethylene glycol. Another example is the use of polylysine coated glass, the polylysine then being chemically modified using standard procedures to introduce an affinity ligand. Other methods for attaching molecules to the surfaces of solid substrate by the use of coupling agents are known in the art see for example WO98/49557.

Binding of complementary nucleic acid sequence to the immobilised nucleic acid library may be determined by a variety of means such as changes in the optical characteristics of the bound nucleic acid (i.e. by the use of ethidium bromide) or by the use of labelled nucleic acids, such as polypeptides labelled with fluorophores. Other detection techniques that do not require the use of labels include optical techniques such as optoacoustics, reflectometry, ellipsometry and surface plasmon resonance (SPR)—see WO97/49989, incorporated herein by reference.

Thus the present invention provides a solid substrate having immobilized thereon at least one polynucleotide of the present invention, preferably two or more different polynucleotides of the present invention, for example two or more different VDCC BARP polynucleotides corresponding to different alleles. In a preferred embodiment the solid substrate further comprises polynucleotides derived from genes other than the VDCC BARP gene.

Preparation of recombinant or chemically synthesised VDCC BARP nucleic acids; vectors, transformation, host cells Any VDCC BARP nucleic acid specimen, in purified or non-purified form, can be utilised as the starting nucleic acid or acids.

PCR is one such process that may be used to amplify VDCC BARP gene sequences. This technique may amplify, for example, DNA or RNA, including messenger RNA, wherein DNA or RNA may be single stranded or double stranded. In the event that RNA is to be used as a template, enzymes, and/or conditions optimal for reverse transcribing the template to DNA would be utilized. In addition, a DNA-RNA hybrid that contains one strand of each may be utilized. A mixture of nucleic acids may also be employed, or the nucleic acids produced in a previous amplification reaction described herein, using the same or different primers may be so utilised.

The specific nucleic acid sequence to be amplified, i.e., the polymorphic gene sequence, may be a fraction of a larger molecule or can be present initially as a discrete molecule, so that the specific sequence constitutes the entire nucleic acid. It is not necessary that the sequence to be amplified is present initially in a pure form; it may be a minor fraction of a complex mixture, such as contained in whole human DNA.

DNA utilized herein may be extracted from a body sample, such as blood, tissue material and the like by a variety of techniques such as that described by Maniatis, et. al. in Molecular Cloning: A Laboratory Manual, Cold Spring Harbor, N.Y., p 280-281, 1982). If the extracted sample has not been purified, it may be treated before amplification with an amount of a reagent effective to open the cells, or animal cell membranes of the sample, and to expose and/or separate the strand(s) of the nucleic acid(s). This lysing and nucleic acid denaturing step to expose and separate the strands will allow amplification to occur much more readily.

The deoxyribonucleotide triphosphates dATP, dCTP, dGTP and dTTP are added to the synthesis mixture, either separately or together with the primers, in adequate amounts and the resulting solution is heated to about 90 degrees-100 degrees C. from about 1 to 10 minutes, preferably from 1 to 4 minutes. After this heating period, the solution is allowed to cool, which is preferable for the primer hybridization. To the cooled mixture is added an appropriate agent for effecting the primer extension reaction (called herein "agent for polymerization"), and the reaction is allowed to occur under conditions known in the art. The agent for polymerization may also be added together with the other reagents if it is heat stable. This synthesis (or amplification) reaction may occur at room temperature up to a temperature above which the agent for polymerization no longer functions. Thus, for example, if DNA polymerase is used as the agent, the temperature is generally no greater than about 40 degree C. Most conveniently the reaction occurs at room temperature.

Allele specific oligonucleotide primers derived from VDCC BARP gene sequence may be useful in determining whether a subject is at risk of suffering from the ailments described herein. Primers direct amplification of a target polynucleotide (eg VDCC BARP) prior to sequencing. Primers used in any diagnostic assays derived from the present invention should be of sufficient length and appropriate sequence to provide initiation of polymerisation. Environmental conditions conducive to synthesis include the presence of nucleoside triphosphates and an agent for polymerisation, such as DNA polymerase, and a suitable temperature and pH.

Primers are preferably single stranded for maximum efficiency in amplification, but may be double stranded. If double stranded, primers may be first treated to separate the strands before being used to prepare extension products. Primers should be sufficiently long to prime the synthesis of VDCC BARP extension products in the presence of the inducing agent for polymerization. The exact length of a primer will depend on many factors, including temperature, buffer, and nucleotide composition. Oligonucleotide primers will typically contain 12-20 or more nucleotides, although they may contain fewer nucleotides.

Primers that may be used in diagnostic assays derived from the present invention should be designed to be substantially complementary to each strand of the VDCC BARP genomic gene sequence. This means that the primers must be sufficiently complementary to hybridise with their respective strands under conditions that allow the agent for polymerisation to perform. In other words, the primers should have sufficient complementarity with the 5' and 3' sequences flanking the mutation to hybridise therewith and permit amplification of the VDCC BARP genomic gene sequence.

Oligonucleotide primers of the invention employed in the PCR amplification process that is an enzymatic chain reaction that produces exponential quantities of VDCC BARP gene sequence relative to the number of reaction steps involved. Typically, one primer will be complementary to the negative (−) strand of the VDCC BARP gene sequence and the other is complementary to the positive (+) strand. Annealing the primers to denatured nucleic acid followed by extension with an enzyme, such as the large fragment of DNA polymerase I (Klenow) and nucleotides, results in newly synthesised + and − strands containing the target a VDCC BARP gene sequence. Because these newly synthesized sequences are also templates, repeated cycles of denaturing, primer annealing, and extension results in exponential production of the region (i.e., the VDCC BARP gene sequence) defined by the primers. The product of the chain reaction is a discreet nucleic acid duplex with termini corresponding to the ends of the specific primers employed.

Oligonucleotide primers may be prepared using any suitable method, such as conventional phosphotriester and phosphodiester methods or automated embodiments thereof. In one such automated embodiment, diethylphosphoramidites are used as starting materials and may be synthesized as described by Beaucage, et al., Tetrahedron Letters, 22:1859-1862, 1981. One method for synthesising oligonucleotides on a modified solid support is described in U.S. Pat. No. 4,458,066.

The agent for polymerisation may be any compound or system which will function to accomplish the synthesis of primer extension products, including enzymes. Suitable enzymes for this purpose include, for example, *E. coli* DNA polymerase I, Klenow fragment of *E. coli* DNA polymerase, polymerase muteins, reverse transcriptase, other enzymes, including heat-stable enzymes (ie, those enzymes which perform primer extension after being subjected to temperatures sufficiently elevated to cause denaturation), such as Taq polymerase. Suitable enzyme will facilitate combination of the nucleotides in the proper manner to form the primer extension products that are complementary to each VDCC BARP gene sequence nucleic acid strand. Generally, the synthesis will be initiated at the 3' end of each primer and proceed in the 5' direction along the template strand, until synthesis terminates, producing molecules of different lengths.

The newly synthesised VDCC BARP strand and its complementary nucleic acid strand will form a double-stranded molecule under hybridizing conditions described above and this hybrid is used in subsequent steps of the process. In the next step, the newly synthesized VDCC BARP double-stranded molecule is subjected to denaturing conditions using any of the procedures described above to provide single-stranded molecules.

The steps of denaturing, annealing, and extension product synthesis can be repeated as often as needed to amplify the target polymorphic gene sequence nucleic acid sequence to the extent necessary for detection. The amount of the specific nucleic acid sequence produced will accumulate in an exponential fashion.

Amplification is described in PCR. A Practical Approach, ILR Press, Eds. M. J. McPherson, P. Quirke, and G. R. Taylor, 1992.

The VDCC BARP amplification products may be detected by Southern blots analysis, without using radioactive probes. In such a process, for example, a small sample of DNA containing a very low level of the nucleic acid sequence of the VDCC BARP gene sequence is amplified, and analyzed via a Southern blotting technique or similarly, using dot blot analysis. The use of non-radioactive probes or labels is facilitated by the high level of the amplified signal. Alternatively, probes used to detect the amplified products can be directly or indirectly detectably labeled, as described herein.

Sequences amplified by the methods of the invention can be further evaluated, detected, cloned, sequenced, and the like, either in solution or after binding to a solid support, by any method usually applied to the detection of a specific DNA sequence such as PCR, oligomer restriction (Saiki, et. al., Bio/Technology, 3:1008-1012, 1985), allele-specific oligonucleotide (ASO) probe analysis (Conner, et. al., Proc. Natl. Acad. Sci. U.S.A., 80:278, 1983), oligonucleotide ligation assays (OLAs) (Landgren, et. al., Science, 241:1007, 1988), and the like. Molecular techniques for DNA analysis have been reviewed (Landgren, et. al., Science, 242:229-237, 1988).

Preferably, the method of amplifying VDCC BARP is by PCR, as described herein and as is commonly used by those of ordinary skill in the art. Alternative methods of amplification have been described and can also be employed as long as the VDCC BARP gene sequence amplified by PCR using primers of the invention is similarly amplified by the alternative means. Such alternative amplification systems include but are not limited to self-sustained sequence replication, which begins with a short sequence of RNA of interest and a T7 promoter. Reverse transcriptase copies the RNA into cDNA and degrades the RNA, followed by reverse transcriptase polymerizing a second strand of DNA. Another nucleic acid amplification technique is nucleic acid sequence-based amplification (NASBA) which uses reverse transcription and T7 RNA polymerase and incorporates two primers to target its cycling scheme. NASBA can begin with either DNA or RNA and finish with either, and amplifies to $10^8$ copies within 60 to 90 minutes. Alternatively, nucleic acid can be amplified by ligation activated transcription (LAT). LAT works from a single-stranded template with a single primer that is partially single-stranded and partially double-stranded. Amplification is initiated by ligating a cDNA to the promoter oligonucleotide and within a few hours, amplification is $10^8$ to $10^9$ fold. The QB replicase system can be utilized by attaching an RNA sequence called MDV-1 to RNA complementary to a DNA sequence of interest. Upon mixing with a sample, the hybrid RNA finds its complement among the specimen's mRNAs and binds, activating the replicase to copy the tag-along sequence of interest. Another nucleic acid amplification technique, ligase chain reaction (LCR), works by using two differently labeled halves of a sequence of interest that are covalently bonded by ligase in the presence of the contiguous sequence in a sample, forming a new target. The repair chain reaction (RCR) nucleic acid amplification technique uses two complementary and target-specific oligonucleotide probe pairs, thermostable polymerase and ligase, and DNA nucleotides to geometrically amplify targeted sequences. A 2-base gap separates the oligonucleotide probe pairs, and the RCR fills and joins the gap, mimicking normal DNA repair.

Nucleic acid amplification by strand displacement activation (SDA) utilizes a short primer containing a recognition site for hincII with short overhang on the 5' end that binds to target DNA. A DNA polymerase fills in the part of the primer opposite the overhang with sulfur-containing adenine analogs. HincII is added but only cuts the unmodified DNA strand. A DNA polymerase that lacks 5' exonuclease activity enters at the site of the nick and begins to polymerize, displacing the initial primer strand downstream and building a new one which serves as more primer. SDA produces greater than $10^7$-fold amplification in 2 hours at 37 degrees C. Unlike PCR and LCR, SDA does not require instrumented temperature cycling. Another amplification system useful in the method of the invention is the QB Replicase System. Although PCR is the preferred method of amplification if the invention, these other methods can also be used to amplify the VDCC BARP gene sequence as described in the method of the invention.

Large amounts of the polynucleotides of the present invention may also be produced by replication in a suitable host cell. Natural or synthetic polynucleotide fragments coding for a desired fragment will be incorporated into recombinant polynucleotide constructs, usually DNA constructs, capable of introduction into and replication in a prokaryotic or eucaryotic cell. Usually the polynucleotide constructs will be suitable for replication in a unicellular host, such as yeast or bacteria, but may also be intended for introduction to (with and without integration within the genome) cultured mammalian or plant or other eucaryotic cell lines.

A double-stranded fragment may be obtained from the single-stranded product of chemical synthesis either by synthesizing the complementary strand and annealing the strands together under appropriate conditions or by adding the complementary strand using DNA polymerase with an appropriate primer sequence.

Nucleic Acid Constructs and Vectors

Polynucleotides of the invention may be incorporated into a recombinant replicable vector for introduction into a prokaryotic or eucaryotic host. Such vectors may typically comprise a replication system recognized by the host, including the intended polynucleotide fragment encoding the desired polypeptide, and will preferably also include transcription and translational initiation regulatory sequences operably linked to the polypeptide encoding segment. Expression vectors may include, for example, an origin of replication or autonomously replicating sequence (ARS) and expression control sequences, a promoter, an enhancer and necessary processing information sites, such as ribosome-binding sites, RNA splice sites, polyadenylation sites, transcriptional terminator sequences, and mRNA stabilizing sequences. localization signals may also be included where appropriate, whether from a native VDCC BARP protein or from other receptors or from secreted polypeptides of the same or related species, which allow the protein to cross and/or lodge in cell membranes, and thus attain its functional topology. The localization signal may be a myristoylation signal. The localization signals may be used to target the BARP protein or peptide to distinct cellular domains to modulate a subset of VDCC especially where more than one type of β-subunit is expressed in a single cell. Neuronal cells are known to express more than one type of β-subunit in a single cell. Further fusion proteins capable of regulating dimerization such as FKBP may be included in a plasmid to facilitate localized dimerization in the presence of rapamycin or FK506 or any other immunosuppressive drugs that naturally act as dimerizers of FKBP and mTOR. Such vectors may be prepared by means of standard recombinant techniques well known in the art and discussed, for example, in Sambrook et al., 1989 supra or Ausubel et al. 1992 supra.

An appropriate promoter and other necessary vector sequences will be selected so as to be functional in the host, and may include, when appropriate, those naturally associated with VDCC BARP genes. Examples of workable combinations of cell lines and expression vectors are described in Sambrook et al., 1989 or Ausubel et al., 1992. Many useful vectors are known in the art and may be obtained from such vendors as Stratagene, New England Biolabs, Promega Biotech, and others. Promoters such as the trp, lac and phage promoters, tRNA promoters and glycolytic enzyme promoters may be used in prokaryotic hosts. Useful yeast promoters include promoter regions for metallothionein, 3-phosphoglycerate kinase or other glycolytic enzymes such as enolase or glyceraldehyde-3-phosphate dehydrogenase, enzymes responsible for maltose and galactose utilization, and others. Vectors and promoters suitable for use in yeast expression are further described in Hitzeman et al., EP 73,675A. Appropriate non-native mammalian promoters might include the early and late promoters from SV40 or promoters derived from murine Moloney leukemia virus, mouse tumour virus, avian sarcoma viruses, adenovirus II, bovine papilloma virus or polyoma. In addition, the construct may be joined to an amplifiable gene (e.g., DHFR) so that multiple copies of the gene may be made. For appropriate enhancer and other expression control sequences.

While such expression vectors may replicate autonomously, they may also replicate by being inserted into the genome of the host cell, by methods well known in the art.

Expression and cloning vectors will likely contain a selectable marker, a gene encoding a protein necessary for survival or growth of a host cell transformed with the vector. The presence of this gene ensures growth of only those host cells that express the inserts. Typical selection genes encode proteins that a) confer resistance to antibiotics or other toxic substances, e.g. ampicillin, neomycin, methotrexate, etc.; b) complement auxotrophic deficiencies, or c) supply critical nutrients not available from complex media, e.g., the gene encoding D-alanine racemase for *Bacilli*. The choice of the proper selectable marker will depend on the host cell, and appropriate markers for different hosts are well known in the art.

The vectors containing the nucleic acids of interest can be transcribed in vitro, and the resulting RNA introduced into the host cell by well-known methods, e.g., by injection, or the vectors can be introduced directly into host cells by methods well known in the art, which vary depending on the type of cellular host, including electroporation; transfection employing calcium chloride, rubidium chloride, calcium phosphate, DEAE-dextran, or other substances; microprojectile bombardment; lipofection; infection (where the vector is an infectious agent, such as a retroviral genome); and other methods. The introduction of the polynucleotides into the host cell by any method known in the art, including, inter alia, those described above, will be referred to herein as "transformation." The cells into which have been introduced nucleic acids described above are meant to also include the progeny of such cells.

Thus the present invention provides host cells transformed or transfected with a nucleic acid molecule of the invention. Preferred host cells include bacteria, yeast, mammalian cells, plant cells, insect cells, and human cells in tissue culture. Illustratively, such host cells are selected from the group consisting of *E. coli, Pseudomonas, Bacillus, Streptomyces*, yeast, CHO, R1.1, B-W, L-M, COS 1. COS 7, BSC1, BSC40, BMT10, and Sf9 cells.

Large quantities of the nucleic acids and polypeptides of the present invention may be prepared by expressing the VDCC BARP nucleic acids or portions thereof in vectors or other expression vehicles in compatible prokaryotic or eucaryotic host cells. The most commonly used prokaryotic hosts are strains of *Escherichia coli*, although other prokaryotes, such as *Bacillus subtilis* or *Pseudomonas* may also be used.

Also provided are mammalian cells containing a VDCC BARP polypeptide encoding DNA sequence and modified in vitro to permit higher expression of VDCC BARP polypeptide by means of a homologous recombinational event consisting of inserting an expression regulatory sequence in functional proximity to the VDCC BARP polypeptide encoding sequence. The expression regulatory sequence can be an VDCC BARP polypeptide expression or not and can replace a mutant VDCC BARP polypeptide regulatory sequence in the cell.

Thus, the present invention also provides methods for preparing an VDCC BARP polypeptide comprising: (a) culturing a cell as described above under conditions that provide for expression of the VDCC BARP polypeptide; and (b) recovering the expressed VDCC BARP polypeptide. This procedure can also be accompanied by the steps of: (c) chromatographing the polypeptide using any suitable means known in the art; and (d) purifying the polypeptide by for example gel filtration.

Mammalian or other eucaryotic host cells, such as those of yeast, filamentous fungi, plant, insect, or amphibian or avian species, may also be useful for production of the proteins of the present invention. Propagation of mammalian cells in culture is per se well known. Examples of commonly used mammalian host cell lines are VERO and HeLa cells, Chinese hamster ovary (CHO) cells, and WI38, BHK, and COS cell lines, although it will be appreciated by the skilled practitioner that other cell lines may be appropriate, e.g., to provide higher expression, desirable glycosylation patterns, or other features.

Clones are selected by using markers depending on the mode of the vector construction. The marker may be on the same or a different DNA molecule, preferably the same DNA molecule. In procaryotic hosts, the transformant may be selected, e.g., by resistance to ampicillin, tetracycline or other antibiotics. Production of a particular product based on temperature sensitivity may also serve as an appropriate marker.

Procaryotic or eucaryotic cells transformed with the polynucleotides of the present invention will be useful not only for the production of the nucleic acids and polypeptides of the present invention, but also, for example, in studying the VDCC BARP Polypeptides Full length VDCC BARP polypeptides of the present invention have about 700 amino acids, encode a modulator of calcium channel activity in an animal, particularly a mammal, and include allelic variants or homologues. Full length VDCC BARP polypeptides also typically comprise a Transmembrane domain, a domain I, a domain II and a glycosylation site (as defined below). VDCC BARP polypeptides of the invention also include fragments and derivatives of full length VDCC BARP polypeptides, particularly fragments or derivatives having substantially the same biological activity. The polypeptides can be prepared by recombinant or chemical synthetic methods. Presently preferred VDCC BARP polypeptides include those comprising the amino acid sequence of SEQ ID NOS: 2, 4 and 6, or allelic variants or homologues, including fragments, thereof. A particularly preferred polypeptide consists of amino acids 24 to 563 of the amino acid sequence shown as SEQ ID NO: 2 or allelic variants, homologues or fragments, thereof.

The term "polypeptide" refers to a polymer of amino acids and its equivalent and does not refer to a specific length of the product; thus, peptides, oligopeptides and proteins are included within the definition of a polypeptide. This term also does not refer to, or exclude modifications of the polypeptide, for example, glycosylations, acetylations, phosphorylations, and the like. Included within the definition are, for example, polypeptides containing one or more analogs of an amino acid (including, for example, natural amino acids, etc.), polypeptides with substituted linkages as well as other modifications known in the art, both naturally and non-naturally occurring.

In the context of the present invention, a homologous sequence is taken to include an amino acid sequence which is at least 60, 70, 80 or 90% identical, preferably at least 95 or 98% identical at the amino acid level over at least 20, 50, 100, 200, 300 or 400 amino acids with the amino acid sequences set out in SEQ ID. Nos 2, 4 or 6. In particular, homology should typically be considered with respect to those regions of the sequence known to be essential for the function of the protein rather than non-essential neighbouring sequences. Thus, for example, homology comparisons are preferably made over regions corresponding to the transmembrane domain, Domain I, Domain II and/or N glycosylation site of the VDCC BARP amino acid sequence set out in SEQ ID NOS: 2, 4 or 6. The transmembrane domain corresponds to approximately amino acids 41 to 66 of SEQ ID NO:2. The Domain I corresponds to approximately amino acids 422 to 442 of SEQ ID NO: 2. The Domain II corresponds to approximately amino acids 525 to 563 of SEQ ID NO:2. The glycosylation site corresponds to approximately amino acid 25 of SEQ ID NO:2. Preferred polypeptides of the invention comprise a contiguous sequence having greater than 50, 60 or 70% homology, more preferably greater than 80 or 90% homology, to one or more of amino acids 25, 41 to 66, 422 to 442 or 525 to 563 of SEQ ID NO: 2 or the corresponding regions of SEQ ID NO: 4 or 6. Preferred polypeptides may alternatively or in addition comprise a contiguous sequence having greater than 80 or 90% homology, to amino acids 422 to 442 of SEQ ID NO: 2 or the corresponding region of SEQ ID NO: 4 or 6.

Other preferred polypeptides comprise a contiguous sequence having greater than 40, 50, 60, or 70% homology, more preferably greater than 80 or 90% homology to amino acids 25, 41 to 66, 422 to 442, and/or 525 to 563 of SEQ ID No: 2 or the corresponding regions of SEQ ID NO: 4 or 6. Although homology can also be considered in terms of similarity (i.e. amino acid residues having similar chemical properties/functions), in the context of the present invention it is preferred to express homology in terms of sequence identity. The terms "substantial homology" or "substantial identity", when referring to polypeptides, indicate that the polypeptide or protein in question exhibits at least about 70% identity with an entire naturally-occurring protein or a portion thereof, usually at least about 80% identity, and preferably at least about 90 or 95% identity.

Homology comparisons can be conducted by eye, or more usually, with the aid of readily available sequence comparison programs. These commercially available computer programs can calculate % homology between two or more sequences.

Percentage (%) homology may be calculated over contiguous sequences, i.e. one sequence is aligned with the other sequence and each amino acid in one sequence directly compared with the corresponding amino acid in the other sequence, one residue at a time. This is called an "ungapped"

alignment. Typically, such ungapped alignments are performed only over a relatively short number of residues (for example less than 50 contiguous amino acids).

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example when using the GCG Wisconsin Bestfit package (see below) the default gap penalty for amino acid sequences is −12 for a gap and −4 for each extension.

Calculation of maximum % homology therefore firstly requires the production of an optimal alignment, taking into consideration gap penalties. A suitable computer program for carrying out such an alignment is the GCG Wisconsin Bestfit package (University of Wisconsin, U.S.A.; Devereux et al., 1984, Nucleic Acids Research 12:387). Examples of other software that can perform sequence comparisons include, but are not limited to, the BLAST package (see Ausubel et al., 1999 ibid—Chapter 18), FASTA (Atschul et al., 1990, J. Mol. Biol., 403-410) and the GENEWORKS suite of comparison tools. Both BLAST and FASTA are available for offline and online searching (see Ausubel et al., 1999 ibid, pages 7-58 to 7-60). However it is preferred to use the GCG Bestfit program.

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see user manual for further details). It is preferred to use the public default values for the GCG package, or in the case of other software, the default matrix, such as BLOSUM62.

Once the software has produced an optimal alignment, it is possible to calculate % homology, preferably % sequence identity. The software typically does this as part of the sequence comparison and generates a numerical result.

VDCC BARP polypeptide homologues include those having the amino acid sequences, wherein one or more of the amino acids is substituted with another amino acid which substitutions do not substantially alter the biological activity of the molecule. An VDCC BARP polypeptide homologue according to the invention preferably has 80 percent or greater amino acid sequence identity to the human VDCC BARP polypeptide amino acid sequence set out in SEQ ID NO: 6. Examples of VDCC BARP polypeptide homologues within the scope of the invention include the amino acid sequence of SEQ ID NOS: 6 wherein: (a) one or more aspartic acid residues is substituted with glutamic acid; (b) one or more isoleucine residues is substituted with leucine; (c) one or more glycine or valine residues is substituted with alanine; (d) one or more arginine residues is substituted with histidine; or (e) one or more tyrosine or phenylalanine residues is substituted with tryptophan.

"VDCC BARP protein" or "VDCC BARP polypeptide" refers to a protein or polypeptide encoded by the VDCC BARP gene sequence, variants or fragments thereof. Also included are proteins encoded by DNA that hybridize under high or low stringency conditions, to VDCC BARP encoding nucleic acids and closely related polypeptides or proteins retrieved by antisera to the VDCC BARP protein(s).

"Protein modifications or fragments" are provided by the present invention for VDCC BARP polypeptides or fragments thereof which are substantially homologous to primary structural sequence but which include, e.g., in vivo or in vitro chemical and biochemical modifications or which incorporate unusual amino acids. Such modifications include, for example, acetylation, carboxylation, phosphorylation, glycosylation, ubiquitination, labeling, e.g., with radionuclides, and various enzymatic modifications, as will be readily appreciated by those well skilled in the art. A variety of methods for labeling polypeptides and of substituents or labels useful for such purposes are well known in the art, and include radioactive isotopes such as $^{32}P$, ligands which bind to labeled antiligands (e.g., antibodies), fluorophores, chemiluminescent agents, enzymes, and antiligands which can serve as specific binding pair members for a labeled ligand. The choice of label depends on the sensitivity required, ease of conjugation with the primer, stability requirements, and available instrumentation. Methods of labeling polypeptides are well known in the art. See, e.g., Sambrook et al., 1989 supra or Ausubel et al., 1992 supra.

A polypeptide "fragment," "portion" or "segment" is a stretch of amino acid residues of at least about five to seven contiguous amino acids, often at least about seven to nine contiguous amino acids, typically at least about nine to 13 contiguous amino acids and, most preferably, at least about 20 to 30 or more contiguous amino acids.

Preferred polypeptides of the invention have substantially similar function to wild type full length VDCC BARP. Preferred polynucleotides of the invention encode polypeptides having substantially similar function to wild type full length VDCC BARP. "Substantially similar function" refers to the function of a nucleic acid or polypeptide homologue, variant, derivative or fragment of VDCC BARP with reference to the wild-type VDCC BARP nucleic acid or wild-type VDCC BARP polypeptide.

However, non-functional forms of VDCC BARP polypeptides may also be included within the scope of the invention since they may be useful, for example, as antagonists of VDCC BARP function.

In addition to the similarity of function, the modified polypeptide may have other useful properties, such as a longer half-life. The similarity of function (activity) of the modified polypeptide may be substantially the same as the activity of the wild-type VDCC BARP polypeptide. Alternatively, the similarity of function (activity) of the modified polypeptide may be higher than the activity of the wild-type VDCC BARP polypeptide. The function/biological activity of homologues, variant, derivatives or fragments relative to wild type may be determined, for example, by means of biological assays. For example, when administered to PC12 cells, VDCC BARP reduces calcium channel activity, resulting in a reduction in extracellular calcium concentration. Thus one test for VDCC BARP activity is to administer a variant to PC12 cells and determine whether calcium channel activity is inhibited. Preferred homologues, variants and fragments are capable of inhibiting calcium channel activity by a factor of at least 0.5 relative to full length VDCC BARP, preferably by a factor of at least 0.9. Another test, based on the interaction of VDCC BARP with the AID binding domain of β-subunit of a voltage gated calcium channel to determine the extent of binding of a homologue, variant or fragment to the AID binding domain of β-subunit of a voltage gated calcium channel in an in vitro binding assay. Preferred homologues, variants and fragments are capable of binding to the AID binding domain of β-subunit of a voltage gated calcium channel by a factor of at least 0.5 relative to full length VDCC BARP, preferably by a factor of at least 0.9. Suitable in vitro binding assays are well known to skilled persons, such as GST 'pulldown' assays where one component is expressed as a fusion protein linked to glutathione-S-transferase an immobilized on glutathione-sepharose beads.

The modified polypeptide may be synthesised using conventional techniques, or is encoded by a modified nucleic acid and produced using conventional techniques. The modified nucleic acid is prepared by conventional techniques. A nucleic acid with a function substantially similar to the wild-type VDCC BARP gene function produces the modified protein described above.

Besides substantially full-length polypeptides, the present invention provides for biologically active fragments of the polypeptides. Significant biological activities include ligand-binding, such as binding to the AID binding domain of β-subunit of a voltage gated calcium channel or other identified interacting molecules, inhibition of calcium channel activity and other biological activities characteristic of VDCC BARP polypeptides.

The polypeptides of the present invention, if soluble, may be coupled to a solid-phase support, e.g., nitrocellulose, nylon, column packing materials (e.g., Sepharose beads), magnetic beads, glass wool, plastic, metal, polymer gels, cells, or other substrates. Such supports may take the form, for example, of beads, wells, dipsticks, or membranes.

The present invention also provides for fusion polypeptides, comprising VDCC BARP polypeptides and fragments. Homologous polypeptides may be fusions between two or more VDCC BARP polypeptide sequences or between the sequences of VDCC BARP and a related protein. Likewise, heterologous fusions may be constructed which would exhibit a combination of properties or activities of the derivative proteins. For example, ligand-binding or other domains may be "swapped" between different new fusion polypeptides or fragments. Such homologous or heterologous fusion polypeptides may display, for example, altered strength or specificity of binding. Fusion partners include immunoglobulins, bacterial .beta.-galactosidase, trpE, protein A, .beta.-lactamase, alpha amylase, alcohol dehydrogenase and yeast alpha mating factor.

Fusion proteins will typically be made by either recombinant nucleic acid methods, as described below, or may be chemically synthesized.

"Protein purification" refers to various methods for the isolation of the VDCC BARP polypeptides from other biological material, such as from cells transformed with recombinant nucleic acids encoding VDCC BARP, and are well known in the art. For example, such polypeptides may be purified by immuno-affinity chromatography employing, e.g., the antibodies provided by the present invention. Various methods of protein purification are well known in the art.

The terms "isolated", "substantially pure", and "substantially homogeneous" are used interchangeably to describe a protein or polypeptide that has been separated from components that accompany it in its natural state. A monomeric protein is substantially purified when at least about 60 to 75% of a sample exhibits a single polypeptide sequence. A substantially purified protein will typically comprise about 60 to 90% W/W of a protein sample, more usually about 95%, and preferably will be over about 99% pure. Protein purity or homogeneity may be indicated by a number of means well known in the art, such as polyacrylamide gel electrophoresis of a protein sample, followed by visualizing a single polypeptide band upon staining the gel. For certain purposes, higher resolution may be provided by using HPLC or other means well known in the art which are utilized for application.

A VDCC BARP protein is substantially free of naturally associated components when it is separated from the native contaminants that accompany it in its natural state. Thus, a polypeptide that is chemically synthesised or synthesised in a cellular system different from the cell from which it naturally originates will be substantially free from its naturally associated components. A protein may also be rendered substantially free of naturally associated components by isolation, using protein purification techniques well known in the art.

A polypeptide produced as an expression product of an isolated and manipulated genetic sequence is an "isolated polypeptide," as used herein, even if expressed in a homologous cell type. Synthetically made forms or molecules expressed by heterologous cells are inherently isolated molecules.

Diagnosis

The expression of VDCC BARP varies in certain tissue types. This may be due to mutations in VDCC BARP may be implicated in conditions related to calcium channel disfunction. Consequently, establishing the VDCC BARP status of an individual may be a useful diagnostic and/or prognostic tool.

Diagnostic and prognostic methods will generally be conducted using a biological sample obtained from a patient. A "sample" refers to a sample of tissue or fluid suspected of containing an analyte polynucleotide or polypeptide from an individual including, but not limited to, e.g., plasma, serum, spinal fluid, lymph fluid, the external sections of the skin, respiratory, intestinal, and genitourinary tracts, tears, saliva, blood cells, organs, tissue and samples of in vitro cell culture constituents.

According to the diagnostic and prognostic methods of the present invention, alteration of the wild-type VDCC BARP gene sequence may be detected using anyone of the methods described herein. In addition, the diagnostic and prognostic methods can be performed to detect the wild-type VDCC BARP gene sequence and confirm a lack of a predisposition to a disorder related to voltage gated calcium channels at the VDCC BARP gene sequence.

"Alteration of a wild-type gene" encompasses all forms of mutations including deletions, insertions and point mutations in the coding and noncoding regions. Deletions may be of the entire gene or of only a portion of the gene. Point mutations may result in stop codons, frameshift mutations or amino acid substitutions. Somatic mutations are those that occur only in certain tissues, e.g., in pancreatic islets, pituitary, cerebrum, cerebellum or heart cells and are not inherited in the germline. Germline mutations can be found in any of a body's tissues and are inherited. If only a single VDCC BARP allele is somatically mutated, a disorder related to voltage gated calcium channels may be indicated. The finding of VDCC BARP mutations thus provides both diagnostic and prognostic information. A VDCC BARP gene sequence that is not deleted can be screened for other mutations, such as insertions, small deletions, and point mutations.

The predisposition of a patient to disorders related to voltage gated calcium channels, such as ataxia, migraine, epilepsy, neurodegeneration, hypertension, cardiac disorders and diabetes, and other disorders identified herein, can be ascertained by testing any tissue of the patient for mutations of the VDCC BARP gene. For example, a person who has inherited a germline VDCC BARP mutation might be prone to develop the above disorders. Most simply, blood can be drawn and DNA extracted from the cells of the blood. In addition, prenatal diagnosis can be accomplished by testing fetal cells, placental cells or amniotic cells for mutations of the VDCC BARP gene. Alteration of a wild-type VDCC BARP allele, whether, for example, by point mutation or deletion, can be detected by any of the means discussed herein.

To detect the alteration of the wild-type VDCC BARP gene in a tissue, it is helpful to isolate the tissue free from surrounding normal tissues. Means for enriching tissue preparation are known in the art. For example, the tissue may be isolated from paraffin or cryostat sections. Cells may also be separated by flow cytometry.

A rapid preliminary analysis to detect polymorphisms in DNA sequences can be performed by looking at a series of Southern blots of DNA cut with one or more restriction enzymes, preferably with a large number of restriction enzymes. Each blot contains a series of normal individuals and a series of individuals with disorders related to voltage gated calcium channels, or both. Southern blots displaying hybridising fragments (differing in length from control DNA when probed with sequences near or including the VDCC BARP gene sequence) indicate a possible mutation. If restriction enzymes that produce very large restriction fragments are used, then pulsed field gel electrophoresis (PFGE) may also be employed.

Detection of point mutations may also be accomplished by molecular cloning of the VDCC BARP allele(s) and sequencing the allele(s) using techniques well known in the art. Alternatively, the gene sequences can be amplified directly from a genomic DNA preparation from other minor tissue, using known techniques. The most popular method used today is target amplification. Here, the target nucleic acid sequence is amplified with polymerases. One particularly preferred method using polymerase-driven amplification is the polymerase chain reaction (PCR). The polymerase chain reaction and other polymerase-driven amplification assays can achieve over a million-fold increase in copy number through the use of polymerase-driven amplification cycles. Once amplified, the resulting nucleic acid can be sequenced or used as a substrate for DNA probes.

Some other useful diagnostic techniques for detecting the presence of VDCC BARP and or mutations to the gene include, but are not limited to: 1) allele-specific PCR; 2) single stranded conformation analysis (SSCA); 3) denaturing gradient gel electrophoresis (DGGE); 4) RNase protection assays; 5) the use of proteins which recognize nucleotide mismatches, such as the *E. coli* mutS protein; 6) allele-specific oligonucleotides (ASOs); and 7) fluorescent in situ hybridisation (FISH). Other approaches based on the detection of mismatches between the two complementary DNA strands include clamped denaturing gel electrophoresis (CDGE), heteroduplex analysis (HA) and chemical mismatch cleavage (CMC).

For allele-specific PCR, primers are used which hybridize at their 3' ends to a particular VDCC BARP mutation. If the particular VDCC BARP mutation is not present, an amplification product is not observed. Amplification Refractory Mutation System (ARMS) can also be used, as disclosed in European Patent Application Publication No. 0332435. Insertions and deletions of genes can also be detected by cloning, sequencing and amplification. In addition, restriction fragment length polymorphism (RFLP) probes for the gene or surrounding marker genes can be used to score alteration of an allele or an insertion in a polymorphic fragment. Such a method is particularly useful for screening relatives of an affected individual for the presence of the VDCC BARP mutation found in that individual.

SSCA detects a band which migrates differentially because the sequence change causes a difference in single-strand, intramolecular base pairing. This method does not detect all sequence changes, especially if the DNA fragment size is greater than 200 bp, but can be optimized to detect most DNA sequence variation. The reduced detection sensitivity is a disadvantage, but the increased throughput possible with SSCA makes it an attractive, viable alternative to direct sequencing for mutation detection on a research basis. The fragments that have shifted mobility on SSCA gels are then sequenced to determine the exact nature of the DNA sequence variation.

DGGE detects differences in migration rates of mutant sequences compared to wild-type sequences, using a denaturing gradient gel.

In the RNase protection method a labeled riboprobe that is complementary to the human wild-type VDCC BARP gene coding sequence is used. The riboprobe and either mRNA or DNA isolated from the effected tissue are hybridised together and subsequently digested with the enzyme RNase A that is able to detect some mismatches in a duplex RNA structure. If a mismatch is detected by RNase A, it cleaves at the site of the mismatch. Thus, when the annealed RNA preparation is separated on an electrophoretic gel matrix, if a mismatch has been detected and cleaved by RNase A, an RNA product will be seen which is smaller than the full length duplex RNA for the riboprobe and the mRNA or DNA. The riboprobe need not be the full length of the VDCC BARP mRNA or gene but can be a segment of either. If the riboprobe comprises only a segment of the VDCC BARP mRNA or gene, it will be desirable to use a number of these probes to screen the whole mRNA sequence for mismatches.

In similar fashion, DNA probes can be used to detect mismatches, through enzymatic or chemical cleavage. Alternatively, mismatches can be detected by shifts in the electrophoretic mobility of mismatched duplexes relative to matched duplexes. With either riboprobes or DNA probes, the cellular mRNA or DNA that might contain a mutation can be amplified using PCR (see below) before hybridisation.

In the mutS assay, the protein binds only to sequences that contain a nucleotide mismatch in a heteroduplex between mutant and wild-type sequences.

Once a mutation is known, a gene specific detection approach such as allele specific oligonucleotide (ASO) hybridisation can be utilised to rapidly screen large numbers of samples for that same mutation. In an allele-specific oligonucleotide assay, an oligonucleotide is designed which detects a specific sequence which contains a region of the VDCC BARP gene sequence harboring a known mutation, and the assay is performed by detecting the presence or absence of a hybridisation signal. For example, one oligomer may be about 30 nucleotides in length, corresponding to a portion of the VDCC BARP gene sequence possibly in Domain I or Domain II. By use of a battery of such allele-specific probes, PCR amplification products can be screened to identify the presence of a previously identified mutation in the VDCC BARP gene. Hybridisation of allele-specific probes with amplified VDCC BARP sequences can be performed, for example, on a nylon filter. Hybridisation to a particular probe under stringent hybridisation conditions indicates the presence of the same mutation in the tissue with disrupted calcium channel activity as in the allele-specific probe.

In addition to the above methods VDCC BARP genes and mutants thereof may be detected using conventional probe technology. When probes are used to detect the presence of the target sequences (for example, in screening for susceptibility to disorders related to voltage gated calcium channel), the biological sample to be analysed, such as blood or serum, may be treated, if desired, to extract the nucleic acids. The sample nucleic acid may be prepared in various ways to facilitate detection of the target sequence; e.g. denaturation, restriction digestion, electrophoresis or dot blotting. The targeted region of the sample nucleic acid usually must be at least partially single-stranded to form hybrids with the targeting sequence of the probe. If the sequence is naturally single-stranded, denaturation will not be required. However, if the sequence is double-stranded, the sequence will probably need to be denatured. Denaturation can be carried out by various techniques known in the art.

Sample nucleic acid and probe are incubated under conditions that promote stable hybrid formation of the target sequence in the probe with the putative targeted sequence in the sample. The region of the probes that is used to bind to the sample can be made completely complementary to the targeted region of the human chromosomal location for VDCC BARP. Therefore, high stringency conditions are desirable in order to prevent false positives. However, conditions of high stringency may be used only if the probes are complementary to regions of the chromosome that are unique in the genome. The stringency of hybridisation is determined by a number of factors during hybridisation and during the washing procedure, including temperature, ionic strength, base composition, probe length, and concentration of formamide. Under certain circumstances, the formation of higher order hybrids, such as triplexes, quadraplexes, etc., may be desired to provide the means of detecting target sequences.

Detection, if any, of the resulting hybrid is usually accomplished by the use of labeled probes. Alternatively, the probe may be unlabeled, but may be detectable by specific binding with a ligand that is labeled, either directly or indirectly. Suitable labels, and methods for labeling probes and ligands are known in the art, and include, for example, radioactive labels which may be incorporated by known methods (e.g., nick translation, random priming or kinasing), biotin, fluorescent groups, chemiluminescent groups (e.g., dioxetanes, particularly triggered dioxetanes), enzymes, antibodies and the like. Variations of this basic scheme are known in the art, and include those variations that facilitate separation of the hybrids to be detected from extraneous materials and/or that amplify the signal from the labeled moiety.

Two detection methodologies that are particularly effective, work on the principle that a small ligand (such as digoxigenin, biotin, or the like) is attached to a nucleic acid probe capable of specifically binding VDCC BARP. The small ligand is then detected. In one example, the small ligand attached to the nucleic acid probe might be specifically recognized by an antibody-enzyme conjugate. For example, digoxigenin may be attached to the nucleic acid probe. Hybridisation is then detected by an antibody-alkaline phosphatase conjugate that turns over a chemiluminescent substrate. In a second example, the small ligand may be recognized by a second ligand-enzyme conjugate that is capable of specifically complexing to the first ligand. A well-known example is the biotin-avidin type of interactions.

It is also contemplated within the scope of this invention that the nucleic acid probe assays of this invention will employ a cocktail of nucleic acid probes capable of detecting VDCC BARP. Thus, in one example to detect the presence of VDCC BARP in a cell sample, more than one probe complementary to VDCC BARP is employed and in particular the number of different probes is alternatively 2, 3, or 5 different nucleic acid probe sequences. In another example, to detect the presence of mutations in the VDCC BARP gene sequence in a patient, more than one probe complementary to VDCC BARP is employed where the cocktail includes probes capable of binding to the allele-specific mutations identified in populations of patients with alterations in VDCC BARP. In this embodiment, any number of probes can be used, and will preferably include probes corresponding to the major gene mutations identified as predisposing an individual to the cancerous states described herein.

In a highly preferred embodiment, screening techniques based on hybridization to probes, particularly a plurality of probes that correspond to allele-specific mutations use probes immobilized to solid substrates as described above, for example in the form of DNA arrays on silicon substrates (DNA chips).

Alteration of wild-type VDCC BARP genes can also be detected by screening for alteration of wild-type VDCC BARP protein. Such alterations can be determined by amino acid sequence analysis in accordance with conventional techniques. More preferably, antibodies (polyclonal or monoclonal) may be used to detect differences in, or the absence of VDCC BARP proteins or peptides. The antibodies may be prepared as discussed below under the heading "Antibodies". For example, monoclonal antibodies immunoreactive with VDCC BARP can be used to screen a tissue. Lack of cognate antigen may indicate a VDCC BARP mutation, expression or prostranslation deficiency. Antibodies specific for products of mutant alleles could also be used to detect mutant VDCC BARP gene product. Such immunological assays can be done in any convenient format known in the art. These include Western blots, immunohistochemical assays and ELISA assays. Any means for detecting an altered VDCC BARP protein can be used to detect alteration of wild-type VDCC BARP genes. Functional assays, such as protein binding determinations, can be used. In addition, assays can be used which detect VDCC BARP biological function. Finding a mutant VDCC BARP gene product indicates alteration of a wild-type VDCC BARP gene.

In a preferred embodiment of the invention, antibodies will immunoprecipitate VDCC BARP proteins from solution as well as react with VDCC BARP protein on Western or immunoblots of polyacrylamide gels. In another preferred embodiment, antibodies will detect VDCC BARP proteins in paraffin or frozen tissue sections, using immunocytochemical techniques.

Preferred embodiments relating to methods for detecting VDCC BARP or its mutations include enzyme linked immunosorbent assays (ELISA), radioimmunoassays (RIA), immunoradiometric assays (IRMA) and immunoenzymatic assays (IEMA), including sandwich assays using monoclonal and/or polyclonal antibodies.

Antibodies

The present invention also provides labeled and unlabeled monoclonal and polyclonal antibodies specific for VDCC BARP polypeptides of the invention and immortal cell lines that produce a monoclonal antibody of the invention. Antibody preparation according to the invention involves: (a) conjugating an VDCC BARP polypeptide to a carrier protein; (b) immunizing a host animal with the VDCC BARP polypeptide fragment-carrier protein conjugate of step (a) admixed with an adjuvant; and (c) obtaining antibody from the immunized host animal.

According to the invention, VDCC BARP polypeptide produced recombinantly or by chemical synthesis, and fragments or other derivatives or analogs thereof, including fusion proteins, may be used as an immunogen to generate antibodies that recognize the VDCC BARP polypeptide. Such antibodies include but are not limited to polyclonal, monoclonal, chimeric, single chain, Fab fragments, and an Fab expression library.

Thus, the present invention also provides polyclonal and/or monoclonal antibodies and fragments thereof, and immunologic binding equivalents thereof, which are capable of specifically binding to the VDCC BARP polypeptides and fragments thereof or to polynucleotide sequences from the VDCC BARP region, particularly from the VDCC BARP gene sequence or a portion thereof. Such antibodies thus include for example, but are not limited to polyclonal, monoclonal, chimeric, single chain, Fab fragments, and an Fab expression library. Production of antibodies specific for VDCC BARP polypeptides or fragments thereof is described below.

A molecule is "antigenic" when it is capable of specifically interacting with an antigen recognition molecule of the immune system, such as an immunoglobulin (antibody) or T cell antigen receptor. An antigenic polypeptide contains at least about 5, and preferably at least about 10, amino acids. An antigenic portion of a molecule can be that portion that is immunodominant for antibody or T cell receptor recognition, or it can be a portion used to generate an antibody to the molecule by conjugating the antigenic portion to a carrier molecule for immunization. A molecule that is antigenic need not be itself immunogenic, i.e., capable of eliciting an immune response without a carrier.

An "antibody" is any immunoglobulin, including antibodies and fragments thereof, that binds a specific epitope. The term encompasses polyclonal, monoclonal, and chimeric antibodies, the last mentioned described in further detail in U.S. Pat. Nos. 4,816,397 and 4,816,567, as well as antigen binding portions of antibodies, including Fab, F(ab')$_2$ and F(v) (including single chain antibodies). Accordingly, the phrase "antibody molecule" in its various grammatical forms as used herein contemplates both an intact immunoglobulin molecule and an immunologically active portion of an immunoglobulin molecule containing the antibody combining site. An "antibody combining site" is that structural portion of an antibody molecule comprised of heavy and light chain variable and hypervariable regions that specifically binds antigen.

Exemplary antibody molecules are intact immunoglobulin molecules, substantially intact immunoglobulin molecules and those portions of an immunoglobulin molecule that contains the paratope, including those portions known in the art as Fab, Fab', F(ab')$_2$ and F(v), which portions are preferred for use in the therapeutic methods described herein.

Fab and F(ab')$_2$ portions of antibody molecules are prepared by the proteolytic reaction of papain and pepsin, respectively, on substantially intact antibody molecules by methods that are well-known. See for example, U.S. Pat. No. 4,342,566. Fab' antibody molecule portions are also well-known and are produced from F(ab')$_2$ portions followed by reduction of the disulfide bonds linking the two heavy chain portions as with mercaptoethanol, and followed by alkylation of the resulting protein mercaptan with a reagent such as iodoacetamide. An antibody containing intact antibody molecules is preferred herein.

The phrase "monoclonal antibody" in its various grammatical forms refers to an antibody having only one species of antibody combining site capable of immunoreacting with a particular antigen. A monoclonal antibody thus typically displays a single binding affinity for any antigen with which it immunoreacts. A monoclonal antibody may therefore contain an antibody molecule having a plurality of antibody combining sites, each immunospecific for a different antigen; e.g., a bi-specific (chimeric) monoclonal antibody.

The term "adjuvant" refers to a compound or mixture that enhances the immune response to an antigen. An adjuvant can serve as a tissue depot that slowly releases the antigen and also as a lymphoid system activator that non-specifically enhances the immune response [Hood et al., in *Immunology*, p. 384, Second Ed., Benjamin/Cummings, Menlo Park, Calif. (1984)]. Often, a primary challenge with an antigen alone, in the absence of an adjuvant, will fail to elicit a humoral or cellular immune response. Adjuvants include, but are not limited to, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, keyhole limpet hemocyanins, dinitrophenol, and potentially useful human adjuvants such as BCG (*bacille Calmette-Guerin*) and *Corynebacterium parvum*. Preferably, the adjuvant is pharmaceutically acceptable.

Various procedures known in the art may be used for the production of polyclonal antibodies to VDCC BARP polypeptide, or fragment, derivative or analog thereof. For the production of antibody, various host animals can be immunized by injection with the VDCC BARP polypeptide, or a derivative (e.g., fragment or fusion protein) thereof, including but not limited to rabbits, mice, rats, sheep, goats, etc. In one embodiment, the VDCC BARP polypeptide or fragment thereof can be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (*bacille Calmette-Guerin*) and *Corynebacterium parvum*.

For preparation of monoclonal antibodies directed toward the VDCC BARP polypeptide, or fragment, analog, or derivative thereof, any technique that provides for the production of antibody molecules by continuous cell lines in culture may be used. These include but are not limited to the hybridoma technique originally developed by Kohler et al., *Nature*, 256: 495-497 (1975), as well as the trioma technique, the human B-cell hybridoma technique [Kozbor et al., *Immunology Today*, 4:72 (1983)], and the EBV-hybridoma technique to produce human monoclonal antibodies [Cole et al., in *Monoclonal Antibodies and Cancer Therapy*, pp. 77-96, Alan R. Liss, Inc., (1985)]. Immortal, antibody-producing cell lines can be created by techniques other than fusion, such as direct transformation of B lymphocytes with oncogenic DNA, or transfection with Epstein-Barr virus. See, e.g., M. Schreier et al., "Hybridoma Techniques" (1980); Hammerling et al., "Monoclonal Antibodies And T-cell Hybridomas" (1981); Kennett et al., "Monoclonal Antibodies" (1980); see also U.S. Pat. Nos. 4,341,761; 4,399,121; 4,427,783; 4,444,887; 4,451,570; 4,466,917; 4,472,500; 4,491,632; and 4,493,890.

In an additional embodiment of the invention, monoclonal antibodies can be produced in germ-free animals utilizing recent technology (PCT/US90/02545). According to the invention, human antibodies may be used and can be obtained by using human hybridomas [Cote et al., *Proc. Natl. Acad. Sci. USA*, 80:2026-2030 (1983)] or by transforming human B cells with EBV virus in vitro (Cole et al., 1985, supra). In fact, according to the invention, techniques developed for the production of "chimeric antibodies" [Morrison et al., *J. Bacteriol.*, 159-870 (1984); Neuberger et al., *Nature*, 312:604-608 (1984); Takeda et al., *Nature*, 314:452-454 (1985)] by splicing the genes from a mouse antibody molecule specific for an VDCC BARP polypeptide together with genes from a human antibody molecule of appropriate biological activity can be used; such antibodies are within the scope of this invention. Such human or humanized chimeric antibodies are preferred for use in therapy of human diseases or disorders (described infra), since the human or humanized antibodies are much less likely than xenogenic antibodies to induce an immune response, in particular an allergic response, themselves.

According to the invention, techniques described for the production of single chain antibodies (U.S. Pat. No. 4,946,778) can be adapted to produce VDCC BARP polypeptide-specific single chain antibodies. An additional embodiment of the invention utilizes the techniques described for the construction of Fab expression libraries [Huse et al., *Science*, 246:1275-1281 (1989)] to allow rapid and easy identification of monoclonal Fab fragments with the desired specificity for an VDCC BARP polypeptide, or its derivatives, or analogs.

Antibody fragments which contain the idiotype of the antibody molecule can be generated by known techniques. For example, such fragments include but are not limited to: the $F(ab')_2$ fragment which can be produced by pepsin digestion of the antibody molecule; the Fab' fragments which can be generated by reducing the disulfide bridges of the $F(ab')_2$ fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbent assay), "sandwich" immunoassays, immunoradiometric assays, gel diffusion precipitin reactions, immunodiffusion assays, in situ immunoassays (using colloidal gold, enzyme or radioisotope labels, for example), Western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. For example, to select antibodies that recognize a specific epitope of a VDCC BARP polypeptide, one may assay generated hybridomas for a product that binds to an VDCC BARP polypeptide fragment containing such epitope. For selection of an antibody specific to a VDCC BARP polypeptide from a particular species of animal, one can select on the basis of positive binding with VDCC BARP polypeptide expressed by or isolated from cells of that species of animal.

The foregoing antibodies can be used in methods known in the art relating to the localization and activity of the VDCC BARP polypeptide, e.g., for Western blotting, imaging VDCC BARP polypeptide in situ, measuring levels thereof in appropriate physiological samples, etc.

In a specific embodiment, antibodies are developed by immunizing rabbits with synthetic peptides predicted by the protein sequence or with recombinant proteins made using bacterial expression vectors. The choice of synthetic peptides is made after careful analysis of the predicted protein structure, as described above. In particular, peptide sequences between putative cleavage sites are chosen. Synthetic peptides are conjugated to a carrier such as KLH hemocyanin or BSA using carbodiimide and used in Freunds adjuvant to immunize rabbits. In order to prepare recombinant protein, the pGEX vector can be used to express the polypeptide. Alternatively, one can use only hydrophilic domains to generate the fusion protein. The expressed protein will be prepared in quantity and used to immunize rabbits in Freunds adjuvant.

In yet another embodiment, recombinant VDCC BARP polypeptide is used to immunize rabbits, and the polyclonal antibodies are immunopurified prior to further use. The purified antibodies are particularly useful for semi-quantitative assays, particularly for detecting the presence of VDCC BARP polypeptide.

Preferably, the anti-modulator antibody used in the diagnostic and therapeutic methods of this invention is an affinity-purified polyclonal antibody. More preferably, the antibody is a monoclonal antibody (mAb). In addition, it is preferable for the anti-modulator antibody molecules used herein be in the form of Fab, Fab', $F(ab')_2$ or F(v) portions of whole antibody molecules.

Assays

The present invention provides assays that are suitable for identifying substances that bind to VDCC BARP polypeptides (reference to which includes homologues, variants, derivatives and fragments as described above). In addition, assays are provided that are suitable for identifying substances that interfere with VDCC BARP binding to the AID binding domain of β-subunit of a voltage gated calcium channel, for example proteins identified in yeast two-hybrid screens as interacting with VDCC BARP (such as the AID binding domain of β-subunit of a voltage gated calcium channel). Such assays are typically in vitro. Assays are also provided that test the effects of candidate substances identified in preliminary in vitro assays on intact cells in whole cell assays.

Candidate Substances

A substance that modulates calcium channel activity as a result of an interaction with VDCC BARP polypeptides may do so in several ways. It may directly disrupt the binding of VDCC BARP to a β-subunit of a voltage gated calcium channel by, for example, binding to VDCC BARP and masking or altering the site of interaction with the other component. Candidate substances of this type may conveniently be preliminarily screened by in vitro binding assays as, for example, described below and then tested, for example in a whole cell assay as described below. Examples of candidate substances include antibodies which recognise VDCC BARP.

A substance which can bind directly to VDCC BARP may also inhibit calcium channel activity. This can be tested using, for example the whole cells assays described below. Non-functional homologues of VDCC BARP may also be tested for inhibition of VDCC BARP activity since they may compete with VDCC BARP for binding to a β-subunit of a voltage gated calcium channel. Such non-functional homologues may include naturally occurring VDCC BARP mutants and modified VDCC BARP sequences or fragments thereof. In particular, fragments of VDCC BARP which comprise one or more of the transmembrane domain, Domain I, Domain II, glycosylation site or other functional domains that may be used to compete with full length VDCC BARP.

Where modulating a voltage gated calcium channel comprises inhibiting or reducing the calcium current of the voltage gated calcium channel the modulator may comprise VDCC BARP or peptide fragments such as an AID like domain, Domain I, Domain II or a fusion polypeptide of Domain I and Domain II Preferably Domain I is SYRDLWSLRASLELHAATASD (SEQ ID NO:7) roughly corresponding to amino acids 422 to 442 of SEQ ID NO: 2 and homologous amino acid sequences of corresponding SEQ ID NOS: 4 or 6. Preferably a Domain I fragment can interact with a β subunit of a voltage gated calcium channel thereby inhibiting calcium channel activity.

Preferably Domain II roughly corresponds to amino acids 525 to 563 of SEQ ID NO: 2 eg: PRAWPRRPRRDYSIDEKTDALFHEFLRHDPHFDDAPRHR (SEQ ID NO:8) and homologous amino acid fragment sequences of corresponding SEQ ID NOS: 4 or 6. Preferably a Domain II fragment can interact with a β subunit of a voltage gated calcium channel thereby reducing calcium channel activity.

Alternatively, instead of preventing the association of the components directly, the substance may alter the biologically available amount of VDCC BARP. This may be by inhibiting expression of the component, for example at the level of transcription, transcript stability, translation or post-translational stability. An example of such a substance would be antisense RNA or double-stranded interfering RNA sequences which suppresses the amount of VDCC BARP mRNA biosynthesis. In particular, inhibition of VDCC BARP binding to a β-subunit of a voltage gated calcium channel may decrease the amount of available VDCC BARP in a cell.

Suitable candidate substances include peptides, especially of from about 5 to 30 or 10 to 25 amino acids in size, based on the sequence of the various domains of VDCC BARP described above, or variants of such peptides in which one or more residues have been substituted. Peptides from panels of peptides comprising random sequences or sequences which have been varied consistently to provide a maximally diverse panel of peptides may be used.

Where modulating a voltage gated calcium channel comprises opening or enhancing the calcium current of the voltage gated calcium channel the modulator may comprise mutated BARP wherein an AID like domain, or Domain I, Domain II or both Domain I and Domain II are deleted from the BARP protein. Means of knocking out or knocking down BARP may be used including siRNA an RNA interference sequence capable of interfering with BARP gene expression; alternative RNA splicing techniques; posttranslational processing to BARP; inhibition or lysis of glycosylation of BARP may be inhibited with tunicamycin or PNGase F; the level of expression of BARP including both mRNA expression and protein expression; the sub-cellular localisation of BARP; or any mutation of BARP that effects BARP's expression or journey to the membrane.

Suitable candidate substances also include antibody products (for example, monoclonal and polyclonal antibodies, single chain antibodies, chimeric antibodies and CDR-grafted antibodies) which are specific for VDCC BARP. Furthermore, combinatorial libraries, peptide and peptide mimetics, defined chemical entities, oligonucleotides, and natural product libraries may be screened for activity as regulators of VDCC BARP activity. The candidate substances may be used in an initial screen in batches of, for example 10 substances per reaction, and the substances of those batches which show inhibition tested individually. Candidate substances which show activity in in vitro screens such as those described below can then be tested in whole cell systems, such as mammalian cells which will be exposed to the inhibitor and tested for effects on cell growth.

VDCC BARP Binding Assays

One type of assay for identifying substances that bind to VDCC BARP involves contacting a VDCC BARP polypeptide, which is immobilised on a solid support, with a non-immobilised candidate substance determining whether and/or to what extent the VDCC BARP polypeptide and candidate substance bind to each other. Alternatively, the candidate substance may be immobilised and the VDCC BARP polypeptide non-immobilised.

In a preferred assay method, the VDCC BARP polypeptide is immobilised on beads such as agarose beads. Typically this is achieved by expressing the component as a GST-fusion protein in bacteria, yeast or higher eukaryotic cell lines and purifying the GST-fusion protein from crude cell extracts using glutathione-agarose beads. As a control, binding of the candidate substance, which is not a GST-fusion protein, to the immobilised VDCC BARP polypeptide is determined in the absence of the VDCC BARP polypeptide. The binding of the candidate substance to the immobilised VDCC BARP polypeptide is then determined. This type of assay is known in the art as a GST pulldown assay. Again, the candidate substance may be immobilised and the VDCC BARP polypeptide non-immobilised.

Candidate substances are typically added to a final concentration of from 1 to 1000 nmol/ml, more preferably from 1 to 100 nmol/ml. In the case of antibodies, the final concentration used is typically from 100 to 500 μg/ml, more preferably from 200 to 300 μg/ml.

It is also possible to perform this type of assay using different affinity purification systems for immobilising one of the components, for example Ni-NTA agarose and hexahistidine-tagged components.

Binding of the VDCC BARP polypeptide to the candidate substance may be determined by a variety of methods well-known in the art. For example, the non-immobilised component may be labelled (with for example, a radioactive label, an epitope tag or an enzyme-antibody conjugate). Alternatively, binding may be determined by immunological detection techniques. For example, the reaction mixture can be Western blotted and the blot probed with an antibody that detects the non-immobilised component. ELISA techniques may also be used.

Another type of in vitro assay involves determining whether a candidate substance modulates binding of a protein known to interact with VDCC BARP, such as a β-subunit of a voltage gated calcium channel. Such an assay typically comprises contacting VDCC BARP protein with the known interacting protein in the presence or absence of the candidate substance and determining if the candidate substance has an affect on VDCC BARP binding to the known interacting protein.

Whole Cell Assays

Candidate substances may also be tested on whole cells for their effect on cell growth. Preferably the candidate substances have been identified by the above-described in vitro methods. Alternatively, rapid throughput screens for substances capable of inhibiting calcium channel activity of the cell, may be used as a preliminary screen and then used in the in vitro assay described above to confirm that the affect is on VDCC BARP.

The candidate substance, i.e. the test compound, may be administered to the cell in several ways. For example, it may be added directly to the cell culture medium or injected into the cell. Alternatively, in the case of polypeptide candidate substances, the cell may be transfected with a nucleic acid construct which directs expression of the polypeptide in the cell. Preferably, the expression of the polypeptide is under the control of a regulatable promoter.

Typically, an assay to determine the effect of a candidate substance identified by the method of the invention on calcium channel activity comprises administering the candidate substance to a cell and determining whether the substance affects calcium channel activity. Calcium channel activity can be measured by any electrophysiology technique such as standard patch clamp methods known in the art.

The concentration of candidate substances used will typically be such that the final concentration in the cells is similar to that described above for the in vitro assays.

In a preferred embodiment, the candidate substance is administered to the cell together with functional VDCC BARP. Since VDCC BARP has the effect of reducing calcium channel activity, a substance that inhibits VDCC BARP may serve to restore cell growth back to the levels seen in the absence of VDCC BARP. Alternatively, if cell growth is further reduced, then the substance may be an activator of VDCC BARP function.

A candidate substance is typically considered to be an inhibitor of VDCC BARP function if calcium channel activity is increased by at least 10%, preferably at least 20, 30 or 40% relative to the extent of calcium channel activity seen in the presence of VDCC BARP and absence of the candidate substance. By contrast, a candidate substance is typically considered to be an activator of VDCC BARP function if calcium channel activity is further decreased by at least 10%, preferably at least 20, 30 or 40% relative to the extent of calcium channel activity seen in the presence of VDCC BARP and absence of the candidate substance.

Thus, this invention is also particularly useful for screening compounds by using the VDCC BARP polypeptide or binding fragment thereof in any of a variety of drug screening techniques.

The VDCC BARP polypeptide or fragment employed in such a test may either be free in solution, affixed to a solid support, or borne on a cell surface. One method of drug screening utilizes eucaryotic or procaryotic host cells which are stably transformed with recombinant polynucleotides expressing the polypeptide or fragment, preferably in competitive binding assays. Such cells, either in viable or fixed form, can be used for standard binding assays. One may measure, for example, for the formation of complexes between a VDCC BARP polypeptide or fragment and the agent being tested, or examine the degree to which the formation of a complex between a VDCC BARP polypeptide or fragment and a known ligand is interfered with by the agent being tested.

Thus, the present invention provides methods of screening for drugs comprising contacting such an agent with a VDCC BARP polypeptide or fragment thereof and assaying (i) for the presence of a complex between the agent and the VDCC BARP polypeptide or fragment, or (ii) for the presence of a complex between the VDCC BARP polypeptide or fragment and a ligand, by methods well known in the art. In such competitive binding assays the VDCC BARP polypeptide or fragment is typically labeled. Free VDCC BARP polypeptide or fragment is separated from that present in a protein:protein complex, and the amount of free (i.e., uncomplexed) label is a measure of the binding of the agent being tested to VDCC BARP or its interference with VDCC BARP:ligand binding, respectively.

Another technique for drug screening provides high throughput screening for compounds having suitable binding affinity to the VDCC BARP polypeptides and is described in detail in Geysen, PCT published application WO 84/03564, published on Sep. 13, 1984. Briefly stated, large numbers of different small peptide test compounds are synthesised on a solid substrate, such as plastic pins or some other surface. The peptide test compounds are reacted with VDCC BARP polypeptide and washed. Bound VDCC BARP polypeptide is then detected by methods well known in the art.

Purified VDCC BARP can be coated directly onto plates for use in the aforementioned drug screening techniques. However, antibodies to the polypeptide can be used to capture antibodies to immobilize the VDCC BARP polypeptide on the solid phase.

This invention also contemplates the use of competitive drug screening assays in which antibodies capable of specifically binding the VDCC BARP polypeptide compete with a test compound for binding to the VDCC BARP polypeptide or fragments thereof. In this manner, the antibodies can be used to detect the presence of any peptide that shares one or more antigenic determinants of the VDCC BARP polypeptide.

A further technique for drug screening involves the use of host eucaryotic cell lines or cells (such as described above) that have a nonfunctional VDCC BARP gene. In one embodiment Domain I or Domain I and Domain II polynucleotide's are deleted from the VDCC BARP gene. These host cell lines or cells are defective at the VDCC BARP polypeptide level. The host cell lines or cells are grown in the presence of drug compound. The calcium channel activity of the host cells is measured to determine if the compound is capable of regulating the calcium channel activity of VDCC BARP defective cells.

The goal of rational drug design is to produce structural analogs of biologically active polypeptides of interest or of small molecules with which they interact (e.g., agonists, antagonists, inhibitors) in order to fashion drugs which are, for example, more active or stable forms of the polypeptide, or which, e.g., enhance or interfere with the function of a polypeptide in vivo. In one approach, one first determines the three-dimensional structure of a protein of interest (e.g., VDCC BARP polypeptide) or, for example, of the ligand complex, by x-ray crystallography, by computer modeling or most typically, by a combination of approaches. Less often, useful information regarding the structure of a polypeptide may be gained by modeling based on the structure of homologous proteins. An example of rational drug design is the development of HIV protease inhibitors. In addition, peptides (e.g., VDCC BARP polypeptide) are analysed by an alanine scan. In this technique, an amino acid residue is replaced by Ala, and its effect on the peptide's activity is determined. Each of the amino acid residues of the peptide is analysed in this manner to determine the important regions of the peptide.

It is also possible to isolate a target-specific antibody, selected by a functional assay, and then to solve its crystal structure. In principle, this approach yields a pharmacophore upon which subsequent drug design can be based. It is possible to bypass protein crystallography altogether by generating anti-idiotypic antibodies (anti-ids) to a functional, pharmacologically active antibody. As a mirror image of a mirror image, the binding site of the anti-ids would be expected to be an analog of the original receptor. The anti-id could then be used to identify and isolate peptides from banks of chemically or biologically produced peptides or other molecules. Selected peptides would then act as the pharmacophore.

Thus, one may design drugs that have, e.g., improved VDCC BARP polypeptide activity or stability or which act as inhibitors, agonists, antagonists, etc. of VDCC BARP polypeptide activity. By virtue of the availability of cloned VDCC BARP sequences, sufficient amounts of the VDCC BARP polypeptide may be made available to perform such analytical studies as x-ray crystallography. In addition, the knowledge of the VDCC BARP protein sequence provided herein will guide those employing computer modeling techniques in place of, or in addition to x-ray crystallography.

Therapeutic Uses

One aspect of the invention provides a method of modulating a voltage gated calcium channel comprising the step of varying the concentration of VDCC BARP polypeptides or peptide fragments as described above.

A Voltage gated calcium channel may include all types of calcium channels including T, L, N, P, Q, and R. These may include any isoforms of the cytoplasmic β-subunit including splice variants β1, β2, β3 and β4.

Preferably the term modulates refers to the activation, inhibition, delay, repression or interference of the activity of voltage gated calcium channels; More preferably the term modulates refers to antagonism or agonism of a voltage gated calcium channel activity either in vitro or in vivo. Modulation of voltage gated calcium channel activity may be assessed using the methods described in the examples below or by those commonly used in the art such as measuring the calcium current with patch clamp techniques.

One approach is to administer functional proteins or nucleic acids that inhibit calcium channel activity by direct expression of the functional protein to target cells, a procedure termed gene therapy.

Thus the present invention provides a method of reducing or inhibiting calcium channel activity in a cell which method comprises administering to said cell a functional VDCC BARP polypeptide or polynucleotide encoding said polypeptide. Preferably said cell has an intercellular calcium imbalance. The present invention further provides the use of a polypeptide or polynucleotide of the invention, which polypeptide or polynucleotide is, or encode, biologically active VDCC BARP in gene therapy. Also provided is a method of treating a disease characterized by a disorder related to voltage gated calcium channel, such as ataxia, migraine, epilepsy, neurodegeneration, hypertension, cardiac disorders and diabetes, which method comprises administering to said cells a functional VDCC BARP polypeptide or polynucleotide encoding said polypeptide to suppress calcium channel activity in said cells.

Gene Therapy

According to the present invention, a method is also provided of supplying wild-type VDCC BARP function to a cell that carries mutant VDCC BARP alleles. Supplying such a function should suppress calcium imbalance of the recipient cells. VDCC BARP function may be provided either through the use of gene therapy or alternatively it might be provided in the form of protein therapy which therapy is capable of delivering polypeptide over a sustained period of time.

The wild-type VDCC BARP gene or a part of the gene may be introduced into the cell in a vector or as naked DNA such that the gene remains extrachromosomal. In such a situation, the gene will be expressed by the cell from the extrachromosomal location. If a gene fragment is introduced and expressed in a cell deficient in VDCC BARP activity, the gene fragment should encode a part of the VDCC BARP protein that is required for inhibition of calcium channel activity of the cell. More preferred is the situation where the wild-type VDCC BARP gene or a part thereof is introduced into a deficient cell in such a way that it compensates for the endogenous VDCC BARP gene present in the cell. Vectors for introduction of genes both for recombination and for extrachromosomal maintenance are known in the art, and any suitable vector may be used. However, replication-incompetent retroviral vectors have proved safe and effective in recent trials and most of the approved human gene therapy trials to date rely on retroviral vectors. Thus it is preferred to use retroviral vectors, such as lentiviral vectors, comprising a polynucleotide of the invention and capable of expressing a polypeptide of the invention. Other viral vector systems include adenoviral vectors and herpes virus vectors.

Methods for introducing DNA into cells such as electroporation, calcium phosphate co-precipitation and viral transduction are known in the art, and the choice of method is within the competence of the person skilled in the art. A further gene transfer technique that has been approved by the FDA is the transfer of plasmid DNA in liposomes. Suitable liposome compositions include Lipofectin™.

Cells transformed with the wild-type VDCC BARP gene can be used as model systems to study calcium homeostasis and drug treatments that promote such calcium homeostasis.

As generally discussed above, the VDCC BARP gene or fragment, where applicable, may be employed in gene therapy methods in order to increase the amount of the expression products of such genes in target cells. Such gene therapy is particularly appropriate for use in cells, in which the level of VDCC BARP polypeptide is absent or diminished compared to normal cells. It may also be useful to increase the level of expression of a given VDCC BARP gene even in those cells in which the VDCC BARP gene is expressed at a "normal" level, but the gene product is not fully functional.

Gene therapy would be carried out according to generally accepted methods. Cells from a patient's would be first analysed by the diagnostic methods described above, to ascertain the production of VDCC BARP polypeptide in the cells. A virus or plasmid vector (see further details below), containing a copy of the VDCC BARP gene linked to expression control elements and capable of replicating inside the tumour cells, is prepared. Suitable vectors are known, such as disclosed in U.S. Pat. No. 5,252,479 and PCT published application WO 93/07282. The vector is then injected into the patient, either locally at the site of the disorder related to voltage gated calcium channel. If the transfected gene is not permanently incorporated into the genome of each of the targeted cells, the treatment may have to be repeated periodically.

Gene transfer systems known in the art may be useful in the practice of the gene therapy methods of the present invention. These include viral and nonviral transfer methods. A number of viruses have been used as gene transfer vectors, including papovaviruses, e.g., SV40, adenovirus, vaccinia virus, adeno-associated virus, herpesviruses including HSV and EBV, and retroviruses of avian, murine, and human origin. Most human gene therapy protocols have been based on disabled murine retroviruses.

Nonviral gene transfer methods known in the art include chemical techniques such as calcium phosphate co-precipitation; mechanical techniques, for example microinjection; membrane fusion-mediated transfer via liposomes; and direct DNA uptake and receptor-mediated DNA transfer. Viral-mediated gene transfer can be combined with direct in vivo gene transfer using liposome delivery, allowing one to direct the viral vectors to the cells and not into the surrounding cells. Alternatively, the retroviral vector producer cell line can be injected into affected tissue.

In an approach which combines biological and physical gene transfer methods, plasmid DNA of any size is combined with a polylysine-conjugated antibody specific to the adenovirus hexon protein, and the resulting complex is bound to an adenovirus vector. The trimolecular complex is then used to infect cells. The adenovirus vector permits efficient binding, internalization, and degradation of the endosome before the coupled DNA is damaged.

Liposome/DNA complexes have been shown to be capable of mediating direct in vivo gene transfer. While in standard liposome preparations the gene transfer process is nonspecific, localized in vivo uptake and expression have been reported in tumour deposits, for example, following direct in situ administration.

Gene transfer techniques that target DNA directly to affected tissues are preferred. Receptor-mediated gene transfer, for example, is accomplished by the conjugation of DNA (usually in the form of covalently closed supercoiled plasmid) to a protein ligand via polylysine. Ligands are chosen on the basis of the presence of the corresponding ligand receptors on the cell surface of the target cell/tissue type. These ligand-DNA conjugates can be injected directly into the blood if desired and are directed to the target tissue where receptor binding and internalization of the DNA-protein complex occurs. To overcome the problem of intracellular destruction of DNA, coinfection with adenovirus can be included to disrupt endosome function.

Polypeptides that have VDCC BARP activity can also be supplied to cells that are deficient in VDCC BARP polypeptide or the polypeptide is inactive.

Active VDCC BARP molecules can be introduced into cells by microinjection or by use of liposomes, for example. Alternatively, some active molecules may be taken up by cells, actively or by diffusion. Extracellular application of the VDCC BARP gene product may be sufficient to affect calcium channel activity. Supply of molecules with VDCC BARP activity should lead to partial reversal of the effects of an intercellular calcium imbalance. Other molecules with VDCC BARP activity (for example, peptides, drugs or organic compounds) may also be used to effect such a reversal. Modified polypeptides having substantially similar function are also used for protein therapy.

Animals for testing therapeutic agents can be selected after mutagenesis of whole animals or after treatment of germline cells or zygotes. Such treatments include insertion of mutant VDCC BARP alleles, usually from a second animal species, as well as insertion of disrupted homologous genes. Alternatively, the endogenous VDCC BARP gene(s) of the animals may be disrupted by insertion or deletion mutation or other genetic alterations using conventional techniques. After test substances have been administered to the animals. If the test substance prevents or suppresses the calcium channel activity, then the test substance is a candidate therapeutic agent for the treatment of the disorders related to voltage gated calcium channel identified herein. These animal models provide an extremely important testing vehicle for potential therapeutic products.

Therapeutic Compounds

A further aspect of the invention comprises a compound for modulating a voltage gated calcium channel comprising a β subunit anchoring regulator protein or protein mutants or peptide fragments thereof. Disorders related to voltage gated calcium channels including ataxia, migraine, epilepsy, neurodegeneration, hypertension, cardiac disorders and diabetes.

Examples of compounds for antagonistic activity of a voltage gated calcium channel may comprise VDCC BARP, peptide fragments: AID like domain of BARP or variants thereof; Domain I of BARP such as and variants thereof; Domain II of BARP and variants thereof; fusion Sequences comprising Domain I and Domain II. The compounds for antagonising activity of a voltage gated calcium channel may comprise a VDCC BARP protein or variants thereof. Increasing BARP activity or peptide interaction with β-subunit of VDCC in any way including those mentioned above could be used to treat Disorders related to voltage gated calcium channels including ataxia, migraine, epilepsy, neurodegeneration, hypertension and cardiac disorders.

Examples of compounds for agonistic activity of a voltage gated calcium channel may comprise protein mutants of BARP wherein an AID like domain, or Domain I, Domain II or Domain I and Domain II are deleted from the BARP protein, antibodies of VDCC BARP as described above. The compounds for agonistic activity of a voltage gated calcium channel may comprise a compound that reduces the level of expression of VDCC BARP including both mRNA expression and protein expression; or the sub-cellular localisation of BARP to the membrane. Interfering with the binding of BARP to β-subunit of VDCC or down regulating BARP expression in any way including those mentioned above could be used to treat Disorders related to voltage gated calcium channels including diabetes by stimulating insulin secretion.

Compounds identified by the assay methods of the present invention as regulating VDCC BARP function may also be used in therapeutic methods of the present invention. For example, a compound identified as binding to and enhancing VDCC BARP function may be administered to cells exhibiting intracellular calcium imbalance.

Administration

Substances identified or identifiable by the assay methods of the invention may preferably be combined with various components to produce compositions of the invention. Preferably the compositions are combined with a pharmaceutically acceptable carrier or diluent to produce a pharmaceutical composition (which may be for human or animal use). Suitable carriers and diluents include isotonic saline solutions, for example phosphate-buffered saline. The composition of the invention may be administered by direct injection. The composition may be formulated for parenteral, intramuscular, intravenous, subcutaneous, intraocular, oral or transdermal administration. Typically, each substance may be administered at a dose of from 0.01 to 30 mg/kg body weight, preferably from 0.1 to 10 mg/kg, more preferably from 0.1 to 1 mg/kg body weight.

Polynucleotides/vectors encoding polypeptide components (or antisense constructs) for use in therapeutic methods may be administered directly as a naked nucleic acid construct. They may further comprise flanking sequences homologous to the host cell genome. When the polynucleotides/vectors are administered as a naked nucleic acid, the amount of nucleic acid administered may typically be in the range of from 1 µg to 10 mg, preferably from 100 µg to 1 mg. It is particularly preferred to use polynucleotides/vectors that target specific cells, for example by virtue of suitable regulatory constructs or by the use of targeted viral vectors.

Uptake of naked nucleic acid constructs by mammalian cells is enhanced by several known transfection techniques for example those including the use of transfection agents. Example of these agents include cationic agents (for example calcium phosphate and DEAE-dextran) and lipofectants (for example Lipofectam™ and Transfectam™). Typically, nucleic acid constructs are mixed with the transfection agent to produce a composition.

Preferably the polynucleotide or vector according to the invention is combined with a pharmaceutically acceptable carrier or diluent to produce a pharmaceutical composition. Suitable carriers and diluents include isotonic saline solutions, for example phosphate-buffered saline. The composition may be formulated for parenteral, intramuscular, intravenous, subcutaneous, intraocular, oral or transdermal administration.

Another aspect of the invention provides the use of any of the compositions of for modulation of VDCC in treating disorders related to voltage gated calcium channels. Disorders related to voltage gated calcium channels including ataxia, migraine, epilepsy, neurodegeneration, hypertension, cardiac disorders and diabetes.

The amino acid compositions of the invention may be delivered as peptides directly to the tissue where they are required; prepared in a biological scaffold; in a polymer delivery system or as nucleic acids in recombinant vectors capable of expressing the amino acid composition.

Generally, in humans, oral or topical administration of the compositions is the preferred route, being the most convenient. In circumstances where the recipient suffers from a swallowing disorder or from impairment of drug absorption after oral administration, the drug may be administered parenterally, e.g. sublingually or buccally. This is a particularly useful method of delivery for large peptide drugs. Peptides can be more easily absorbed and delivered to the location of action when they are delivered sublingually or buccally. The efficiency can be increased where the peptides are placed in a scaffold that can help maintain the peptide structure and hence activity. The compositions of the invention will normally be administered intravenously, or by any parenteral route, in the form of a pharmaceutical composition comprising the active ingredient, optionally in the form of a non-toxic organic, or inorganic, acid, or base, addition salt, in a pharmaceutically acceptable dosage form. Depending upon the voltage gated calcium channel dependant disorder and patient to be treated, as well as the route of administration, the compositions may be administered at varying doses.

In human therapy, the compositions can be administered alone but will generally be administered in admixture with a suitable pharmaceutical excipient diluent or carrier selected with regard to the intended route of administration and standard pharmaceutical practice.

The compositions of the invention can also be administered parenterally, for example, intravenously, intra-arterially, intraperitoneally, intrathecally, intraventricularly, intrasternally, intracranially, intra-muscularly or subcutaneously, or they may be administered by infusion techniques. They are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral compositions under sterile conditions is readily accomplished by standard pharmaceutical techniques well-known to those skilled in the art.

Compositions suitable for parenteral administration include aqueous and nonaqueous sterile injection solutions which may contain anti-oxidants, buffers, bacteriostats and solutes which render the composition isotonic with the blood of the intended recipient; and aqueous and non-aqueous sterile suspensions which may include suspending agents and thickening agents. The compositions may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets.

The compositions may also be transdermally administered, for example, by the use of a skin patch. In one embodiment preferably the composition may be administered transdermally. Transdermal administration may be via membranes, patches or sheets placed on the patient's skin. The membranes may be designed for slow release application of the composition, which may include admixtures. The membranes may also be designed to have the advantage of a substantially water free composition. The preparation of suitable membrane compositions under sterile conditions is readily accomplished by standard transdermal techniques well-known to those skilled in the art.

In one embodiment the composition comprises a formula suitable for aerosol delivery to a patient. The compositions of the invention can also be administered intranasally or by inhalation and are conveniently delivered in the form of a dry powder inhaler or an aerosol spray presentation from a pressurised container, pump, spray or nebuliser with the use of a suitable propellant, e.g. dichlorodifluoromethane, trichlorofluoromethane, dichlorotetrafluoro-ethane, a hydrofluoroalkane such as 1,1,1,2-tetrafluoroethane (HFA 134A3 or 1,1,1,2,3,3,3-heptafluoropropane (HFA 227EA3), carbon dioxide or other suitable gas in the case of a pressurised aerosol, the dosage unit may be determined by providing a valve to deliver a metered amount. The pressurised container, pump, spray or nebuliser may contain a solution or suspension of the active composition, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of a composition of the invention and a suitable powder base such as lactose or starch.

Aerosol or dry powder compositions are preferably arranged so that each metered dose or "puff" contains at least 1 mg of a composition of the invention for delivery to the patient. It will be appreciated that the overall daily dose with an aerosol will vary from patient to patient, and may be administered in a single dose or, more usually, in divided doses throughout the day.

For example, the compositions of the invention can be administered orally, buccally or sublingually in the form of tablets, capsules, ovules, elixirs, solutions or suspensions, which may contain flavouring or colouring agents, for immediate-, delayed- or controlled-release applications. The preparation of suitable oral compositions under sterile conditions is readily accomplished by standard pharmaceutical techniques well-known to those skilled in the art. The compositions of invention may also be administered via intracavernosal injection. Alternatively, the compositions of the invention can be administered in the form of a suppository or pessary. Compositions may also be administered by the ocular route. For ophthalmic use, the compositions of the invention can be formulated as micronised suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

The invention may further comprise a method for identifying a composition expected to be useful for treating a disorders related to voltage gated calcium channels, the method comprising the steps of: treating a cell overproducing BARP with a test composition; and assessing the effect of the test composition on the activity of calcium channel currents.

The method of the invention may further comprise the steps of providing, synthesising, purifying and/or formulating a composition selected using computer modelling, as known by those in the art; and of assessing whether the composition modulates the activity of BARP. The composition may be formulated for pharmaceutical use, for example for use in in vivo trials in animals or humans.

The routes of administration and dosages described are intended only as a guide since a skilled practitioner will be able to determine readily the optimum route of administration and dosage for any particular patient and condition.

BEST MODE(S) FOR CARRYING OUT THE INVENTION

Further features of the present invention are more fully described in the following non-limiting Examples. It is to be understood, however, that this detailed description is included solely for the purposes of exemplifying the present invention. It should not be understood in any way as a restriction on the broad description of the invention as set out above.

Methods of molecular cloning, immunology and protein chemistry which are not explicitly described in the following examples are reported in the literature and are known by those skilled in the art. General texts that described conventional molecular biology, microbiology, and recombinant DNA techniques within the skill of the art, included, for example: Sambrook et al., Molecular Cloning: A Laboratory Manual, Second Edition, Cold Spring Harbor Laboratory Press, Cold Spring Harbor, N.Y. (1989); Glover ed., DNA Cloning: A Practical Approach, Volumes I and II, MRL Press, Ltd., Oxford, U.K. (1985); and Ausubel, F., Brent, R., Kingston, R. E., Moore, D. D., Seidman, J. G., Smith, J. A., Struhl, K. Current protocols in molecular biology. Greene Publishing Associates/Wiley Intersciences, New York.

Molecular Biology

Figure 1A:
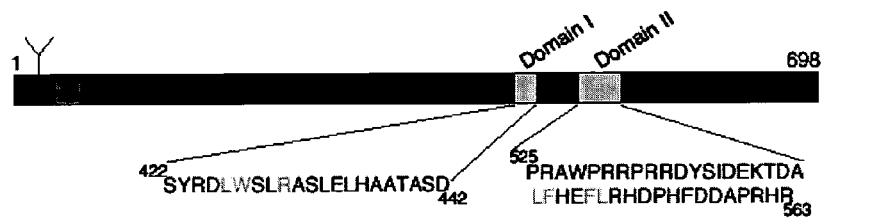
FIG. 1 Characteristics of BARP
A, Structural and functional domains of BARP are represented indicating the N glycosylation site (Y), transmembrane region (dark grey section) and β-interacting domain I (SEQ ID NO:7) and II (SEQ ID NO:8) are depicted (light grey sections). Amino acids sequences of domain I and II with residues involved in β subunits interaction (in lighter shade) are shown.
B, Northern blot of BARP from a range of mouse and human tissues.
C, Western blot of endogenous BARP using rabbit (72) or mouse monoclonal (12B1 and 8B2) antibodies raised against different regions of the protein.
D, Comparison between an in vitro synthesized (odd lanes) and an overexpressed BARP (even lanes) in the various cell lines.
E, BARP is N-glycosylated at position 25. COS-1 cells expressing wild type or BARP mutated at the glycosylation site (amino acid 25) were treated by tunicamycin (10 μg/ml) for 24 h. This treatment produced a reduction in the wild type, but not of the mutant.
F, Cell surface detection of N-myc BARP. COS-1 cells either intact (cell surface labeling) or permeabilized (cell expression) were stained with a Myc antibody. Only the N-terminal of BARP was detected at the cell surface.
G, BARP is expressed in cortex, hippocampus and in Purkinje cells (white arrows). Brain sections were stained with the BARP 12B1 monoclonal antibody and the Hoechst nuclear marker.
H, BARP is expressed in neurons. Primary cells from hippocampus were co-stained with a neuronal (MAP2) or a gliale (GFAP) marker and the BARP 12B1 antibodies (a and b). Alternatively, neurons were stained by the rabbit (72) and mouse (12B1) BARP antibodies (c). Note that 72 antibodies labeled principally the body and the axon of neurons, while 12B1 stained in a punctuated manner the dendrites as well (d).
I, BARP is mainly localized in $Ca^{2+}$-dependent secretory vesicles and migrates to the growth cone after PC12 differentiation. Undifferentiated and NGF-differentiated PC12 cells were co-stained with synaptotagmin, a protein present in the $Ca^{2+}$ sensor vesicles, and BARP 72 antibodies.
Figure 1B:
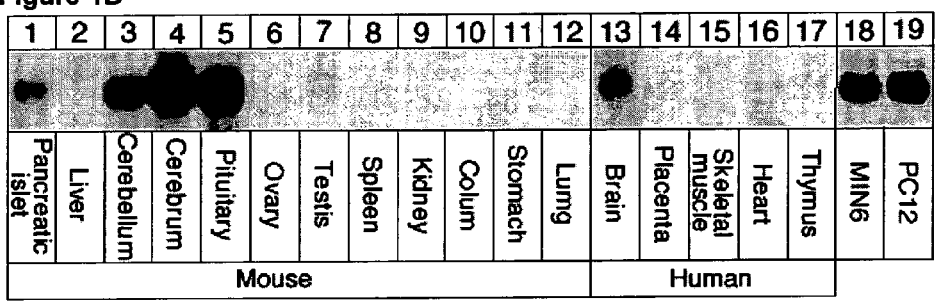
Figure 1C:
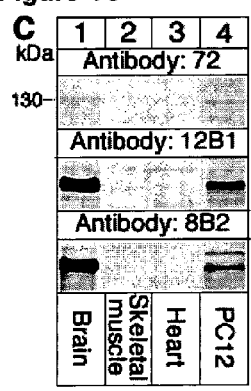

A yeast two-hybrid screen of a complementary DNA library of mouse insulin-secreting MIN6 cells identified Dos (downstream of Stk11 kinase) as an interacting partner of $\beta_3$-subunit. We have renamed the protein as VDCC BARP (VDCC β-subunit anchoring regulator protein). Tissue analysis indicated that BARP messenger RNA is present at high level in brain (cerebellum, cerebrum and pituitary), pancreatic islets and in neuroendocrine cell lines (MIN6 and PC12), but it is weakly expressed in other tissues (FIG. 1B). At the protein level, the presence of BARP in brain and PC12 was confirmed using three antibodies raised against different regions of the BARP protein (FIG. 1C).

The yeast two-hybrid screen of mouse MIN6 cDNA library using the β3-subunit (amino acid residues 50-484) as bait was performed as described. Full length of mouse BARP was identified by conventional screening using a MIN6 and brain cDNA library. Sequences analysis of EST clones from mouse, rat and human (2783848) confirmed that BARP is produced from a transcript of 3 kb. Rat Cavβ1b, Cavβ21 (e.g. β2A), Cavβ3 and Cav1.2 were originally cloned in S. Seino laboratory. Cav 2.1 and Cav 2.2 were a gift from Soon T. W. and Snutch T. P.). Mouse Cav β4A was purchased from I.M.A.G.E. CONSORTIUM™ (I.M.A.G.E. ID 4501980). Cav β specific isoforms and epitope-tagged constructs (FLAG, Myc, GST) were generated by the polymerase chain reaction (PCR)-based method. The HA internal tagged Cav 1.2 was described elsewhere. Northern blot was performed under standard stringent hybridization and washing conditions using a mouse and human BARP cDNA probes.

Sequence Characterisation

Figure 1D:
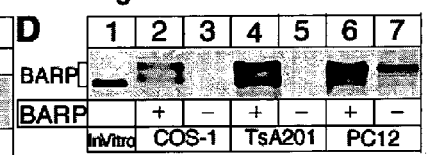

Since the initiation methionine (Met) did not comprise a typical Kozak sequences, we mutated several Met located at the N-terminal of the protein and compare them with the wild type BARP expressed in viva Mutation of Met 1 generated a shorter protein compared to the wild type, confirming that Met 1 is indeed the initiation site. Overexpressed BARP in COS-1 or in HEK derived cell line (TsA201) migrated as a doublet, suggestive of post-translational modifications (FIG. 1D). By comparison with an in vitro synthesized BARP, the molecular mass of the doublet was higher and, in PC12 cells, only the upper band was detected. These indicate that this modification was not a protein cleavage and, in PC12 cells, the processing was fully achieved.

Figure 1E:
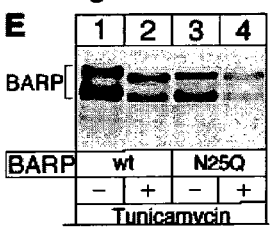

To ascertain that BARP is an N-glycosylated protein, we treated COS-1 cells overexpressing wild type and mutated BARP with tunicamycin, an inhibitor of N-glycosylation. In the mutant, the putative N-glycosylation site (N-X-S/T) was abolished. Consistent with the presence of an N-glycosylation in BARP, tunicamycin treatment produced a reduction in the apparent molecular size of the wild type, but not of the mutant. However, BARP still migrated as a doublet suggesting that additional posttranslational modifications are also involved (FIG. 1E). This result was confirmed by the use of PNGase F, an enzyme that cleaves between the Asparagine and the sugar moiety.

Figure 1F:
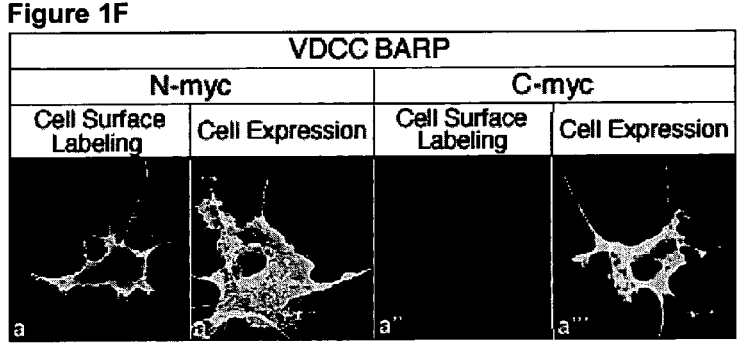

The existence of a glycosylation site at the N-terminus of BARP suggests that this protein is a type I membrane protein, in which the N-terminus is located on the extracytoplasmic side. This assumption was validated by a cell surface labeling experiment using intact COS-1 cells expressing N- or C terminally myc-tagged BARP. As expected, only the N-, but not the C-myc protein was detected at the cell surface (FIG. 1F).

Subcellular Localisation of VDCC BARP

Figure 1G:
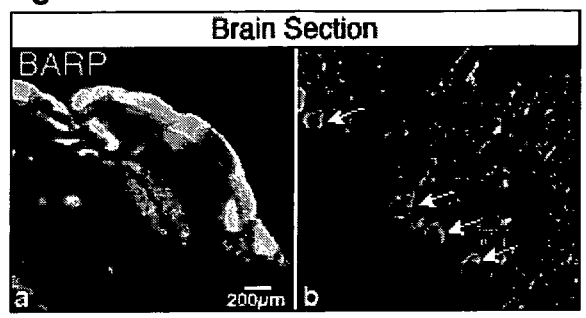
Figure 1H:
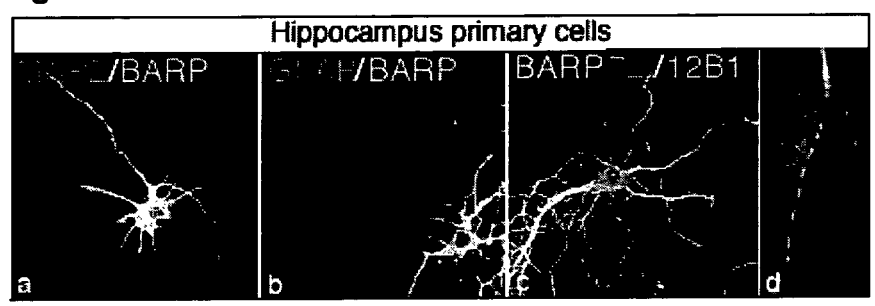
Figure 1I:
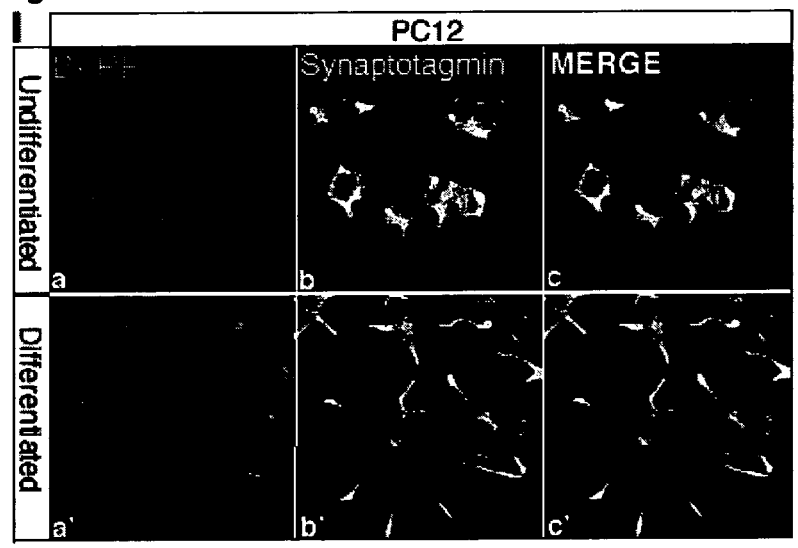

To examine the tissues and subcellular location of BARP, immunolabeling experiments using brain section, primary cells from the hippocampus region and PC12 cells were performed. BARP was found in the cerebellum, mainly in Purkinje cells and along the dendritic tree in a discontinuous staining (FIGS. 1G and 1H, panel d). Co-labeling with specific neuronal (MAP) and gliale (GFAP) marker indicated that BARP was uniquely expressed in neurons (FIG. 1H). In PC12 cells, BARP remarkably co-localized with synaptotagmin I, a $Ca^{2+}$-dependent secretory vesicles marker and similarly migrated to the growth cone after PC12 differentiation (FIG. 1I).

This specific subcellular location of BARP was confirmed by using another vesicular marker chromatogranin. In contrast to the endogenous vesicular staining of these proteins, overexpressed BARP and synaptotagmin I were found at the plasma membrane in PC12 or other cells (see Supplementary Information 1e). This apparent discrepancy was explained for the synaptotagmin family as a transitional plasma membrane location before internalization to reach their final vesicular destination (ref, ref). Altogether, these results demonstrate that BARP is an N-glycosylated protein expressed in neurons and neuroendocrine cells, localizing in the $Ca^{2+}$-sensor vesicles.

Antibody 72 was commercially produced by BIO-GENES™. Rabbits were injected with a BARP peptide (NEAALFEQSRK) conjugated to hemocyanin and antibodies were affinity purified. A GST-BARP fusion protein (amino acids: G125-A698) was injected to mice and mouse monoclonal antibodies produced (12B1 and 8B2). Epitope mapping using truncated form of BARP indicated that 8B2 recognized the C-terminal of BARP, while the 12B1 epitope is localized to the central part of the protein.

VDCC BARP Binding of β-Subunits

Figure 2A:
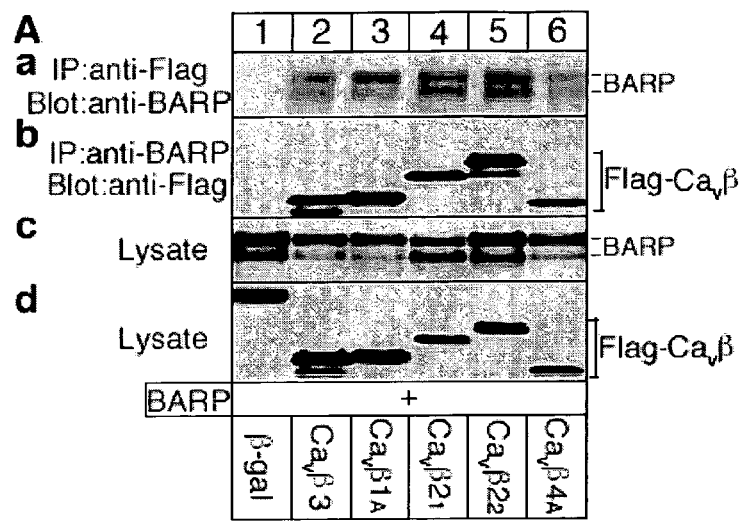
FIG. 2 Association of β-subunits and BARP.
A, Co-immunoprecipitation between β-subunits and BARP. COS-1 cells were transfected with BARP and Flag-tagged β-subunits or Flag-tagged-β-galactosidase cDNAs. Flag-proteins were immunoprecipitated and associated BARP detected by Western blot using a BARP antibody (a). Inverse immunoprecipitation. BARP was immunoprecipitated and Flag-β subunits detected by Western blot (b). Cellular expression level of BARP and Flag-tagged proteins (c and d).
B, BARP anchors β-subunits to the plasma membrane. PC12 cells were transfected with either Flag-β-subunits alone or together with BARP cDNAs. Cells were processed for immunofluorescence microscopy using Flag and BARP antibody to label β-subunits and BARP, respectively. Areas of colocalisation are in the merged image.
Figure 2B:
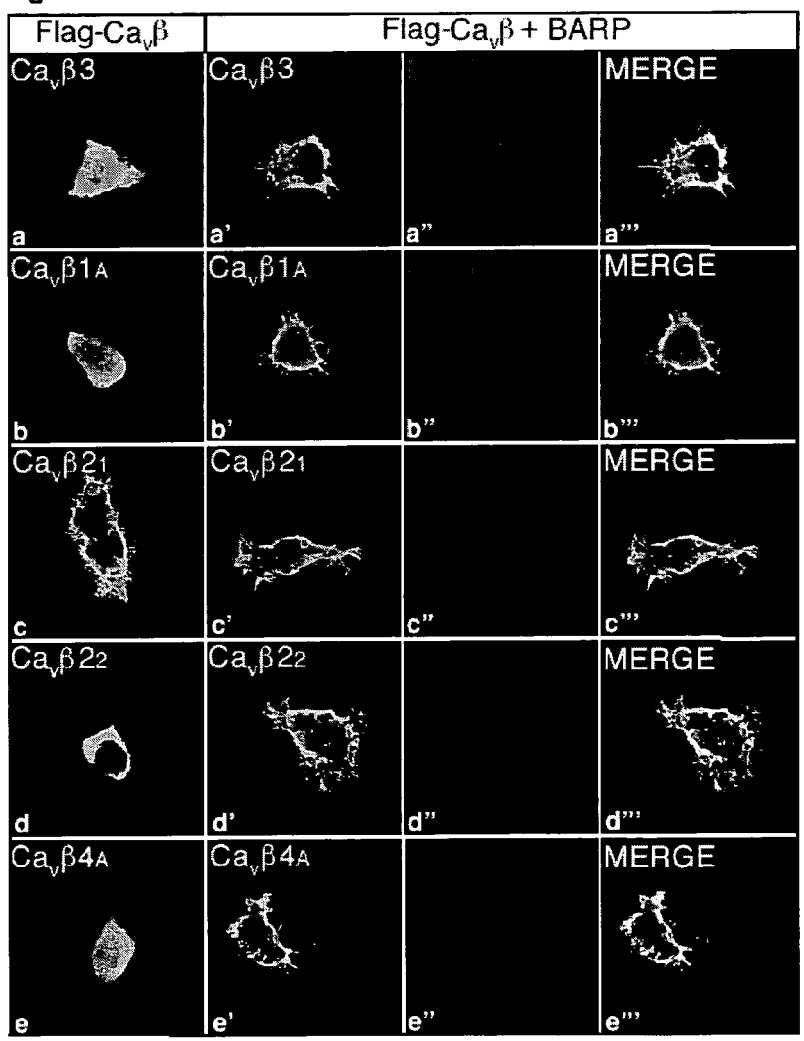

To verify that BARP binds to the β-subunits in mammalian cells, co-immunoprecipitation experiments were carried out in COS-1 cells. Immunoprecipitation from either β-subunits or BARP revealed the presence of the interacting partner in the co-immunoprecipitated protein complex, indicating that BARP associates with all β-isoforms (FIG. 2A). To confirm this association in vivo, we determined the subcellular localization of the β-subunits in the presence of BARP in transfected PC12 and COS-1 cells. Overexpressed β-subunits were found in a diffused ($\beta_3$ and $\beta_{4A}$), cytosolic ($\beta_{1A}$ and $\beta_{22}$) or submembrane ($\beta_{2I}$) location and, remarkably the presence of BARP relocalized the β-subunits to the plasma membrane (FIG. 2B). These results confirmed the in vivo interaction between both proteins and suggest that BARP is an anchoring protein that targets β-subunits to the membrane.

Overexpressed N-FLAG β-subunits and BARP in PC12 and COS1 cells were stained with mouse anti-FLAG (M2; SIGMA™) and rabbit anti-BARP 72 followed by Cy3-labelled donkey anti-rabbit IgG (JACKSON IMMUNORESEARCH LABORATORIES™) and ALEXAFLUOR™ 488 goat anti-mouse IgG (MOLECULAR PROBES™) secondary antibodies as described. In PC12 and hippocampus primary cells, rabbit anti-MAP2 (CHEMICON INTERNATIONAL™), rabbit anti-GFAP (SIGMA™), mouse monoclonal anti-synaptotagmin (STRESSGEN™), and anti-chromatogranin were used to stain endogenous proteins. Cell-surface expression in TsA201 cells were carried out after 24 h after transfection. Cells were washed once with PBS and incubated with 2 μg/ml of rat anti-HA (ROCHE™) and/or 1 μg/ml of rabbit anti-Myc (UPSTATE BIOTECHNOLOGY™) for 1 h at 37 C and then washed twice in ice-cold PBS before fixation. Preparation and tissue of brain section staining was described elsewhere. Specimens were visualized with a confocal microscope (CARL ZEISS™) at 60× magnification.

VDCC BARP Mutations and Fragments

Figure 2C:
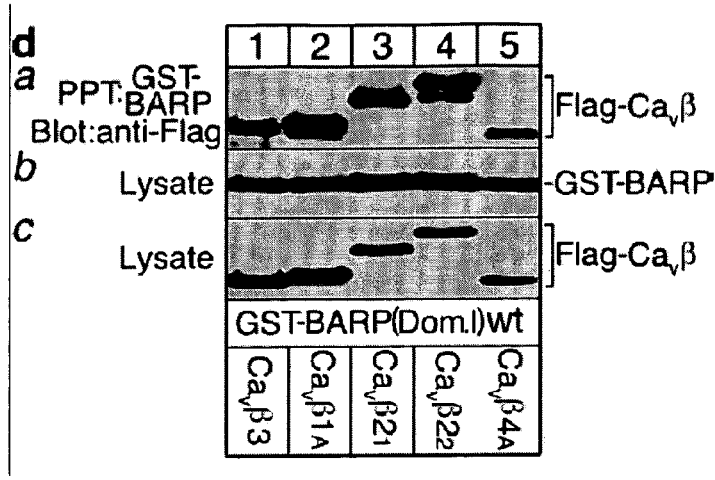

Extensive mutational analysis of BARP by three alanine substitutions using the yeast two-hybrid and computer modelling revealed a first β-subunit interacting domain (Dom. I). surprisingly, the α-helix of this domain shares strong structural similarity with the $\alpha_1$-subunit AID domain, which supports the β-subunit interaction (FIG. 2C(a)). To examine that domain I is indeed a AID-like region, we first mutated the known amino acids in the β-subunit hydrophobic groove responsible for AID interaction, and tested these mutants for association with either AID or BARP domain I by co-precipitation studies. In comparison with the AID domain that only required M196 as a crucial interacting site, almost all amino acid substitutions in the hydrophobic groove of β-subunits interfered with BARP domain I interaction (FIG. 2Cb). We further confirmed this result by substituting amino acids in the AID domain, known to affect β-subunit association and by introducing analogue mutations in BARP domain I (FIG. 2Cc). Isolated BARP domain was also able to associate with all known) β-subunit isoforms (FIG. 2Cd).

Modeling, molecular dynamics and energy refinement was performed with the SYBYL 7.2 SOFTWARE™ (TRIPO INC.™). The β-subunit crystal structure (1VYT) was used as a template to dock the BARP domain I. This domain was modelled as an alpha helix in a reverse orientation. W427 residue of BARP was first positioned similarly to W440 residue of AID and then a molecular dynamics simulation (1000 fs with 1 fs steps at 300K) between residues of β-subunits and domain I within 6 Å performed. Ultimately, energy minimization by the Powel method was applied to obtain the lowest energy conformation.

Figure 2D:
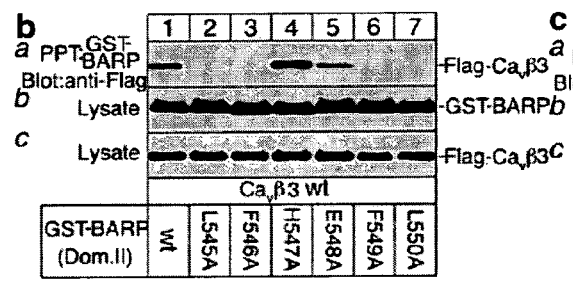
Figure 2D:
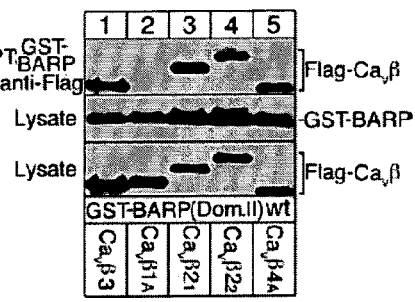
Figure 2D:
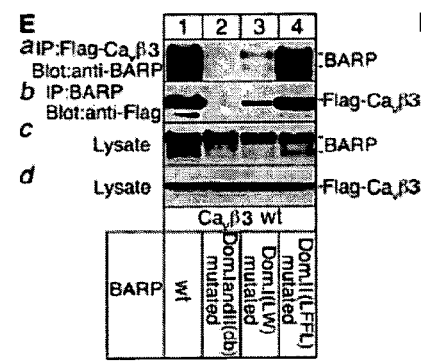
Figure 2D:
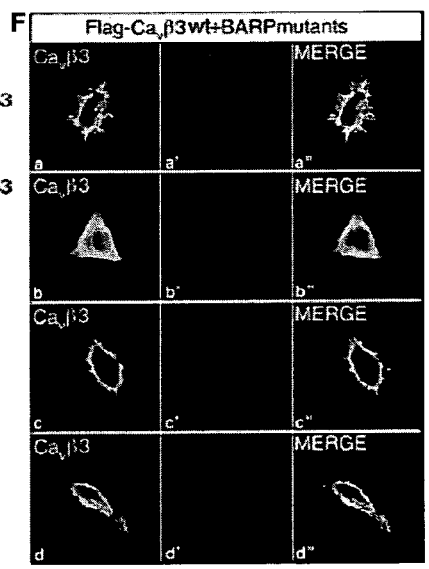

Next, we determined if additional binding sites in BARP are present for β-subunit association. With the use of truncated form of the protein, in which the domain I was abolished, and co-precipitation experiments, we identified a second domain (Dom. II) downstream to the first one (FIG. 2Da). Amino acids substitutions in this domain revealed that hydrophobic residues (leucine and phenylalanine) were critical for efficient binding to β-subunits (FIG. 2Db). Interestingly, the isolated domain II interacted with $\beta_2$, $\beta_3$ and $\beta_4$, but not with $\beta_1$ isoforms (FIG. 2Dc).

Cell Culture and DNA Transfection

To further confirm that both domains associate to the β-subunit in the context of full-length BARP, domain I and II were mutated to abolish their respective interaction. Co-immunoprecipitation and immunostaining studies of overexpressed wild type and mutated full length BARP with β-subunits in PC12 and COS-1 cells (see Supplementary Information 2c) indicated that abolition of both domains prevent BARP) β-subunit association. Reduction of the binding to β-subunits was more pronounced after elimination of Domain I (FIG. 2E). However, the presence of one intact domain in BARP was sufficient to bind and relocated the β-subunit to the plasma membrane, indicating that both domains act independently (FIGS. 2E and F). β-subunit isoforms specific association between full-length BARP and the domain II was also confirmed. Altogether, these results demonstrate that BARP binds specifically β-subunits with two independent interacting domains, an AID-like domain I and a domain II.

COS1, PC12 and TsA201 were grown and transiently transfected with wild type or mutants cDNAs as described. Hippocampus primary cells were purchased from Cambrex and cultured according to the manufacture instructions.

The presence of an AID-like domain in BARP suggests that protein may compete for the α/β subunits interaction. To examine this assumption, $\alpha_1$-subunits ($Ca_v$ 1.2) were co-expressed in COS-1 cells together with wild type or mutated BARP in the presence of N-Flag $Ca_v\beta_3$-subunits and subjected to co-immunoprecipitation studies. The presence of wild type BARP, but not that of the mutant, in which domain I or domain I and II were mutated, prevented α/β subunits association (FIG. 3A, lane 1). If wild type BARP was expressed, immunoprecipitated protein complexes from either $\alpha_1$-subunits (panel c) or $Ca_v\beta$-subunits (panel a) contained BARP but not the other $Ca^{2+}$ channel subunit. When domain II was eliminated, BARP competed partially the association between $Ca_v\beta$-subunits and $\alpha_1$-subunits (lane 4, panel a and c), indicating that domain I of BARP require domain II for its full competitive effect. Importantly, when the single domain I was abolished in BARP, a protein complex including BARP, $\alpha_1$ and $Ca_v\beta$-subunits was revealed (panel d and f). In this triple complexes, only the low molecular weight of the BARP doublet was detected (panel b, lane 3), indicating that BARP posttranslation modifications prevents domain II to associate with $\alpha_1/Ca_v\beta$ complexes. As a control, an $\alpha_1$-subunit mutant that is unable to bind $Ca_v\beta$-subunits did not interact with BARP or β-subunits (lanes 5-8). Similar results were found after co-expressing other $Ca_v\beta$-isoforms with BARP and the $\alpha_1$-subunits ($Ca_v$ 1.2) or after co-expression with other $\alpha_1$-subunit subtypes ($Ca_v$ 2.1 and $Ca_v$ 2.2).

Preparation of cell homogenates lysed into a buffer containing (50 mM Tris-HCl (pH 7.5), 100 mM NaCl, 1 mM MgCl2, 0.5% Triton) supplemented with proteases inhibitors, co-immunoprecipitation and Western blot analysis using the generated antibodies together with monoclonal anti-FLAG (M2; SIGMA™), rabbit anti-GST (SANTA CRUZ BIO-TECHNOLOGY™), rabbit Cav1.2 (CHEMICON INTERNATIONAL™), Cav2.1 (ALOMONE LABS™), Cav2.2 (CALBIOCHEM™), Cavβ3 (ALOMONE LABS™) antibodies were carried out essentially as described in. Brain, skeletal muscle and heart lysates were purchased from ZYAGEN LABORATORIES™. In vitro synthesized BARP was produced by using the TNT quick coupled transcription/translation systems (PROMEGA™). For the dissociation experiments, an AID peptide (AKARGDFQKL-REKQQLEEDLKGALDAATQAED) and a BARP domain I peptide (SYRDLWSLRASLELHAATASD) were synthesized (MIMOTOPES™). Briefly, lysate-containing β3-subunits was pulled down by a GST-AID (amino acid 422-458) fusion protein. After extensive wash to remove unassociated β3-subunits, increasing concentration of peptide (30, 60, 300, 600 nM) were added. After an incubation of four hours, 10% of the supernatant containing the dissociated β3-subunit were loaded on SDS-PAGE and subjected to Western blot analysis. In the absence of competitive peptides, the GST-AID/β3-subunits complex was stable during the four hours incubation.

VDCC BARP Effects on Calcium Channel Activity

The physiological relevance of the interaction between BARP and β-subunits was confirmed by co-immunoprecipitating endogenous BARP and $Ca_v\beta_3$-subunits from brain and PC12 cells (FIG. 3B). Interestingly, overexpressed BARP wild type in PC12 cells was associated with more endogenous $Ca_v\beta_3$-subunit, suggesting that a part of the pool of this subunit is free of BARP in this cell type (lanes 2 and 3). Next, we examined if endogenous BARP is associated preferentially with a specific channel subtypes via $Ca_v\beta$-subunits. Although a weak signal was revealed as expected for the detection of an endogenous triple protein complex, BARP was associated predominantly with the $Ca_v$ 1.2 in PC12 cells and $Ca_v$ 2.1 in brain, consistent with the known role in $Ca^{2+}$-dependent exocytosis. Note that domain I of BARP competed for the $Ca_v1,2$-/$Ca_v\beta3$-subunits association and elimination of this domain allowed BARP to interact with the $Ca_v1,2$/$Ca_v\beta3$-subunits complexes through its domain II.

To examine the functional role of BARP in voltage-gated calcium channels, we co-expressed $\beta_3$-subunits with $\alpha_1$-subunit subtypes Cav 1.2 in the presence of wild type or mutated BARP in TsA201 cells (FIGS. 4A and B). The co-expression of $\alpha_1$-subunit subtype Cav 1.2 with $\beta_3$-subunits elicited $Ca^{2+}$ channel currents. In contrast, no $Ca^{2+}$ channel currents were recorded from cells co-expressing the $Ca^{2+}$ channel subunits and BARP wild type. Mutant BARP defective in the β-interacting domain I and II did not significantly reduce channel activity, confirming the specificity of BARP effect. The single abolition of domain II retained the BARP-induced $Ca^{2+}$ channel down regulation, while the elimination of domain I allowed a recovery of partial $Ca^{2+}$ channel activity. Thus, both β-interacting domains of BARP interfere with the channel activity with a more predominant effect for domain I.

Recordings using the whole-cell patch clamp method were made in TsA201 and PC12 cells as previously described. In TsA201 studies, a new vector derived from the pCMS-EGFP (CLONTECH™) was generated. This vector allowed the concomitant expression of α and β-subunits of Ca2+ channels together with the mCherry fluorescent protein (gift from Soon T. W.). The wild type or mutated BARP cDNAs were introduced into the pCMS-EGFP (CLONTECH™). Cells expressing the enhanced green fluorescent protein (EGFP) and the mCherry protein were selected for measurements. The currents (Iba) were normalized by dividing by the membrane capacitance for each cell. The holding potential was −60 mV and the test pulses of 400 ms.

To verify that BARP had an inhibitory effect on either the presence of other β isoforms or distinct high-voltage-activated (HVA) $Ca^{2+}$ channel, similar recordings were performed. BARP was co-expressed with either β-subunits ($\beta_{1A}$, $\beta_{2I}$ or $\beta_{4B}$) and Cav 1.2 or $\beta_3$-subunits and $\alpha_1$-subunit subtypes ($Ca_v$ 2.1 or $Ca_v$ 2.2) (FIG. 2B). As described previously, depending on β-isoforms and channel subtypes co-expressed, the current amplitude and biophysical properties of the channel varied, confirming β-subunits are the main modulator for $Ca^{2+}$ channel properties. In all cases, co-expression of BARP wild type with $Ca^{2+}$ channel subunits, but not the mutant defective in both β-interacting domains, abolished $Ca^{2+}$ currents. This indicated that BARP inhibits VGCC channels irrespective of their channel subunits composition. Note that $Ca_v\beta$-subunits, but not BARP expression was required for cell surface expression of the $Ca^{2+}$ channels (panel c and d).

Figure 4C:
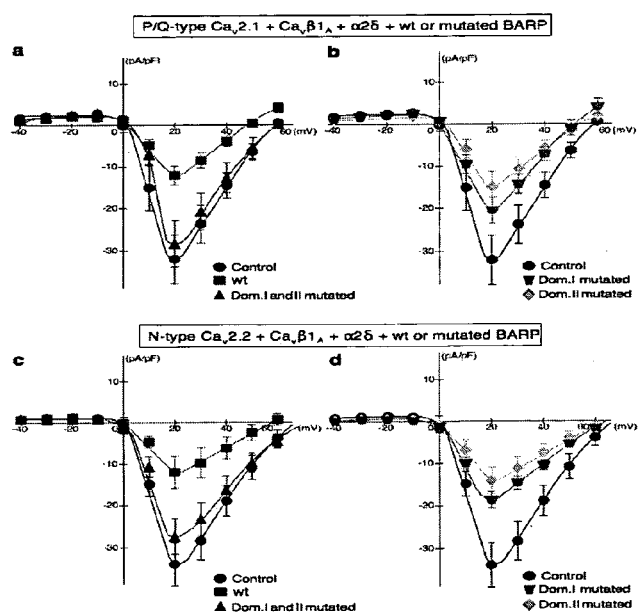

The β-subunits of $Ca^{2+}$ channels have been implicated in the trafficking of $\alpha_1$-subunit to the plasma membrane by increasing the current channel density. To investigate if a reduction of the number of $Ca^{2+}$ channels at the plasma membrane accounts for the BARP-induced abolition of $Ca^{2+}$ current, we monitored in transfected TsA201 by confocal microscopy the cell surface expression of an epitope-tagged $Ca_v$ 1.2, in which the HA-tag was inserted into an external loop (FIG. 4C). In contrast to the expression of $Ca_v$ 1.2 alone, co-expression of $Ca_v$ 1.2 and $\beta_3$-subunits resulted in $\alpha_1$-subunits expression at the plasma membrane (panel a and b). The $Ca^{2+}$ channel cell surface expression was abolished by mutating the β-subunit interacting domain (AID) in $\alpha_1$-subunits (panel c), confirming the role of β-subunits in the cell surface expression of $Ca^{2+}$ channels. Co-expression of wild type or mutated N-myc BARP with $Ca_v$ 1.2 alone (panel d) or together with β-isoforms did not affect $Ca^{2+}$ channel cell surface expression (panels e-l).

These results indicate that BARP, interacting with the β-subunits, does not interfere with the $Ca^{2+}$ channels trafficking but is likely involved in a membrane-delimitated inhibition of the $Ca^{2+}$ channels. In that case, BARP and its AID-like domain may able to dissociate the β-subunit from the $\alpha_1$-subunit at the plasma membrane to produce a reduction of channel activity as it was suggested for the heterotrimeric G-proteins (ref). To verify if the AID-like domain of BARP dissociates β-subunits from the AID of $\alpha_1$-subunits, COS-1 cells lysate expressing $\beta_3$ subunits was incubated with GST-AID fusion protein to form a $\beta_3$/AID complex and subsequently, the dissociation of $\beta_3$ subunits was monitored after addition of an increasing amount of competitive AID or AID-like BARP peptide (FIG. 4D).

VDCC BARP Effects on Hormone Secretion

To elucidate the physiological role of BARP, we examined the functional effects of BARP in PC12 and MIN6 cells in which VGCC triggers $Ca^{2+}$-dependent hormone secretion. In these cells, endogenous BARP is expressed but likely only a fraction of β-subunits are associated (see above). Overexpression of wild type BARP in PC12 cells resulted in a complete inhibition of the endogenous $Ca^{2+}$ channel currents whereas the overexpression of the mutant BARP defective in both β-interacting domains did not significantly reduce channel activity. Overexpression of BARP mutants with the single elimination of domain I and II abolished and partially retained $Ca^{2+}$ channel activity, respectively, confirming the results obtained in the heterologue TsA201 cells system (FIG. 5A).

Human growth hormone secretion in PC12 cells and $[Ca^{2+}]_i$ measurements in MIN6 cells were assayed as described.

To investigate the effect of BARP in $Ca^{2+}$-triggered exocytosis, we overexpressed in PC12 cells BARP and human growth hormone (GH), a marker of $Ca^{+2}$-dependent secretion and monitored the release of GH from the cells after high potassium induced membrane depolarization. Consistent with the $Ca^{2+}$ channel recordings, overexpressed BARP wild type strongly reduced $Ca^{2+}$-dependent secretion, whereas the BARP mutant lacking both β-interacting sites produced only a minor decrease of GH secretion. The single elimination of domain I or II of BARP revealed an intermediate effect on $Ca^{2+}$-triggers secretion, which was less pronounced after abolishing only the domain I.

To verify the implication of BARP in $Ca^{2+}$-dependent exocytosis, we investigated the effects of BARP on electrical activity and internal calcium concentration ($[Ca^{2+}]_i$) in MIN6 cells (FIGS. 5C and D). In control cells, high glucose (25 mM) stimulation progressively depolarized the plasma membrane with a concomitant increase in ($[Ca^{2+}]_i$), typical of glucose induced VGCC channel activity. Both effects were abolished after overexpression of BARP wild type, but not after the overexpression of BARP mutant defective in both β binding sites. These results indicate that BARP may have a physiological role in $Ca^{2+}$-dependent exocytosis by modulating the VGCC activity.

Overexpression of BARP down regulates VGCC activity and $Ca^{2+}$-dependent hormone-secretion, but does not affect cell surface expression of $Ca^{2+}$ channels.

On the basis of these results, we propose that BARP localizes the β-subunit in the active zone for fast synaptic neurotransmitters or hormones release, and modulates its function. The specific subcellular localization of BARP and the detection of α-, β-subunits and BARP as a protein complex indicates that β-subunits is anchored with the domain II of BARP and consequently to the secretory vesicles.

It is thought that syntaxin1 may play a negative feedback loop on $α_1$-subunit to inactivate the $Ca^{2+}$ channel after neurotransmitters release. By analogy, BARP may play a similar role for β-subunits. In that case, the feedback inactivation may be produced by the α-/β-subunits dissociation. Indeed, this inhibitory mechanism was found for the modulation of the $Ca_v2$ by the G protein-coupled receptor. Though, Gβγ directly associates with the $α_1$-subunits and dissociates β-subunits from the $Ca^{2+}$ channel.

In this case, overexpression of BARP that favours channels inactivation may be used as a genetic calcium channel blocker. In lethargic mouse model in which $β_4$-subunits are suppressed, a compensatory effect on $Ca^{2+}$ channel activities by other β-isoforms was found in Purkinje neurons. BARP that is highly expressed in these neurons may have recruited other β-isoforms to prevent complete seizure of the $Ca^{2+}$ channel function. By all means, the specific localization and role of BARP in $Ca^{2+}$-dependent secretion makes this protein a good candidate for drug design.

While the invention has been described with reference to specific methods and embodiments, it will be appreciated that various modifications and changes may be made without departing from the invention.

The invention claimed is:

1. A kit for identifying a VDCC BARP comprising at least a detectably labeled polynucleotide that is covalently attached to a solid substrate and is complementary to a portion of the voltage-dependent calcium channel (VDCC) β subunit anchoring regulator protein (BARP) gene comprising the sequence set out in SEQ ID NO: 5.

2. The kit of claim 1, wherein the kit further comprises a sequence listing of a complete or a substantially complete VDCC BARP gene sequence encoding a functional VDCC BARP polypeptide sequence that comprises the sequence set out in SEQ ID NO: 6 in a patient that is not suffering from a disorder selected from the group consisting of (i) a condition characterised by calcium imbalance; (ii) a condition linked to voltage gated calcium channel (VGCC) function or activity; (iii) ataxia; (iv) migraine; (v) epilepsy; (vi) neurodegeneration; (vii) hypertension; (viii) a cardiac disorder; and (ix) diabetes.

3. The kit of claim 1, wherein the polynucleotide is biotinylated.

4. The kit of claim 1, wherein the polynucleotide is a recombinant polynucleotide.

5. The kit of claim 1, wherein the polynucleotide is a synthetic polynucleotide.

6. A recombinant expression vector, comprising a polynucleotide selected from:
   (a) a polynucleotide comprising the nucleotide sequence set out in SEQ ID NO: 5 linked to a nucleotide sequence encoding a localization signal; and
   (b) a polynucleotide encoding a voltage-dependent calcium channel (VDCC) β subunit anchoring regulator protein (BARP) polypeptide that comprises the sequence set out in SEQ ID NO: 6 linked to a localization signal,
   wherein the polynucleotide is operably linked to a regulatory sequence capable of directing expression of said polynucleotide in a host cell, wherein the recombinant expression vector expresses a modulator of voltage gated calcium channel activity, and wherein the localization signal is from a non-native VDCC BARP protein receptor that allows the VDCC BARP protein to cross and/or lodge in cell membranes.

7. A recombinant expression vector, comprising a polynucleotide selected from:
   (a) a polynucleotide comprising the nucleotide sequence set out in SEQ ID NO: 5 linked to a nucleotide sequence encoding a localization signal; and
   (b) a polynucleotide encoding a voltage-dependent calcium channel (VDCC) β subunit anchoring regulator protein (BARP) polypeptide that comprises the sequence set out in SEQ ID NO: 6 linked to a localization signal, wherein the polynucleotide is operably linked to a regulatory sequence capable of directing expression of said polynucleotide in a host cell, wherein the recombinant expression vector expresses a modulator of voltage gated calcium channel activity, and wherein the localization signal is a myristoylation signal.

* * * * *

SEQUENCE LISTING

```
<160> NUMBER OF SEQ ID NOS: 11

<210> SEQ ID NO 1
<211> LENGTH: 3982
<212> TYPE: DNA
<213> ORGANISM: Rattus rattus

<400> SEQUENCE: 1
agacgcggcg gcgagagcgg cggggcggt caggctgcgg gaccgggcgg ttaccgggta      60
cacagagcca ggggccggag cgggcgcatc gccaacgcga tcacgtgcgc agccccacct    120
ctcctgcgtg cctcctccgc gcgctgctct ccccattcat aaattctccg tcggctccgc    180
ggccaccgag ctccagagcc aaccgggaga gccgtgttat ctgccgcccg ccctcccgcc    240
gcccatgggc cgcacgcccc ggcgctgagc ctcaaaatgc agcccacggc caccatggcc    300
acagcggccg ccactactgc cacggttgcc ctgacgactt cgtgggacaa tgccaccaac    360
cgccccacgg cggagcctga ccccatcttg gacaactatg tgctgctggt ggtggtgatg    420
tcgctgttcg ttggaggcac gctggtggtg ctgtctggcg ttcttctgct ctgcaaacgc    480
tgctgggagg tgcaccagcg cttcaacagg gccatggaag aaacagaaaa gaccaccact    540
acctacctgg acaacggcac ccaccccata caagacccg actgcagggg ggaagacccc    600
gagggccagg acaccgaaac agagcgcttc ctagccacca cctccaccgg tcgccgcgtg    660
tccttcaacg aggctgccct gtttgaacag agccgcaagg ctcaggacaa gggccgccgg    720
tacaccctga cagaagggga tttccatcac ctcaagaatg cccgcctcac ccacctccac    780
ctaccgcctc tcaaaatcgc taccatccat gagtgtgact cgggtgaggc cagtgctgcg    840
gccacgcccc accccaccc ggcttccacc cccaaggaca gcttggctat attccagccc    900
cctgggaagt ccctcactgg ccactcggtg ggccccagct ctgccctccc aggtgatccc    960
```

```
tacagctccg tggacttctc ggagatcagc ccctcggcct ccagtgactc tggggagggc     1020
acctcgttag atgcgggtac ccggggtacc aaggctgctg ggcccgagac agcacctggg     1080
gagatgggca caggctcctc cggggctggc actgttttgc aattcttcac tcggctacgc     1140
cgccatgcca gcctggatgg agccagcccc tacttcaagg tcaagaaatg aagttggag      1200 tccagccaga gagcgtccag tctggacacg agaggttccc cgaagcggca ccactttcag     1260
cgacagcggg cagccagcga gagcatggag caggaggggg atatccccca tgctgacttc     1320
attcaataca ttgccagcgc aggcgactcg gtggccttcc caccccccg  cccctttctg     1380 gccagcccca ccagcccgcc ccccactctc ggcaggtatt tttcagtaga tagaggtgct     1440
aagggtgggc ctgtgggccc ctgccctgcc ccgtccccca taggtggccc ggggactgcc     1500
cttctggccc tgtggacacg aactcgagtc accctggcca cttcatgggg gccacctctc     1560
cagcgcagac cggaggagga ggagggaagc agggagagac tgggtaaggg taggtgggca     1620
gttgatggtc ccagggtctc caagatgaga cacccaccag agcagggcag tgggctgggg     1680
cctaccatgg ccctgccgat ttgtagcagg ctccgaggcc tgaagggctc ctcagtggtc     1740
ccagcgtccc ttctgcctgc ctgcactcct gatgtatgcc tgaccccaat cagggagcgt     1800
ccttggtaac ggctgctatc agaagtaacc tcccacccca agccaaaagc aaaactccca     1860
aatgctaaaa acactgggaa acgggctgag gccttgccaa cttggggtg  accttgagc     1920 ttcattgatt cacacccagc ttgtactagg tccagtgggt gaagtaacca cctagtacaa     1980
gggcctgatg atttggtgtc tagttcagat ccattctctt ggagtcccct tgcacatcaa     2040
gagaattact tgagtggccc agattcgatg agtgtccctc catgtccata gtccctaaag     2100
cacaaacacg tggccggcag ggcagggcaa tgcctgcagg ctctgaccac atgggcctgg     2160
ccttgcaggc tagaggcagc tgaggcggcg ggaggaggaa gccccgagac tcctccggag     2220
catggcatca gtttgggggcc cgagcatgcg cagcagcagg accgcagca  agagcaggac     2280 gccgagcatg cacagtgcag ctaccgtgat ctgtggagcc ttcgtgcttc gctcgagctc     2340
cacgcagcca ctgcatcaga ccacagcagt agcggcaatg accgtgactc agtgcgcagc     2400
ggcgatagct cgggctccgg ttccgggggt ggaggcgcag cacccgcctt ccgcccccct     2460
cctgagtctc cgcctgcctt gcggcctaag gacggcgaag cccgacgcct gttacagatg     2520
gacagtggct acgcgagcat cgaggacgt  ggagctggcg atgaagtttc tgaacttcct     2580
gctccagctc ggagccctcc ccgcagcccg cgagcctggc cacgcaggcc gcgccgcgat     2640
tatagcatcg atgagaagac ggacgctctt ttccatgaat tcctgcgcca cgatcctcat     2700
tttgatgatg ctccaagaca ccgcgcacgt gcgcatcctc acactcatgc gcggaagcaa     2760 tgcaacagA  gaggccggca gcacagcgac cccgaggtg  cacgcgtggc cacgccccct     2820
ggggctaccc gccccacacg tgccccctta cgccgtgggg atagtgttga ttgtcctcct     2880
gaaggccgtg cgccgcccat caccggtgat gacccatcca ttcccgtcat tgaggaggag     2940
cctggtggtg gaggcagtgg ttgcccaggc tctgggttat gtgttgagcc cgccggggca     3000
ctgctggaca aactagcagc tagcctcgac gagagactct tctctccccg tcttgctgag     3060
ccagttgcct catccccggt gctgattgtc gctgctgccg ccctacatc  ccctgaccac     3120 agcccagcct aagctctgtg tactggacct gcctctcggc tgctttgccg gcggcacgtg     3180
gggccgctgt gggaatggtg gcgacagcgg gagcaacctg aggttgctgt gcatgggtac     3240
gcggcccaaa tcccaagtgt gtacaaggag tgtcccctcg ggcacttagc agggtgcagt     3300
```

-continued

```
gggcctccgg atgcacaagg cctccggacc caggctcagc tgcagggagg atgaagatct   3360
tggattctca agtccatata cggttgaccc ccggcaccca gcctctggcc acagatgcgg   3420
gtggagcagg ttctgaggtg cgcgtgcagc ctccctccag gatcagccga acctccacac   3480
tcgtgagcac gtgctggcag tgccactgca tgcgtgaacc tactggaggg gaagtgactg   3540
cggggcactg aggatcagag aggaacacgc gccccagatc cttaatcctt tccctgtcc    3600 atggtatgca ctttgtagca actgtacctt tcctctctga gcaataaccg actgcgcctg   3660
ctcgctctct gcatgtgcac aggctccagc ctgtcccatc cctccccacg agctttgggc   3720
tttaaacaca gagacagaac agcccggtgg cagcttcaag tttcccaagc tttatttatt   3780
gccaaaagat tgggcagcct cgccatgagt gcctgcccac tccctgccct gcgccctgtg   3840
gttggtcgtg ttgtctggtt gatcataaat gtctctgcat atttgttcgc tctgggtttt   3900
ctctgcaggc caccctgtgc cccgcctgct ccctatttcc aaacatcctc atagccacag   3960
ctcaaatcct cctgttttat tt                                            3982
```

<210> SEQ ID NO 2
<211> LENGTH: 700
<212> TYPE: PRT
<213> ORGANISM: Rattus rattus

<400> SEQUENCE: 2

| | | | | | | | | | | | | | | | |
|---|---|---|---|---|---|---|---|---|---|---|---|---|---|---|---|
| Met | Gln | Pro | Thr | Ala | Thr | Met | Ala | Thr | Ala | Ala | Thr | Thr | Ala | Thr | |
| 1 | | | | 5 | | | | | 10 | | | | | 15 | |

| Val | Ala | Leu | Thr | Thr | Ser | Trp | Asp | Asn | Ala | Thr | Asn | Arg | Pro | Thr | Ala |
| | | | 20 | | | | | 25 | | | | | 30 | | |

| Glu | Pro | Asp | Pro | Ile | Leu | Asp | Asn | Tyr | Val | Leu | Leu | Val | Val | Met |
| | | | 35 | | | | | 40 | | | | | 45 | | |

| Ser | Leu | Phe | Val | Gly | Gly | Thr | Leu | Val | Val | Leu | Ser | Gly | Val | Leu | Leu |
| | | 50 | | | | | 55 | | | | | 60 | | | |

| Leu | Cys | Lys | Arg | Cys | Trp | Glu | Val | His | Gln | Arg | Phe | Asn | Arg | Ala | Met |
| 65 | | | | 70 | | | | | 75 | | | | | 80 | |

| Glu | Glu | Thr | Glu | Lys | Thr | Thr | Thr | Tyr | Leu | Asp | Asn | Gly | Thr | His |
| | | | | 85 | | | | | 90 | | | | | 95 | |

| Pro | Ile | Gln | Asp | Pro | Asp | Cys | Arg | Gly | Glu | Asp | Pro | Glu | Gly | Gln | Asp |
| | | | 100 | | | | | 105 | | | | | 110 | | |

| Thr | Glu | Thr | Glu | Arg | Phe | Leu | Ala | Thr | Thr | Ser | Thr | Gly | Arg | Arg | Val |
| | | | 115 | | | | | 120 | | | | | 125 | | |

| Ser | Phe | Asn | Glu | Ala | Ala | Leu | Phe | Glu | Gln | Ser | Arg | Lys | Ala | Gln | Asp |
| | | 130 | | | | | 135 | | | | | 140 | | | |

| Lys | Gly | Arg | Arg | Tyr | Thr | Leu | Thr | Glu | Gly | Asp | Phe | His | His | Leu | Lys |
| 145 | | | | 150 | | | | | 155 | | | | | 160 | |

| Asn | Ala | Arg | Leu | Thr | His | Leu | His | Leu | Pro | Pro | Leu | Lys | Ile | Ala | Thr |
| | | | | 165 | | | | | 170 | | | | | 175 | |

| Ile | His | Glu | Cys | Asp | Ser | Gly | Glu | Ala | Ser | Ala | Ala | Thr | Pro | His |
| | | | 180 | | | | | 185 | | | | | 190 | | |

| Pro | His | Pro | Ala | Ser | Thr | Pro | Lys | Asp | Ser | Leu | Ala | Ile | Phe | Gln | Pro |
| | | 195 | | | | | 200 | | | | | 205 | | | |

| Pro | Gly | Lys | Ser | Leu | Thr | Gly | His | Ser | Val | Pro | Ser | Ser | Ala | Leu |
| | | 210 | | | | | 215 | | | | | 220 | | | |

| Pro | Gly | Asp | Pro | Tyr | Ser | Ser | Val | Asp | Phe | Ser | Glu | Ile | Ser | Pro | Ser |
| 225 | | | | 230 | | | | | 235 | | | | | 240 | |

| Ala | Ser | Ser | Asp | Ser | Gly | Glu | Gly | Thr | Ser | Leu | Asp | Ala | Gly | Thr | Arg |
| | | | | 245 | | | | | 250 | | | | | 255 | |

-continued

```
Gly Thr Lys Ala Ala Gly Pro Glu Thr Ala Pro Gly Glu Met Gly Thr
            260                 265                 270

Gly Ser Ser Gly Ala Gly Thr Val Leu Gln Phe Phe Thr Arg Leu Arg
        275                 280                 285

Arg His Ala Ser Leu Asp Gly Ala Ser Pro Tyr Phe Lys Val Lys Lys
    290                 295                 300

Trp Lys Leu Glu Ser Ser Gln Arg Ala Ser Ser Leu Asp Thr Arg Gly
305                 310                 315                 320

Ser Pro Lys Arg His His Phe Gln Arg Gln Arg Ala Ala Ser Glu Ser
                325                 330                 335

Met Glu Gln Glu Gly Asp Ile Pro His Ala Asp Phe Ile Gln Tyr Ile
            340                 345                 350

Ala Ser Ala Gly Asp Ser Val Ala Phe Pro Pro Arg Pro Phe Leu
        355                 360                 365

Ala Ser Pro Thr Ser Pro Pro Thr Leu Gly Arg Leu Glu Ala Ala
    370                 375                 380

Glu Ala Ala Gly Gly Gly Ser Pro Glu Thr Pro Glu His Gly Ile
385                 390                 395                 400

Ser Leu Gly Pro Glu His Ala Gln Gln Gln Asp Pro Gln Glu Gln
                405                 410                 415

Asp Ala Glu His Ala Gln Cys Ser Tyr Arg Asp Leu Trp Ser Leu Arg
            420                 425                 430

Ala Ser Leu Glu Leu His Ala Ala Thr Ala Ser Asp His Ser Ser Ser
        435                 440                 445

Gly Asn Asp Arg Asp Ser Val Arg Ser Gly Asp Ser Ser Gly Ser Gly
    450                 455                 460

Ser Gly Gly Gly Ala Ala Pro Ala Phe Pro Pro Pro Glu Ser
465                 470                 475                 480

Pro Pro Ala Leu Arg Pro Lys Asp Gly Glu Ala Arg Arg Leu Leu Gln
                485                 490                 495

Met Asp Ser Gly Tyr Ala Ser Ile Glu Gly Arg Gly Ala Gly Asp Glu
            500                 505                 510

Val Ser Glu Leu Pro Ala Pro Ala Arg Ser Pro Arg Ser Pro Arg
        515                 520                 525

Ala Trp Pro Arg Arg Pro Arg Arg Asp Tyr Ser Ile Asp Glu Lys Thr
    530                 535                 540

Asp Ala Leu Phe His Glu Phe Leu Arg His Asp Pro His Phe Asp Asp
545                 550                 555                 560

Ala Pro Arg His Arg Ala Arg Ala His Pro His Thr His Ala Arg Lys
                565                 570                 575

Gln Trp Gln Gln Arg Gly Arg Gln His Ser Asp Pro Gly Gly Ala Arg
            580                 585                 590

Val Ala Thr Pro Pro Gly Ala Thr Arg Pro Thr Arg Ala Pro Leu Arg
        595                 600                 605

Arg Gly Asp Ser Val Asp Cys Pro Pro Glu Gly Arg Ala Pro Pro Ile
    610                 615                 620

Thr Gly Asp Asp Pro Ser Ile Pro Val Ile Glu Glu Pro Gly Gly
625                 630                 635                 640

Gly Gly Ser Gly Cys Pro Gly Ser Gly Leu Cys Val Glu Pro Ala Gly
                645                 650                 655

Ala Leu Leu Asp Lys Leu Ala Ala Ser Leu Asp Glu Arg Leu Phe Ser
            660                 665                 670
```

Pro Arg Leu Ala Glu Pro Val Ala Ser Ser Pro Val Leu Ile Val Ala
        675                 680                 685

Ala Ala Ala Pro Thr Ser Pro Asp His Ser Pro Ala
    690                 695                 700

<210> SEQ ID NO 3
<211> LENGTH: 2361
<212> TYPE: DNA
<213> ORGANISM: Mus musculus

<400> SEQUENCE: 3

| | | | | | |
|---|---|---|---|---|---|
| attttccagc | cccctgggaa | aaccctcacc | ggccactcag | tcggcccag | ctccgcctg | 60 |
| ccaggaggtc | cctacaactc | cgtggacttc | tcagagatca | gcccctcaac | ctccagtgac | 120 |
| tctggggagg | gcatttcgat | gcaggtaccc | ggggtgccaa | ggctgctggg | cctgaaacag | 180 |
| tgcctgggga | gatgggcaca | ggctcctccg | ggtcgggcac | tgttttgcaa | ttcttcactc | 240 |
| ggctacgccg | acatgccagc | ctggatggag | ccagcccta | cttcaaggtc | aagaaatgga | 300 |
| agctggagcc | cagccagaga | gcgtccagtc | tggacacgag | aggttcccct | aagaggcacc | 360 |
| actttcagcg | gcagcgggca | gccagtgaga | gcatggagca | ggaggggac | gtcccccatg | 420 |
| ccgacttcat | tcagtacatt | gccagcgcag | gcgactcggt | ggccttccca | ccccccgcc | 480 |
| cctttctggc | cagccccacc | agcccgcccc | ccactctcgg | caggctagag | gcagcagagg | 540 |
| cggcgggagg | agcgagccct | gagactcctc | cggagcatgg | catcagtttg | gggcccgagc | 600 |
| atgcgcagca | gcaggacccg | cagcaagagc | aggacgccga | gcatgcacag | tgcagctacc | 660 |
| gtgacctgtg | gagccttcgt | gcttcgctcg | agctccatgc | agccactgca | tcggaccaca | 720 |
| gcagcagcgg | caatgaccgc | gactcagtgc | gcagcggcga | tagctcgggc | tcgggttccg | 780 |
| gaggtggagg | ggcagcaccc | gccttcccac | ccctccgga | gtctccacct | gctttgaggc | 840 |
| ctaaggacgg | cgaagcccgc | cgcctgctac | agatggacag | tggctatgcg | agcatcgagg | 900 |
| ggcgcggagc | aggcgacgaa | gtttcagaac | ttcctgctcc | agcccgcagt | cctccccgca | 960 |
| gcccgcgagc | ctggccacgc | aggccgcgcc | gcgattacag | catcgacgag | aagacggacg | 1020 |
| ctcttttcca | tgagttcctg | cgccatgacc | ctcattttga | cgatgcaccg | cgtcaccgca | 1080 |
| cacgtgcaca | tcctcacact | catgcgcgga | agcaatggca | acagagagga | cggcagcaca | 1140 |
| gcgaccccgg | tggtgcacgt | gcagccacgc | ccctggagt | ggcccgccct | acacgtgcgc | 1200 |
| cattacgccg | tggggacagc | gttgattgtc | ctcctgaagg | ccgtgcgctg | cccatcacgg | 1260 |
| gtgatgaccc | atccattcct | gtcatcgagg | aggagcctgg | cggtggaggc | ggtggttgcc | 1320 |
| caggctctgg | gttgtgcgtt | gagcccgccg | gggccctgct | agacaagcta | gcagccagcc | 1380 |
| tcgacgagag | actcttctct | cccgtcttg | ctgagccagt | tgcctcatcc | caggtgctga | 1440 |
| ttgtcgctgc | tgctgcccct | acatcccctg | accacagccc | ggcctaagct | ctgtactgga | 1500 |
| cctgcctctc | tgctgcttct | ccggcagcac | atggggctgc | tgtgggaatg | gtggcaacag | 1560 |
| cgggagcaac | ctgaggtggc | cgtgcatggg | tacacggccc | ccaaatccca | agtgtgcaca | 1620 |
| tatagtgtcc | cctgggcact | tagcgcagtg | gcctccggaa | gcaagaggct | ccaggaccca | 1680 |
| ggctcaactg | cagggaggat | gacgagactg | gactctccgg | tccatatatg | gttgacccca | 1740 |
| gcacccagcc | tctggccaca | gatgctggtg | gagcaggttc | tgaggtgcat | gtgcagcctc | 1800 |
| cctccaggat | cagctgaccc | tccactcgtg | agcactggca | ggcagtaaca | ctgcctgcca | 1860 |
| ctgtgtgagc | gaacctactg | gaggtgaagt | gactgtgggg | cactgaggat | cagagaggag | 1920 |
| ctcgccgccc | catattctga | gttgatttac | cctgtccatg | gtatgcgctc | tacctttcct | 1980 |

```
ctctgagcaa taaccgaccg cgcctgctct ctgcatgtgc acaggctccc cgtctcattc   2040
ctccccgaga gccttgggct ttggacacaa cggacagaac agcccaggtg gcagcttcaa   2100
gtttcccaag ctttatttat tgccaaaaga tagggcagac tcgctgtgag tgcctgccca   2160
ctccctgccc tgcgccctct gtggttggtc gtgttgtctg gttaatcata aatgtctctg   2220
catatttgtt tgctctgggt tttctctgca ggccaccctg tgccccgcct gctccatatt   2280
tccaaacacc ctcatagcca tagctcaaat ccacctgttt tattaaaaaa aagaaacca   2340 aaaaaaaaaa aaaaaaaaa a                                              2361
```

<210> SEQ ID NO 4
<211> LENGTH: 698
<212> TYPE: PRT
<213> ORGANISM: Mus musculus

<400> SEQUENCE: 4

```
Met Gln Pro Thr Ala Thr Met Ala Thr Ala Ala Thr Thr Ala Thr
 1               5                  10                  15

Val Ala Leu Thr Thr Ser Trp Asp Asn Ala Thr Ser Arg Pro Thr Ala
                20                  25                  30

Glu Pro Asp Pro Ile Leu Asp Asn Tyr Val Leu Leu Val Val Met
                35                  40                  45

Ser Leu Phe Val Gly Gly Thr Leu Val Val Leu Ser Gly Val Leu Leu
 50                  55                  60

Leu Cys Lys Arg Cys Trp Glu Val His Gln Arg Phe Asn Arg Ala Met
65                  70                  75                  80

Glu Glu Ala Glu Lys Thr Thr Thr Tyr Leu Asp Asn Gly Thr His
                85                  90                  95

Pro Ile Gln Asp Pro Asp Cys Arg Gly Glu Asp Pro Glu Gly Gln Asp
                100                 105                 110

Thr Glu Thr Glu Arg Phe Leu Ala Thr Ser Ser Thr Gly Arg Arg Val
                115                 120                 125

Ser Phe Asn Glu Ala Ala Leu Phe Glu Gln Ser Arg Lys Ala Gln Asp
 130                 135                 140

Lys Gly Arg Arg Tyr Thr Leu Thr Glu Gly Asp Phe His His Leu Lys
145                 150                 155                 160

Asn Ala Arg Leu Thr His Leu His Leu Pro Pro Leu Lys Ile Ala Thr
                165                 170                 175

Ile His Glu Cys Asp Ser Gly Glu Ala Ser Ala Ala Thr Pro His
                180                 185                 190

Pro Ala Thr Thr Ser Lys Asp Ser Leu Ala Ile Phe Gln Pro Pro Gly
                195                 200                 205

Lys Thr Leu Thr Gly His Ser Val Gly Pro Ser Ser Ala Leu Pro Gly
 210                 215                 220

Gly Pro Tyr Asn Ser Val Asp Phe Ser Glu Ile Ser Pro Ser Thr Ser
225                 230                 235                 240

Ser Asp Ser Gly Glu Gly Ile Ser Leu Asp Ala Gly Thr Arg Gly Ala
                245                 250                 255

Lys Ala Ala Gly Pro Glu Thr Val Pro Gly Glu Met Gly Thr Gly Ser
                260                 265                 270

Ser Gly Ser Gly Thr Val Leu Gln Phe Phe Thr Arg Leu Arg Arg His
                275                 280                 285

Ala Ser Leu Asp Gly Ala Ser Pro Tyr Phe Lys Val Lys Lys Trp Lys
 290                 295                 300
```

Leu Glu Pro Ser Gln Arg Ala Ser Ser Leu Asp Thr Arg Gly Ser Pro
305                 310                 315                 320

Lys Arg His His Phe Gln Arg Gln Arg Ala Ser Glu Ser Met Glu
            325                 330                 335

Gln Glu Gly Asp Val Pro His Ala Asp Phe Ile Gln Tyr Ile Ala Ser
            340                 345                 350

Ala Gly Asp Ser Val Ala Phe Pro Pro Arg Pro Phe Leu Ala Ser
            355                 360                 365

Pro Thr Ser Pro Pro Thr Leu Gly Arg Leu Glu Ala Ala Glu Ala
370                 375                 380

Ala Gly Gly Ala Ser Glu Thr Pro Glu His Gly Ile Ser Leu
385                 390                 395                 400

Gly Pro Glu His Ala Gln Gln Gln Asp Pro Gln Gln Glu Gln Asp Ala
            405                 410                 415

Glu His Ala Gln Cys Ser Tyr Arg Asp Leu Trp Ser Leu Arg Ala Ser
            420                 425                 430

Leu Glu Leu His Ala Ala Thr Ala Ser Asp His Ser Ser Gly Asn
            435                 440                 445

Asp Arg Asp Ser Val Arg Ser Gly Asp Ser Gly Ser Gly Ser Gly
450                 455                 460

Gly Gly Gly Ala Ala Pro Ala Phe Pro Pro Pro Glu Ser Pro Pro
465                 470                 475                 480

Ala Leu Arg Pro Lys Asp Gly Glu Ala Arg Arg Leu Leu Gln Met Asp
            485                 490                 495

Ser Gly Tyr Ala Ser Ile Glu Gly Arg Gly Ala Gly Asp Glu Val Ser
            500                 505                 510

Glu Leu Pro Ala Pro Ala Arg Ser Pro Pro Arg Ser Pro Arg Ala Trp
            515                 520                 525

Pro Arg Arg Pro Arg Arg Asp Tyr Ser Ile Asp Glu Lys Thr Asp Ala
            530                 535                 540

Leu Phe His Glu Phe Leu Arg His Asp Pro His Phe Asp Asp Ala Pro
545                 550                 555                 560

Arg His Arg Thr Arg Ala His Pro His Thr His Ala Arg Lys Gln Trp
            565                 570                 575

Gln Gln Arg Gly Arg Gln His Ser Asp Pro Gly Gly Ala Arg Ala Ala
            580                 585                 590

Thr Pro Pro Gly Val Ala Arg Pro Thr Arg Ala Pro Leu Arg Arg Gly
            595                 600                 605

Asp Ser Val Asp Cys Pro Pro Glu Gly Arg Ala Leu Pro Ile Thr Gly
            610                 615                 620

Asp Asp Pro Ser Ile Pro Val Ile Glu Glu Pro Gly Gly Gly Gly
625                 630                 635                 640

Gly Gly Cys Pro Gly Ser Gly Leu Cys Val Glu Pro Ala Gly Ala Leu
            645                 650                 655

Leu Asp Lys Leu Ala Ala Ser Leu Asp Glu Arg Leu Phe Ser Pro Arg
            660                 665                 670

Leu Ala Glu Pro Val Ala Ser Ser Gln Val Leu Ile Val Ala Ala Ala
            675                 680                 685

Ala Pro Thr Ser Pro Asp His Ser Pro Ala
            690                 695

<210> SEQ ID NO 5
<211> LENGTH: 2407

<212> TYPE: DNA
<213> ORGANISM: Homo sapiens

<400> SEQUENCE: 5

| | | | | | |
|---|---|---|---|---|---|
| gccaccgggc | gccggagcca | gccgcgagcg | ccacgcagcc | gcccgccgcc | agcccgccgc | 60 |
| ccatgggccg | ctcgtcccgg | cgctgagggc | cctcctcccc | agttcagaat | gcagcccaca | 120 |
| gccaccatgg | ccacagccgc | caccaccacc | accaccacca | ctgccacagt | agccctgacg | 180 |
| acgtcgtggg | acaatgccac | tggacgcccc | acggcagagc | cagaccccat | cctggacaac | 240 |
| tacgtgctgc | tggtggtggt | gatgtcgctg | ttcgtggggg | gcacgctggt | ggtgttgtct | 300 |
| ggcgtcctgc | tcctctgcaa | gcgctgctgg | gacgtccacc | agcgcctcaa | cagggccatg | 360 |
| gaggaagcgg | agaagaccac | caccacctac | ctggacaacg | gcacccaccc | agcccaagac | 420 |
| cccgacttcc | ggggagagga | ccccgagtgc | caggatgcgg | agaccgaacg | cttcctgtcc | 480 |
| accagctcca | cgggccgccg | ggtctccttc | aatgaggcgg | cgctgtttga | gcagagccgc | 540 |
| aagacgcagg | acaagggtcg | ccggtacaca | ctgacggagg | gggacttcca | ccacctgaag | 600 |
| aatgcccggc | tcacgcacct | gcacctgccg | cccctcaaga | ttgtcaccat | ccacgagtgt | 660 |
| gactcaggcg | aggccagctc | agccaccacg | ccccacccgg | ccacctctcc | caaggccact | 720 |
| ctggccatct | tccagccccc | ggggaaggcc | ctcaccggcc | gctctgtggg | ccccagctcc | 780 |
| gccctgccag | gtgaccccta | caactcagcc | gcgggcgcca | ctgacttcgc | agagatcagc | 840 |
| ccctcggcat | ctagcgactc | tggggaaggc | accttgttgg | atgccggtac | caggagcacc | 900 |
| aaggctggag | ggcccgggc | tgcagcaggg | cctggggagg | cgggcccggg | atccggggca | 960 |
| ggtaccgttc | tgcagttcct | cacccgcctg | cgccgccatg | ccagcctgga | tggggccagc | 1020 |
| ccctatttca | aggtcaagaa | gtggaagctg | agcccagcc | agcgggcagc | cagtctggac | 1080 |
| acgagaggtt | ccccaagcg | gcaccacttc | cagcggcagc | gggcagccag | tgagagcacg | 1140 |
| gagcaggagg | aggggatgc | cccccaggag | gacttcatcc | agtacattgc | ccgggcgggc | 1200 |
| gacgccgtgg | ccttcccgcg | ccccgcccc | tttctggcca | gcccgccccc | tgctctcggc | 1260 |
| aggtatttt | cagtagatgg | aggtgctagg | ggtggacctg | tgggcccttg | cccccttcg | 1320 |
| cccccccta | ggcggcccag | ggagcgctct | ccaggccccg | tggacacgcg | ctcgcctgcc | 1380 |
| tccagcggca | aggcccctcc | cagaggcgga | ctcactgggg | ccacctctcc | agcatggacc | 1440 |
| agaggaggga | agcagggaga | gactgggtaa | gggtagggcg | gtgggtgggg | aggaggggcc | 1500 |
| ccccgaggat | ggcgctggta | ctgctgcttg | ctggtggagt | ccgaggcctg | aagggttctg | 1560 |
| ctgtggtccc | aggccctctc | ccaccccgc | cccgcccatg | ctcccaaggc | tgggcagact | 1620 |
| cctctcagaa | gctgctgtga | ccactccggc | cagcagcacc | cctcccccaa | cccaagggca | 1680 |
| actttcctga | agcccagggc | ccacgtcggt | gggatgggaa | tggggcgtgg | ggctggggca | 1740 |
| gagcagggtt | cctggggcag | ccctggtatg | gcggtgacc | ctcacgtctg | tgcactgtcc | 1800 |
| tcctgctggt | tatccagcat | gggtgggcag | agagccctag | cctggagcag | gggctgagct | 1860 |
| ggactcaacc | gcgtccagtc | catcccctgc | ggctcccacg | tccactggga | ggctgggaaa | 1920 |
| acgtgactcc | cggagagaag | catgttgact | tttcctgggg | gcttccaagg | gaggggggccc | 1980 |
| cgccgtctgc | agtccagcat | ggaggcaccc | tgcttattaa | gcaggcgcca | cagctcaggg | 2040 |
| tcaatgcaag | acgcatcccc | tgcaaaacac | actggctcat | tttaaagctc | tcaccttcca | 2100 |
| aggcccgccc | gagtcccaag | tcccacccgc | gtccaccctc | cctgatccag | aggcgggatg | 2160 |
| gccggccggg | taggggcgc | ggggctcggc | ggggctctga | cggcgcggcc | tggcttgcag | 2220 |

```
gctagaggcg gccgaggcag cgggaggagc gagccccgat tccccccccgg agcgcggcgc    2280 gggcagcgcg gggcctgagc agcagcagcc gccactggag ccggacgccg agcgggacgc    2340
gggccccgag caggcccaga ccagctaccg cgacctgtgg agcctgcgcg cctcgcttga    2400
gctgcat                                                              2407
```

<210> SEQ ID NO 6
<211> LENGTH: 705
<212> TYPE: PRT
<213> ORGANISM: Homo sapiens

<400> SEQUENCE: 6

```
Met Gln Pro Thr Ala Thr Met Ala Thr Ala Thr Thr Thr Thr
1               5                  10                  15

Thr Thr Ala Thr Val Ala Leu Thr Thr Ser Trp Asp Asn Ala Thr Gly
            20                  25                  30

Arg Pro Thr Ala Glu Pro Asp Pro Ile Leu Asp Asn Tyr Val Leu Leu
        35                  40                  45

Val Val Val Met Ser Leu Phe Val Gly Gly Thr Leu Val Leu Ser
    50                  55                  60

Gly Val Leu Leu Leu Cys Lys Arg Cys Trp Asp Val His Gln Arg Phe
65                  70                  75                  80

Asn Arg Ala Met Glu Glu Ala Glu Lys Thr Thr Thr Thr Tyr Leu Asp
                85                  90                  95

Asn Gly Thr His Pro Ala Gln Asp Pro Asp Phe Arg Gly Glu Asp Pro
            100                 105                 110

Glu Cys Gln Asp Ala Glu Thr Glu Arg Phe Leu Ser Thr Ser Ser Thr
        115                 120                 125

Gly Arg Arg Val Ser Phe Asn Glu Ala Ala Leu Phe Glu Gln Ser Arg
    130                 135                 140

Lys Thr Gln Asp Lys Gly Arg Arg Tyr Thr Leu Thr Glu Gly Asp Phe
145                 150                 155                 160

His His Leu Lys Asn Ala Arg Leu Thr His Leu His Leu Pro Pro Leu
                165                 170                 175

Lys Ile Val Thr Ile His Glu Cys Asp Ser Gly Glu Ala Ser Ser Ala
            180                 185                 190

Thr Thr Pro His Pro Ala Thr Ser Pro Lys Ala Thr Leu Ala Ile Phe
        195                 200                 205

Gln Pro Pro Gly Lys Ala Leu Thr Gly Arg Ser Val Gly Pro Ser Ser
    210                 215                 220

Ala Leu Pro Gly Asp Pro Tyr Asn Ser Ala Thr Gly Ala Thr Asp Phe
225                 230                 235                 240

Ala Glu Ile Ser Pro Ser Ala Ser Ser Asp Ser Gly Glu Gly Thr Ser
                245                 250                 255

Leu Asp Ala Gly Thr Arg Ser Thr Lys Ala Gly Gly Pro Gly Ala Ala
            260                 265                 270

Ala Gly Pro Gly Glu Ala Gly Pro Gly Ser Gly Ala Gly Thr Val Leu
        275                 280                 285

Gln Phe Leu Thr Arg Leu Arg Arg His Ala Ser Leu Asp Gly Ala Ser
    290                 295                 300

Pro Tyr Phe Lys Val Lys Lys Trp Lys Leu Glu Pro Ser Gln Arg Ala
305                 310                 315                 320

Ala Ser Leu Asp Thr Arg Gly Ser Pro Lys Arg His Phe Gln Arg
                325                 330                 335
```

Gln Arg Ala Ala Ser Glu Ser Thr Glu Gln Ala Phe Pro Pro Pro
            340                 345                 350

Glu Gly Asp Ala Pro Gln Glu Asp Phe Ile Gln Tyr Ile Ala Arg Ala
        355                 360                 365

Gly Asp Ala Val Ala Phe Pro His Pro Arg Pro Phe Leu Ala Ser Pro
    370                 375                 380

Pro Pro Ala Leu Gly Arg Leu Glu Ala Ala Glu Ala Ala Gly Gly Ala
385                 390                 395                 400

Ser Pro Asp Ser Pro Glu Arg Gly Ala Gly Ser Ala Gly Pro Glu
                405                 410                 415

Gln Gln Gln Pro Pro Leu Glu Pro Asp Ala Glu Arg Asp Ala Gly Pro
                420                 425                 430

Glu Gln Ala Gln Thr Ser Tyr Arg Asp Leu Trp Ser Leu Arg Ala Ser
        435                 440                 445

Leu Glu Leu His Ala Ala Ala Ser Asp His Ser Ser Ser Gly Asn Asp
    450                 455                 460

Arg Asp Ser Val Arg Ser Gly Asp Ser Ser Gly Ser Gly Gly Gly
465                 470                 475                 480

Ala Ala Pro Ser Pro Ala Pro Arg Pro Lys Asp Gly Glu Ala Arg
                485                 490                 495

Arg Leu Leu Gln Met Asp Ser Gly Tyr Ala Ser Ile Glu Gly Arg Gly
            500                 505                 510

Ala Gly Asp Asp Thr Glu Pro Pro Ala Ala Pro Ala Arg Pro Arg Ser
        515                 520                 525

Pro Arg Ala Trp Pro Arg Arg Pro Arg Arg Asp Tyr Ser Ile Asp Glu
    530                 535                 540

Lys Thr Asp Ala Leu Phe His Glu Phe Leu Arg His Asp Pro His Phe
545                 550                 555                 560

Asp Asp Thr Pro Ala Ala Ala Arg His Arg Ala Arg Ala His Pro His
                565                 570                 575

Ala Arg Lys Gln Trp Gln Arg Gly Arg Gln His Ser Asp Pro Gly Ala
            580                 585                 590

Arg Ala Ala Pro Ala Leu Ala Gly Thr Pro Ala Pro Pro Ala Gly Ala
        595                 600                 605

Ala Arg Pro Ala Arg Ala Pro Leu Arg Arg Gly Asp Ser Val Asp Gly
    610                 615                 620

Pro Pro Asp Gly Arg Thr Leu Gly Gly Ala Gly Asp Asp Pro Ala Ile
625                 630                 635                 640

Pro Val Ile Glu Glu Glu Pro Gly Gly Gly Cys Pro Gly Ser Gly
                645                 650                 655

Leu Cys Val Leu Pro Ser Gly Ser Val Leu Asp Lys Leu Ala Ala Gly
            660                 665                 670

Leu Asp Glu Arg Leu Phe Pro Pro Arg Leu Ala Glu Pro Val Val Ala
        675                 680                 685

Thr Pro Ala Leu Val Ala Ala Pro Thr Ser Pro Asp His Ser Pro
    690                 695                 700

Ala
705

<210> SEQ ID NO 7
<211> LENGTH: 21
<212> TYPE: PRT
<213> ORGANISM: Artificial Sequence
<220> FEATURE:
<223> OTHER INFORMATION: Description of Artificial Sequence: Synthetic Domain 1 peptide

<400> SEQUENCE: 7

Ser Tyr Arg Asp Leu Trp Ser Leu Arg Ala Ser Leu Glu Leu His Ala
1               5                   10                  15

Ala Thr Ala Ser Asp
            20

<210> SEQ ID NO 8
<211> LENGTH: 39
<212> TYPE: PRT
<213> ORGANISM: Artificial Sequence
<220> FEATURE:
<223> OTHER INFORMATION: Description of Artificial Sequence: Synthetic
      Domain 2 polypeptide

<400> SEQUENCE: 8

Pro Arg Ala Trp Pro Arg Arg Pro Arg Arg Asp Tyr Ser Ile Asp Glu
1               5                   10                  15

Lys Thr Asp Ala Leu Phe His Glu Phe Leu Arg His Pro His Phe
            20                  25                  30

Asp Asp Ala Pro Arg His Arg
        35

<210> SEQ ID NO 9
<211> LENGTH: 11
<212> TYPE: PRT
<213> ORGANISM: Artificial Sequence
<220> FEATURE:
<223> OTHER INFORMATION: Description of Artificial Sequence: Synthetic
      antibody peptide

<400> SEQUENCE: 9

Asn Glu Ala Ala Leu Phe Glu Gln Ser Arg Lys
1               5                   10

<210> SEQ ID NO 10
<211> LENGTH: 32
<212> TYPE: PRT
<213> ORGANISM: Artificial Sequence
<220> FEATURE:
<223> OTHER INFORMATION: Description of Artificial Sequence: Synthetic
      AID polypeptide

<400> SEQUENCE: 10

Ala Lys Ala Arg Gly Asp Phe Gln Lys Leu Arg Glu Lys Gln Gln Leu
1               5                   10                  15

Glu Glu Asp Leu Lys Gly Ala Leu Asp Ala Ala Thr Gln Ala Glu Asp
            20                  25                  30

<210> SEQ ID NO 11
<211> LENGTH: 37
<212> TYPE: PRT
<213> ORGANISM: Artificial Sequence
<220> FEATURE:
<223> OTHER INFORMATION: Description of Artificial Sequence: Synthetic
      AID polypeptide

<400> SEQUENCE: 11

Lys Glu Arg Glu Lys Ala Lys Ala Arg Gly Asp Phe Gln Lys Leu Arg
1               5                   10                  15

Glu Lys Gln Gln Leu Glu Glu Asp Leu Lys Gly Tyr Leu Asp Trp Ile
            20                  25                  30

```
Thr Gln Ala Glu Asp
        35
```